United States Patent
Bourhis et al.

(10) Patent No.: US 8,846,041 B2
(45) Date of Patent: Sep. 30, 2014

(54) ANTI-LRP6 ANTIBODIES

(75) Inventors: Eric Bourhis, San Francisco, CA (US); Tim Cao, Millbrae, CA (US); Rick Carano, San Ramon, CA (US); Andrea Cochran, San Francisco, CA (US); Mike Costa, San Francisco, CA (US); Venita DeAlmeida, San Carlos, CA (US); James Ernst, San Francisco, CA (US); Yan Gong, San Francisco, CA (US); Rami Hannoush, San Mateo, CA (US); Paul Polakis, Mill Valley, CA (US); Bonnee Rubinfeld, Danville, CA (US); Mark Solloway, Palo Alto, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 247 days.

(21) Appl. No.: 13/069,582

(22) Filed: Mar. 23, 2011

(65) Prior Publication Data

US 2011/0256127 A1  Oct. 20, 2011

Related U.S. Application Data

(60) Provisional application No. 61/394,836, filed on Oct. 20, 2010, provisional application No. 61/317,137, filed on Mar. 24, 2010.

(51) Int. Cl.
*A61K 39/395* (2006.01)
*C07K 16/28* (2006.01)
*C12P 21/08* (2006.01)
*A61K 39/00* (2006.01)

(52) U.S. Cl.
CPC ......... *C07K 16/2863* (2013.01); *C07K 2317/21* (2013.01); *C07K 2317/75* (2013.01); *C07K 2317/55* (2013.01); *C07K 2317/31* (2013.01); *C07K 2319/00* (2013.01); *A61K 2039/507* (2013.01); *C07K 2317/526* (2013.01); *C07K 2317/92* (2013.01); *C07K 2317/34* (2013.01); *A61K 2039/505* (2013.01); *C07K 2317/76* (2013.01)
USPC .................. 424/136.1; 424/133.1; 424/141.1; 424/142.1; 424/139.1; 424/156.1; 530/387.3; 530/388.1; 530/388.15; 530/387.9; 530/388.85

(58) Field of Classification Search
None
See application file for complete search history.

(56) References Cited

U.S. PATENT DOCUMENTS

| | | |
|---|---|---|
| 2005/0070699 A1 | 3/2005 | Allen et al. |
| 2006/0252045 A1 | 11/2006 | Chatterjee-Kishore et al. |
| 2006/0257892 A1 | 11/2006 | Cohen et al. |
| 2007/0128187 A1 | 6/2007 | Allen et al. |
| 2007/0280948 A1 | 12/2007 | Williams et al. |
| 2007/0292348 A1* | 12/2007 | Williams et al. ............... 424/9.1 |
| 2012/0045437 A1 | 2/2012 | Ma et al. |

FOREIGN PATENT DOCUMENTS

| | | |
|---|---|---|
| WO | 02/092015 A2 | 11/2002 |
| WO | 2009/056634 A2 | 5/2009 |
| WO | 2010/108001 A2 | 9/2010 |
| WO | 2010/130832 A2 | 11/2010 |
| WO | 2011/138391 A1 | 11/2011 |
| WO | 2011/138392 A2 | 11/2011 |

OTHER PUBLICATIONS

Portolano et al., J. Immunol., 1993, vol. 150(3):880-887.*
Clackson et al., Nature, 1991, vol. 352:624-628.*
Knappik et al., J. Mol. Biol., 2000, vol. 296(1):57-86.*
Adams et al., "Structural and functional analysis of the interaction between the agonistic monoclonal antibody Apomab and the proapoptotic receptor DR5" Cell Death Differ. 15(4):751-61 (Apr. 2008).
Akiri et al., "Wnt pathway aberrations including autocrine Wnt activation occur at high frequency in human non-small-cell lung carcinoma" Oncogene 28(21):2163-72 (May 2009).
Bafico et al., "An autocrine mechanism for constitutive Wnt pathway activation in human cancer cells" Cancer Cell 6:497-506 (Nov. 2004).
Bilic et al., "Wnt induces LRP6 signalosomes and promotes dishevelled-dependent LRP6 phosphorylation" Science 316(5831):1619-22 (2007).
Binnerts et al., "The first propeller domain of LRP6 regulates sensitivity to DKK1" Mol Biol Cell. 20(15):3552-60 (2009).
Bourhis et al., "Reconstitution of a frizzled8.Wnt3a.LRP6 signaling complex reveals multiple Wnt and Dkk1 binding sites on LRP6" J Biol Chem. 285(12):9172-9 (2010).
Brott and Sokol, "Regulation of Wnt/LRP Signaling by Distinct Domains of Dickkopf Proteins" Mol Cell Biol 22(17):6100-6110 (Sep. 2002).
Cho et al., "Evolutionary dynamics of the wnt gene family: a lophotrochozoan perspective" Mol Biol Evol. (Epub Feb. 22, 2010), 27(7):1645-58 (2010).
Cong et al., "Wnt signals across the plasma membrane to activate the beta-catenin pathway by forming oligomers containing its receptors, Frizzled and LRP" Development 131(20):5103-15 (2004).
Cselenyi et al., "LRP6 transduces a canonical Wnt signal independently of Axin degradation by inhibiting GSK3's phosphorylation of beta-catenin" Proc Natl Acad Sci U S A. (Epub May 28, 2008), 105(23):8032-7 (2008).
Cunningham et al., "Identification of the extracellular domains of Flt-1 that mediate ligand interactions" Biochem Biophys Res Commun. 231(3):596-9 (1997).
Davis-Smyth et al., "The second immunoglobulin-like domain of the VEGF tyrosine kinase receptor Flt-1 determines ligand binding and may initiate a signal transduction cascade" EMBO J. 15(18):4919-27 (1996).
De Almeida, et al., "The soluble wnt receptor Frizzled8CRD-FC inhibits the growth of teratocarcinomas in vivo" Cancer Research 67(11):5371-5379 (Jun. 2007).

(Continued)

*Primary Examiner* — Xiaozhen Xie
(74) *Attorney, Agent, or Firm* — Traci H. Ropp

(57) ABSTRACT

The invention provides anti-LRP6 antibodies and methods of using the same. A particular aspect of the invention provides for bispecific anti-LRP6 antibodies that inhibit signaling by multiple Wnt isoforms.

16 Claims, 23 Drawing Sheets

(56) References Cited

OTHER PUBLICATIONS

Ettenberg et al., "Inhibition of tumorigenesis driven by different Wnt proteins requires blockade of distinct ligand-binding regions by LRP6 antibodies" Proc Natl Acad Sci U S A. 107(35):15473-8 (2010).

Glass et al., "Canonical Wnt signaling in differentiated osteoblasts controls osteoclast differentiation" Dev Cell. 8(5):751-64 (2005).

Gong et al., "Wnt isoform-specific interactions with coreceptor specify inhibition or potentiation of signaling by LRP6 antibodies" PLoS One 5(9):e12682 (Sep. 2010).

Guo et al., "Frzb, a secreted Wnt antagonist, decreases growth and invasiveness of fibrosarcoma cells associated with inhibition of Met signaling" Cancer Res. 68(9):3350-60 (2008).

Hsu et al., "Tumor necrosis factor receptor family member RANK mediates osteoclast differentiation and activation induced by osteoprotegerin ligand" Proc Natl Acad Sci U S A. 96(7):3540-5 (1999).

Itasaki et al., "Wise, a context-dependent activator and inhibitor of Wnt signalling" Development 130(18):4295-305 (2003).

Jeon et al., "Implications for familial hypercholesterolemia from the structure of the LDL receptor YWTD-EGF domain pair" Nat Struct Biol. 8(6):499-504 (2001).

Lintern et al., "Characterization of wise protein and its molecular mechanism to interact with both Wnt and BMP signals" J Biol Chem. 284(34):23159-68 (2009).

Liu et al,, "A novel mechanism for Wnt activation of canonical signaling through the LRP6 receptor" Mol Cell Biol. 23(16):5825-35 (2003).

Liu et al,, "Stromal cell-derived factor-1/CXCL12 contributes to MMTV-Wnt1 tumor growth involving Grl+CD11b+cells" PLoS One 5(1):e8611 (2010).

McDonald and Hendrickson, "A Structural Superfamily of Growth Factors Containing a Cystine Knot Motif" Cell 73:421-424 (1993).

Mi et al., "The low density lipoprotein receptor-related protein 6 interacts with glycogen synthase kinase 3 and attenuates activity" J Biol Chem. (Epub Dec. 19, 2005), 281(8):4787-94 (Feb. 24, 2006).

Mohammad et al., "Assessing new bone formation in neonatal calvarial organ cultures" Methods Mol Biol. 455:37-50 (2008).

Nguyen et al., "WNT/TCF signaling through LEF1 and HOXB9 mediates lung adenocarcinoma metastasis" Cell (Epub Jul. 2, 2009), 138(1):51-62 (2009).

Niida et al., "DKK1, a negative regulator of Wnt signaling, is a target of the beta-catenin/TCF pathway" Oncogene 23(52):8520-6 (2004).

PCT IPRP for PCT/US2011/029508.

PCT Written Opinion of the ISA for PCT/US2011/229508.

Piao et al., "Direct inhibition of GSK3beta by the phosphorylated cytoplasmic domain of LRP6 in Wnt/beta-catenin signaling" PLoS One (Epub Dec. 24, 2008), 3(12):e4046 (2008).

Quarto et al., "Origin Matters: Differences in Embryonic Tissue Origin and Wnt Signaling Determine the Osteogenic Potential and Healing Capacity of Frontal and Parietal Calvarial Bones" J Bone Miner Res. (Nov. 23, 2009 [Epub ahead of print]), 25(7) (Jul. 2010).

Rebay et al., "Specific EGF repeats of Notch mediate interactions with Delta and Serrate: implications for Notch as a multifunctional receptor" Cell 67(4):687-99 (1991).

Rudenko et al., "Structure of the LDL receptor extracellular domain at endosomal pH" Science 298(5602):2353-8 (2002).

Schwarz-Romond et al., "Dynamic recruitment of axin by Dishevelled protein assemblies" J Cell Sci. 120(Pt 14):2402-12 (2007).

Semenov et al., "Head Inducer Dickkopf-1 is a Ligand for Wnt Coreceptor LRP6" Curr Biol 11:951-961 (2001).

Semenov et al., "SOST is a ligand for LRP5/LRP6 and a Wnt signaling inhibitor" J Biol Chem. 280(29):26770-5 (2005).

Springer, "An extracellular beta-propeller module predicted in lipoprotein and scavenger receptors, tyrosine kinases, epidermal growth factor precursor, and extracellular matrix components" J Mol Biol. 283(4):837-62 (1998).

Takagi et al., "Complex between nidogen and laminin fragments reveals a paradigmatic beta-propeller interface" Nature 424(6951):969-74 (2003).

Tamai et al., "A mechanism for Wnt coreceptor activation" Mol. Cell. 13:149-156 (Jan. 16, 2004).

Tamai et al., "LDL-Receptor-Related Proteins in Wnt Signal Transduction" Nature 407:530-535 (Sep. 2000).

Van Amerongen et al., "Towards an integrated view of Wnt signaling in development" Development 136(19):3205-14 (2009).

Veverka et al., "Characterization of the structural features and interactions of sclerostin: molecular insight into a key regulator of Wnt-mediated bone formation" J Biol Chem. 284(16):10890-900 (2009).

Wu et al., "Inhibition of GSK3 phosphorylation of beta-catenin via phosphorylated PPPSPXS motifs of Wnt coreceptor LRP6" PLoS One (Epub Mar. 18, 2009), 4(3):e4926 (2009).

Yasui et al., "Detection of endogenous LRP6 expressed on human cells by monoclonal antibodies specific for the native conformation" J Immunol Methods (Epub Nov. 26, 2009), 352(1-2):153-60 (2010).

Ye et al., "The Norrin/Frizzled4 signaling pathway in retinal vascular development and disease" Trends Mol Med 16(9):417-425 (Sep. 2010).

Zeng et al., "Initiation of Wnt signaling: control of Wnt coreceptor Lrp6 phosphorylation/activation via frizzled, dishevelled and axin functions" Development (Epub Dec. 12, 2007), 135(2):367-75 (2008).

Zhang et al., "Inhibition of Wnt signaling by Dishevelled PDZ peptides" Nat Chem Biol. (Epub Mar. 1, 2009), 5(4):217-9 (2009).

Zhou et al., "Glucocorticoid-dependent Wnt signaling by mature osteoblasts is a key regulator of cranial skeletal development in mice" Development 136(3):427-36 (2009).

Zoltewicz et al., "Wnt signaling is regulated by endoplasmic reticulum retention" PLoS One 4(7):e6191 (2009).

Xi He, Mikail Semenov, Keiko Tamai & Xin Zeng, "Arrows point the way" Development 131:1663-1677 (2004).

* cited by examiner

| Tumor type | Cell line | Fold change in autocrine Wnt signaling with treatment | | |
|---|---|---|---|---|
| | | YW211.31.57 | YW210.09 | Fzd8CRD |
| Teratocarcinoma | Ntera-2 | 0.33 | 1.60 | 0.07 |
| | PA-1 | 0.11 | 3.34 | 0.08 |
| Breast | Hs578T | 1.98 | 1.27 | 0.60 |
| NSCLC | EKVX | 3.16 | 0.95 | 0.34 |
| | NCI-H23 | 2.15 | 0.37 | 0.35 |
| | NCI-H358 | 1.43 | 0.66 | 0.47 |
| | NCI-H2030 | 6.10 | 2.02 | 0.29 |
| Melanoma | M14 | 1.69 | 0.44 | 0.36 |
| Hepatocellular | JHH-1 | 6.25 | 2.01 | 0.63 |
| Soft tissue sarcoma | SW872 | 3.42 | 1.81 | 0.67 |
| | HT-1080 | 2.90 | 1.44 | 0.43 |

| Expression | HEK293 Cells Fold change in Wnt signaling with treatment | | | Hs578T Cells Fold change in Wnt signaling with treatment | | |
|---|---|---|---|---|---|---|
| | YW211.31.57 | YW210.09 | Fzd8CRD | YW211.31.57 | YW210.09 | Fzd8CRD |
| Wnt3 | 0.07 | 1.86 | 0.14 | 0.39 | 2.02 | 0.18 |
| Wnt3a | 0.07 | 3.79 | 0.09 | 0.52 | 3.23 | 0.12 |
| Wnt1 | 2.16 | 0.20 | 0.06 | 1.83 | 0.48 | 0.15 |
| Wnt2 | 6.18 | 0.10 | 0.14 | 3.36 | 0.22 | 0.06 |
| Wnt2b | 3.24 | 0.24 | 0.33 | 3.11 | 0.51 | 0.13 |
| Wnt6 | 4.41 | 0.34 | 0.71 | 2.67 | 0.62 | 0.15 |
| Wnt8a | 3.37 | 0.37 | 0.38 | 3.09 | 0.95 | 0.37 |
| Wnt9a | 1.47 | 0.51 | 0.35 | | | |
| Wnt9b | 1.38 | 0.67 | 0.92 | 4.21 | 0.95 | 0.41 |
| Wnt10b | 3.03 | 0.16 | 0.16 | 2.53 | 0.58 | 0.27 |
| Wnt4 | | | | 2.29 | 2.60 | 0.26 |
| Wnt7a | 3.54 | 1.42 | 0.22 | 5.83 | 4.72 | 0.14 |
| Wnt7b | 3.90 | 0.76 | 0.16 | 4.63 | 2.95 | 0.12 |
| Wnt10a | 2.53 | 1.07 | 0.30 | 2.88 | 0.66 | 0.11 |
| autocrine Wnt | | | | 2.56 | 1.87 | 0.59 |

| Expression | Fold change in Wnt signaling with treatment | | |
|---|---|---|---|
| | YW211.31.57 | YW210.09 | Fzd8CRD |
| Wnt3a-Fzd4 | 0.25 | 0.95 | 1.06 |
| Wnt3a-Fzd5 | 0.09 | 0.93 | 0.99 |
| Wnt1-Fzd4 | 4.41 | 0.38 | 1.31 |
| Wnt1-Fzd5 | 4.63 | 0.13 | 1.23 |
| Wnt3a-LRP6 | 0.85 | 1.20 | 0.97 |
| Wnt1-LRP6 | 1.23 | 1.12 | 0.28 |
| LRP6 | 0.40 | 1.28 | 1.13 |

FIG. 7

| Expression | Fold change in Wnt signaling with treatment | | |
|---|---|---|---|
| | YW211.31.57 | YW210.09 | YW211.31.57 + YW210.09 |
| Wnt3a | 0.07 | 3.79 | 0.03 |
| Wnt1 | 1.57 | 0.30 | 0.42 |
| Wnt8A | 3.37 | 0.37 | 0.22 |
| Wnt9B | 1.38 | 0.67 | 0.46 |
| Wnt10B | 3.03 | 0.16 | 0.08 |
| Wnt7A | 3.54 | 1.42 | 1.98 |
| Wnt7B | 3.90 | 0.76 | 1.80 |
| Wnt10A | 2.53 | 1.07 | 0.83 |

| Expression | HEK293 Cells Fold change in Wnt signaling with treatment | | | | | | Hs578T Cells Fold change in Wnt signaling with treatment | | | | | |
|---|---|---|---|---|---|---|---|---|---|---|---|---|
| | anti-gD | YW211.31.57 | YW210.09 | YW210+YW211 | bispecific | Fzd8CRD | anti-gD | YW211.31.57 | YW210.09 | YW210+YW211 | bispecific | Fzd8CRD |
| vector | 0.80 | 1.06 | 0.97 | 0.87 | 0.83 | 0.77 | 1.06 | 1.22 | 0.99 | 1.21 | 0.84 | 0.70 |
| Wnt3 | 1.05 | 0.09 | 4.26 | 0.06 | 0.04 | 0.25 | 0.79 | 0.12 | 2.29 | 0.21 | 0.03 | 0.19 |
| Wnt3a | 1.07 | 0.14 | 4.08 | 0.08 | 0.03 | 0.26 | 0.86 | 0.26 | 2.97 | 0.31 | 0.07 | 0.22 |
| Wnt1 | 1.21 | 2.53 | 0.22 | 0.56 | 0.06 | 0.08 | 0.86 | 1.32 | 0.30 | 0.31 | 0.10 | 0.21 |
| Wnt2 | 0.83 | 3.70 | 0.13 | 0.23 | 0.09 | 0.15 | 0.67 | 2.91 | 0.30 | 0.42 | 0.27 | 0.28 |
| Wnt2b | 1.08 | 2.56 | 0.32 | 0.30 | 0.25 | 0.43 | | | | | | |
| Wnt6 | 0.94 | 5.00 | 0.37 | 0.45 | 0.30 | 0.61 | 0.86 | 3.19 | 0.48 | 0.72 | 0.33 | 0.22 |
| Wnt8a | 1.08 | 5.39 | 0.28 | 0.30 | 0.21 | 0.45 | | | | | | |
| Wnt9a | 1.03 | 2.27 | 0.91 | 0.74 | 0.31 | 0.79 | | | | | | |
| Wnt9b | 1.27 | 1.81 | 0.87 | 0.57 | 0.24 | 1.22 | 0.89 | 2.22 | 0.50 | 0.34 | 0.24 | 0.74 |
| Wnt10b | 1.28 | 3.19 | 0.22 | 0.32 | 0.04 | 0.40 | 0.90 | 2.30 | 0.42 | 0.51 | 0.26 | 0.61 |
| Wnt4 | | | | | | | | | | | | |
| Wnt7a | 1.22 | 5.76 | 1.65 | 3.67 | 0.50 | 0.48 | 0.95 | 4.63 | 2.92 | 3.66 | 0.89 | 0.29 |
| Wnt7b | 1.16 | 5.54 | 0.90 | 3.69 | 0.59 | 0.38 | 1.03 | 4.06 | 2.29 | 6.46 | 0.59 | 0.20 |
| Wnt10a | 1.30 | 2.48 | 1.01 | 1.56 | 0.38 | 0.42 | 0.92 | 2.94 | 0.55 | 1.04 | 0.20 | 0.19 |
| Wnt1+Wnt3a | 1.16 | 1.16 | 1.13 | 0.30 | 0.08 | 0.13 | 0.86 | 0.70 | 0.86 | 0.46 | 0.16 | 0.22 |

FIG. 12

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | Kabat - CDR H1 | | | | | | | | | |
| YW211.31 | E | V | Q | L | V | E | S | G | G | G | L | V | Q | P | G | G | S | L | R | L | S | C | A | A | S | G | F | T | F | T | S | Y | Y | I | S | W | V | R | Q | A |
| YW211.31.57 | E | V | Q | L | V | E | S | G | G | G | L | V | Q | P | G | G | S | L | R | L | S | C | A | A | S | G | F | T | F | S | Y | Y | Y | I | S | W | V | R | Q | A |
| YW211.31.62 | E | V | Q | L | V | E | S | G | G | G | L | V | Q | P | G | G | S | L | R | L | S | C | A | A | S | G | F | T | F | Y | Y | Y | Y | I | S | W | V | R | Q | A |
| YW210.09 | E | V | Q | L | V | E | S | G | G | G | L | V | Q | P | G | G | S | L | R | L | S | C | A | A | S | G | F | T | F | T | N | S | Y | I | H | W | V | R | Q | A |

| Kabat# | 41 | 42 | 43 | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | Kabat - CDR H2 | | | | | | | | | | | | | | | | | | | | | | | | | |
| YW211.31 | P | G | K | G | L | E | W | V | A | H | I | S | P | | | Y | S | G | S | T | Y | Y | A | D | S | V | K | G | R | F | T | I | S | A | D | T | S | K | N | T | A |
| YW211.31.57 | P | G | K | G | L | E | W | V | A | H | I | S | P | | | Y | S | G | S | T | Y | Y | A | D | S | V | K | G | R | F | T | I | S | A | D | T | S | K | N | T | A |
| YW211.31.62 | P | G | K | G | L | E | W | V | A | H | I | S | P | | | Y | S | G | S | T | Y | Y | A | D | S | V | K | G | R | F | T | I | S | A | D | T | S | K | N | T | A |
| YW210.09 | P | G | K | G | L | E | W | V | G | W | I | T | P | | | Y | G | G | Y | I | N | Y | A | D | S | V | K | G | R | F | T | I | S | A | D | T | S | K | N | T | A |

| Kabat# | 79 | 80 | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | 101 | 102 | 103 | 104 | 105 | | |
|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | Kabat - CDR H3 | | | | | | | | | | | | | | | | |
| YW211.31 | Y | L | Q | M | N | S | L | R | A | E | D | T | A | V | Y | Y | C | A | L | R | A | R | P | P | I | R | L | H | P | R | G | S | W | M | D | Y | W | G | Q | SEQ ID NO: 9 |
| YW211.31.57 | Y | L | Q | M | N | S | L | R | A | E | D | T | A | V | Y | Y | C | A | L | R | A | R | P | P | I | R | L | Y | P | R | G | S | W | M | D | Y | W | G | Q | SEQ ID NO: 11 |
| YW211.31.62 | Y | L | Q | M | N | S | L | R | A | E | D | T | A | V | Y | Y | C | A | L | R | A | R | P | P | I | R | L | H | P | R | G | S | W | M | D | Y | W | G | Q | SEQ ID NO: 13 |
| YW210.09 | Y | L | Q | M | N | S | L | R | A | E | D | T | A | V | Y | Y | C | A | R | G | S | G | H | V | N | A | V | K | N | Y | G | V | W | M | D | Y | W | G | Q | SEQ ID NO: 15 |

*FIG. 16*

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | Kabat - CDR L1 | | |
| YW211.31 | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW211.31.57 | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW211.31.62 | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW210.09 | D | I | Q | M | T | Q | S | P | S | S | L | S | A | S | V | G | D | R | V | T | I | T | C | R | A | S | Q | | | | | | | D | V | S | T | A | V | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | Kabat - CDR L2 | | | | | | | | | | | | | | | | | | | | | | | | | | | | | | |
| YW211.31 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| YW211.31.57 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| YW211.31.62 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| YW210.09 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|---|---|---|---|---|---|
| | | | | | | | | | | Kabat - CDR L3 | | | | | | | | | | | | | | | | | | | |
| YW211.31 | E | D | F | A | T | Y | Y | C | Q | Q | S | Y | T | T | P | P | T | F | G | Q | G | T | K | V | E | I | K | R | SEQ ID NO: 10 |
| YW211.31.57 | E | D | F | A | T | Y | Y | C | Q | Q | S | Y | T | L | P | P | T | F | G | Q | G | T | K | V | E | I | K | R | SEQ ID NO: 12 |
| YW211.31.62 | E | D | F | A | T | Y | Y | C | Q | Q | S | Y | T | T | P | P | T | F | G | Q | G | T | K | V | E | I | K | R | SEQ ID NO: 14 |
| YW210.09 | E | D | F | A | T | Y | Y | C | Q | Q | S | Y | T | T | P | P | T | F | G | Q | G | T | K | V | E | I | K | R | SEQ ID NO: 16 |

ANTI-LRP6 ANTIBODIES

CROSS REFERENCE TO RELATED APPLICATIONS

This application claims the benefit of U.S. Provisional Application No. 61/317,137, filed Mar. 24, 2010, and U.S. Provisional Application No. 61/394,836, filed Oct. 20, 2010, the disclosures of which are incorporated herein by reference in their entirety.

FIELD OF THE INVENTION

The present invention relates to anti-LRP6 antibodies and methods of using the same for the treatment of cancer or skeletal disorders.

BACKGROUND

Similar to most other morphogen and growth factor signaling pathways, mammalian Wnt signaling is deployed multiple times during development and tissue homeostasis through the use of 19 different ligands, 10 receptors, and multiple coreceptors, including LRP5/6, Ror1/2, and Ryk (van Amerongen and Nusse, 2009). In addition, different secreted antagonists that bind either Wnts, such as SFRP1/2/3/4/5 and WIF1, or LRP5/6, including DKK1/2/4 and SOST, modulate interactions between ligands and receptors. These membrane and extracellular proteins and their multiple isoforms provide for differential regulation at the level of expression and combinatorial protein interactions. Most Wnt isoforms appear to be capable of binding coreceptor LRP5/6, and LRP5/6 engagement specifies canonical, or β-catenin dependent, Wnt signaling. Wnt heterodimerizes LRP5/6 and FZD to mediate phosphorylation of the LRP5/6 intracellular domain and Axin binding (Tamai et al., 2000; Semenov et al., 2001; Tamai et al., 2004). DVL is brought into the complex by directly binding both Axin and FZD, and DVL oligomerization likely enlarges these protein complexes on the cytoplasmic face of the membrane that sequester GSK3 and inhibit its phosphorylation and destabilization of β-catenin (Mi et al., 2006; Bilic et al., 2007; Schwarz-Romond et al., 2007; Cselenyi et al., 2008; Piao et al., 2008; Zeng et al., 2008; Wu et al., 2009).

The uniquely large number of ligand isoforms, displaying considerable primary sequence divergence, that mediate mammalian canonical Wnt signaling contrasts with the pair of highly homologous coreceptors. The LRP6 and LRP5 extracellular domains consist largely of four homologous regions, named E1 to E4 from N- to C-terminal, each containing a YWTD-type β-propeller and EGF-like domain (Jeon et al., 2001). Each repeat at a similar position in LRP6 and LRP5 is highly conserved, whereas the different repeats within the same protein are considerably more divergent. Interestingly, Bourhis et al. (2010) demonstrated that Wnt9b binds exclusively within the E1-E2 region in vitro, whereas Wnt3a binds only to a fragment containing E3-E4, suggesting that each repeat, or a combination of two adjacent repeats, binds to a different subset of Wnt isoforms. This arrangement may accommodate the diversity of Wnt proteins, and possibly also allow for their differential regulation by LRP5/6 antagonist ligands. In Notch and VEGF receptors, whose extracellular regions contain repeats of EGF-like and Ig domains, respectively, binding of multiple ligand isoforms is localized to the same region of one or two repeats, although the presence of other repeats can enhance binding. (Rebay et al., 1991; Davis-Smyth et al., 1996; Cunningham et al., 1997).

For receptor tyrosine kinases, ligand-induced dimerization initiates stimulation of the kinase activity and signaling. While ligand-induced receptor-coreceptor heterodimerization is necessary for canonical Wnt signaling, there is no clearly defined role for LRP5/6 or FZD homodimerization. Forced dimerization of different recombinant LRP6 proteins can either activate or inhibit Wnt signaling.

β-catenin-dependent Wnt signaling is initiated by a Wnt isoform binding to both the receptor FZD and coreceptor LRP5/6, which then assembles a multimeric complex at the cytoplasmic membrane face to recruit and inactivate the kinase GSK3. Whether and how mechanistically different interactions between Wnt isoforms and receptors might modulate this process remains to be determined

SUMMARY

One aspect of the invention provides for an isolated antibody that binds to LRP6, wherein the antibody inhibits signaling induced by a first Wnt isoform and potentiates signaling induced by a second Wnt isoform. In one embodiment, the first Wnt isoform is selected from the group consisting of Wnt3 and Wnt3a. In one embodiment, the second Wnt isoform is selected from the group consisting of Wnt 1, 2, 2b, 4, 6, 7a, 7b, 8a, 9a, 9b, 10a, and 10b. In another embodiment, the first Wnt isoform is selected from the group consisting of Wnts 1, 2, 2b, 6, 8a, 9a, 9b, and 10b and the second Wnt isoform is selected from the group consisting of Wnt3 and Wnt3a.

One aspect of the invention provides for an antibody binds to the E3-E4 region of LRP6. Another aspect of the invention provides for an antibody binds to the E1-E2 region of LRP6. Yet another aspect provides for an antibody that binds to two different regions of LRP6, such as the E1-E2 region of LRP6 and the E3-E4 region. In one aspect these antibodies inhibit Wnt signaling induced by the combination of Wnt1 and Wnt3a. In one aspect these antibodies inhibit autocrine Wnt signaling.

One aspect of the invention provides a method of treating an individual having cancer comprising administering to the individual an effective amount of an isolated antibody that binds to LRP6 and inhibits signaling induced by a Wnt isoform selected from the group consisting of Wnt3 and Wnt3a, and an isolated antibody that binds to LRP6 and inhibits signaling induced by a Wnt isoform selected from the group consisting of Wnt 1, 2, 2b, 6, 8a, 9a, 9b, and 10b.

Another aspect of the invention provides for a method of treating an individual having cancer comprising administering to the individual an effective amount of an isolated antibody that binds to LRP6 and inhibits signaling induced by Wnt3 and Wnt3a, and an isolated antibody that binds to LRP6 and inhibits signaling induced by Wnt 1, 2, 2b, 6, 8a, 9a, 9b, and 10b.

Another aspect of the invention provides for a method of treating an individual having cancer comprising administering to the individual an effective amount of an isolated antibody that binds to LRP6 and inhibits signaling induced by Wnt3 and Wnt3a, and an isolated antibody that binds to LRP6 and inhibits signaling induced by Wnt 1, 2, 2b, 4, 6, 7a, 7b, 8a, 9a, 9b, 10a, and 10b.

One aspect of the invention provides a method of treating an individual having a skeletal disorder, such as osteoporosis, osteoarthritis, bone fractures, and bone lesions, comprising administering to the individual an effective amount of an anti-LRP6 antibody described herein.

Another aspect of the invention provides for a method of potentiating Wnt signaling induced by a Wnt isoform in an individual comprising administering to the individual an effective amount of an anti-LRP6 antibody described herein and the Wnt isoform to potentiate Wnt signaling induced by the Wnt isoform.

Also provide are specific anti-LRP6 antibodies, including bispecific ant-LRP6 antibodies. In one embodiment, the isolated antibody that binds to LRP6 comprises a VH comprising an amino acid sequence selected from the group consisting of SEQ ID NO: 9, SEQ ID NO: 11, SEQ ID NO: 13, and SEQ ID NO: 15. In one embodiment, the antibody further comprises a VL comprising an amino acid sequence selected from the group consisting SEQ ID NO: 10 and SEQ ID NO: 12. In one embodiment, the isolated antibody that binds to LRP6 comprises a VH comprising an amino acid sequence having at least 90% homology to an amino acid sequence of SEQ ID NO: 9, SEQ ID NO: 11, SEQ ID NO: 13, and SEQ ID NO: 15. In one embodiment, the isolated antibody that binds to LRP6 further comprises a VL comprising an amino acid sequence having at least 90% homology to an amino acid sequence selected from the group consisting of SEQ ID NO: 10 and SEQ ID NO: 12.

In one embodiment, the antibody is an isolated bispecific antibody that binds to two different regions of LRP6 wherein the antibody comprises a VH comprising the amino acid sequence selected from the group consisting of SEQ ID NO: 9, SEQ ID NO: 11, SEQ ID NO: 13, and SEQ ID NO: 15. In one embodiment, the bispecific antibody comprises a first VH comprising the amino acid sequence of SEQ ID NO: 15 and a second VH comprising the amino acid sequence selected from the group consisting of SEQ ID NO: 9, SEQ ID NO: 11, and SEQ ID NO: 13. In one embodiment, the bispecific antibody further comprises a VL comprising the amino acid sequence selected from the group consisting of SEQ ID NO: 10 and SEQ ID NO: 12.

In one embodiment, the bispecific antibody that binds to two different regions of LRP6 comprises a VH comprising an amino acid sequence having at least 90% homology to an amino acid sequence selected from the group consisting of SEQ ID NO: 9, SEQ ID NO: 11, SEQ ID NO: 13, or SEQ ID NO: 15. In one embodiment, the bispecific antibody that binds to two different regions of LRP6 comprises a first VH comprising an amino acid sequence having at least 90% homology to an amino acid sequence of SEQ ID NO: 15 and a second VH comprising an amino acid sequence having at least 90% homology to an amino acid sequence selected from the group consisting of SEQ ID NO: 9, SEQ ID NO: 11, and SEQ ID NO: 13. In one embodiment, the bispecific antibody further comprises a VL comprising an amino acid sequence having at least 90% homology to an amino acid sequence selected from the group consisting of SEQ ID NO: 10, and SEQ ID NO: 12.

In one embodiment, the isolated bispecific antibody that binds to two different regions of LRP6 comprises a first VH domain comprising at least one, at least two, or all three VH HVR sequences selected from (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 19 and comprises a second VH domain comprising at least one, at least two, or all three VH HVR sequences selected from (d) HVR-H1 comprising the amino acid sequence of SEQ ID NO: 22; (e) HVR-H2 comprising the amino acid sequence of SEQ ID NO: 23; and (f) HVR-H3 comprising the amino acid sequence of SEQ ID NO: 24. In one embodiment, the isolated bispecific antibody that binds to two different regions of LRP6 comprises a first VH domain comprising all three VH HVR sequences from (a) HVR-H1 comprising the amino acid sequence of SEQ ID NO: 17; (b) HVR-H2 comprising the amino acid sequence SEQ ID NO: 18; (c) HVR-H3 comprising the amino acid sequence SEQ ID NO: 19 and comprises a second VH domain comprising all three VH HVR sequences from (d) HVR-H1 comprising the amino acid sequence of SEQ ID NO: 22; (e) HVR-H2 comprising the amino acid sequence of SEQ ID NO: 23; and (f) HVR-H3 comprising the amino acid sequence of SEQ ID NO: 24.

In one embodiment, the isolated bispecific antibody that binds to two different regions of LRP6 comprises a first VH domain comprising at least one, at least two, or all three VH HVR sequences selected from (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 21 and comprises a second VH domain comprising at least one, at least two, or all three VH HVR sequences selected from (d) HVR-H1 comprising the amino acid sequence of SEQ ID NO: 22; (e) HVR-H2 comprising the amino acid sequence of SEQ ID NO: 23; and (f) HVR-H3 comprising the amino acid sequence of SEQ ID NO: 24. In one embodiment, the isolated bispecific antibody that binds to two different regions of LRP6 comprises a first VH domain comprising all three VH HVR sequences from (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 21 and comprises a second VH domain comprising all three VH HVR sequences from (d) HVR-H1 comprising the amino acid sequence of SEQ ID NO: 22; (e) HVR-H2 comprising the amino acid sequence of SEQ ID NO: 23; and (f) HVR-H3 comprising the amino acid sequence of SEQ ID NO: 24.

In one embodiment, the isolated bispecific antibody that binds to two different regions of LRP6 comprises a first VH domain comprising at least one, at least two, or all three VH HVR sequences selected from (a) HVR-H1 comprising the amino acid sequence of SEQ ID NO: 20; (b) HVR-H2 comprising the amino acid sequence of SEQ ID NO: 18; (c) HVR-H3 SEQ ID NO: 19 and comprises a second VH domain comprising at least one, at least two, or all three VH HVR sequences selected from (d) HVR-H1 comprising the amino acid sequence of SEQ ID NO: 22; (e) HVR-H2 comprising the amino acid sequence of SEQ ID NO: 23; and (f) HVR-H3 comprising the amino acid sequence of SEQ ID NO: 24. In one embodiment, the isolated bispecific antibody that binds to two different regions of LRP6 wherein the antibody comprises a first VH domain comprising all three VH HVR sequences from (a) HVR-H1 comprising the amino acid sequence of SEQ ID NO: 20; (b) HVR-H2 comprising the amino acid sequence of SEQ ID NO: 18; (c) HVR-H3 comprising the amino acid sequence of SEQ ID NO: 19 and comprises a second VH domain comprising all three VH HVR sequences from (d) HVR-H1 comprising the amino acid sequence of SEQ ID NO: 22; (e) HVR-H2 comprising the amino acid sequence of SEQ ID NO: 23; and (f) HVR-H3 comprising the amino acid sequence of SEQ ID NO: 24.

In one embodiment, the bispecific antibody in the above embodiments further comprises at least one, at least two, or all three VL HVR sequences selected from (a) HVR-L1 comprising the amino acid sequence of SEQ ID NO: 25; (b) HVR-L2 comprising the amino acid sequence of SEQ ID NO: 26; (c) HVR-L3 SEQ ID NO: 27.

In one embodiment, the bispecific antibody in the above embodiments further comprises at least one, at least two, or all three VL HVR sequences selected from (a) HVR-L1 comprising the amino acid sequence of SEQ ID NO: 25; (b) HVR-L2 comprising the amino acid sequence of SEQ ID NO: 26; (c) HVR-L3 SEQ ID NO: 28.

One embodiment provides for an isolated bispecific antibody that binds to two different regions of LRP6, wherein the antibody comprises a first VH comprising the amino acid sequence of SEQ ID NO: 15 and a second VH selected from the group consisting of a VH comprising the amino acid sequence of SEQ ID NO: 9, SEQ ID NO: 11, and SEQ ID NO: 13. In one embodiment, this antibody further comprises a VL comprising the amino acid sequence of SEQ ID NO: 10 or SEQ ID NO: 12. In one embodiment, the bispecific antibody comprises a first VH comprising the amino acid sequence of SEQ ID NO: 15 and a second VH comprising the amino acid sequence of SEQ ID NO: 9, and a VL comprising the amino acid sequence of SEQ ID NO: 10.

In one embodiment, the bispecific antibody inhibits signaling induced by a Wnt isoform selected from the group consisting of Wnt3 and Wnt3a and inhibits signaling induced by a Wnt isoform selected from the group consisting of Wnt 1, 2, 2b, 6, 8a, 9a, 9b, and 10b. In one embodiment the bispecific antibody further inhibits signaling induced by a Wnt isoform selected from the group consisting of Wnt 4, 7a, 7b, and 10a. In one embodiment the bispecific antibody inhibits autocrine Wnt signaling.

One aspect of the invention provides a bispecific antibody that inhibits signaling induced by a Wnt isoform selected from the group consisting of Wnt3 and Wnt3a and inhibits signaling induced by a Wnt isoform selected from the group consisting of Wnt 1, 2, 2b, 6, 8a, 9a, 9b, and 10b. In one embodiment, the bispecific antibody further inhibits signaling induced by a Wnt isoform selected from the group consisting of Wnt 4, 7a, 7b, and 10a.

One aspect of the invention provides for an antibody that competes for binding to LRP6 with any of the anti-LRP6 antibodies, including the bispecific antibodies, described herein.

Another aspect of the invention provides for an antibody that binds to the same two epitopes as a bispecific antibody described herein. In one embodiment, one of the two epitopes comprises amino acid residues R28, E51, D52, V70, S71, E73, L95, S96, D98, E115, R141, and N185 of LRP6. In one embodiment, one of the two epitopes comprises amino acid residues R28, E51, D52, V70, S71, E73, L95, S96, D98, E115, R141, N185, R29, W188, K202, P225, H226, S243, and F266 of LRP6.

Another aspect of the invention provides an isolated nucleic acid encoding an anti-LRP6 antibody described herein. Another aspect provides for a host cell comprising such a nucleic acid.

One aspect of the invention provides for an immunoconjugate comprising an anti-LRP6 antibody described herein and a cytotoxic agent. Another aspect provides for a pharmaceutical formulation comprising an anti-LRP6 antibody described herein and a pharmaceutically acceptable carrier.

One aspect of the invention provides a method of treating an individual having cancer, such as non-small cell lung cancer, breast cancer, pancreatic cancer, ovarian cancer, kidney cancer, and prostate cancer, comprising administering to the individual an effective amount of an anti-LRP6 antibody described herein.

BRIEF DESCRIPTION OF THE FIGURES

FIG. 2B. Graph showing result of qPCR expression analysis of Wnt-induced genes $SAX_1$ and GAD1 and Wnt-repressed gene LEFTY2 in PA-1 cells treated with or without 0.3 mg/ml Wnt3a protein, and treated with 10 mg/ml YW211.31 antibody, anti-gD monoclonal antibody (negative control) or Fzd8CRD-Fc protein (positive control). Data is normalized to samples from cells with no addition (NA) of Wnt3a.

FIG. 3. Summary table showing the effects of LRP6 antibodies and Fzd8CRD-Fc protein on autocrine signaling in cell lines.

FIG. 4A. Graph depicting the result of qPCR expression analysis of AXIN2 mRNA in four cell lines treated with 25 μg/ml YW211.31.57 antibody or Fzd8CRD-Fc protein, with and without (NA) 0.2 μg/ml Wnt3a.

FIG. 5. Summary table of the effects of 10 mg/ml LRP6 antibodies or Fzd8CRD-Fc protein on signaling induced by transfection of expression constructs for Wnt isoforms in HEK293 or Hs578T cell lines stably integrated with Wnt luciferase reporters. Expression of Wnt luciferase reporter is normalized to cell number and additionally normalized to levels in cells transfected the same expression construct but not treated with proteins.

FIG. 6. Summary table of the effects of 10 mg/ml LRP6 antibodies or Fzd8CRD-Fc protein on signaling in HEK293 cell lines stably integrated with Wnt luciferase reporters. The signaling was induced by transfection of expression constructs for chimeric proteins consisting of Wnt isoforms fused to FZD isoforms or LRP6. Expression of Wnt luciferase reporter is normalized to cell number and additionally normalized to levels in cells transfected the same expression construct but not treated with proteins.

FIG. 7. Summary table of the effects of 10 mg/ml LRP6 antibodies or antibody combinations on signaling induced by transfection of expression constructs for Wnt isoforms in cell lines stably integrated with Wnt luciferase reporters. Expression of Wnt luciferase reporter is normalized to cell number and additionally normalized to levels in cells transfected the same expression construct but not treated with proteins.

FIG. 11B. Graph showing effect of treatment with the indicated control buffer (PBS), antibody, antibody combination, or Fzd8CRD-Fc protein (10 μg/ml each) on autocrine Wnt signaling in PA-1 and M14 cells stably integrated with Wnt luciferase reporter, and CAL-51 cells transfected with reporter, were treated with the indicated control buffer (PBS), antibody, antibody combination, or Fzd8CRD-Fc protein (10 μg/ml each) with (C) or without (B) stimulation by 0.1 μg/ml Wnt3a.

FIG. 11C. Graph showing effect of treatment with the indicated control buffer (PBS), antibody, antibody combination, or Fzd8CRD-Fc protein (10 μg/ml each) on PA-1 and M14 cells stably integrated with Wnt luciferase reporter, and CAL-51 cells transfected with reporter, stimulated by 0.1 μg/ml Wnt3a.

FIG. 12 Summary table of the effects of antibodies or Fzd8CRD protein (10 μg/ml) on signaling induced by transfection of expression constructs for Wnt isoforms in HEK293 or Hs578T cell lines stably integrated with Wnt luciferase reporter.

FIG. 16 Heavy chain variable region (VH) of exemplary anti-LRP6 antibodies showing Kabat CDRs.

FIG. 17. Light chain variable region (VL) of exemplary anti-LRP6 antibodies showing Kabat CDRs.

DETAILED DESCRIPTION OF EMBODIMENTS OF THE INVENTION

I. Definitions

Figure 1A:
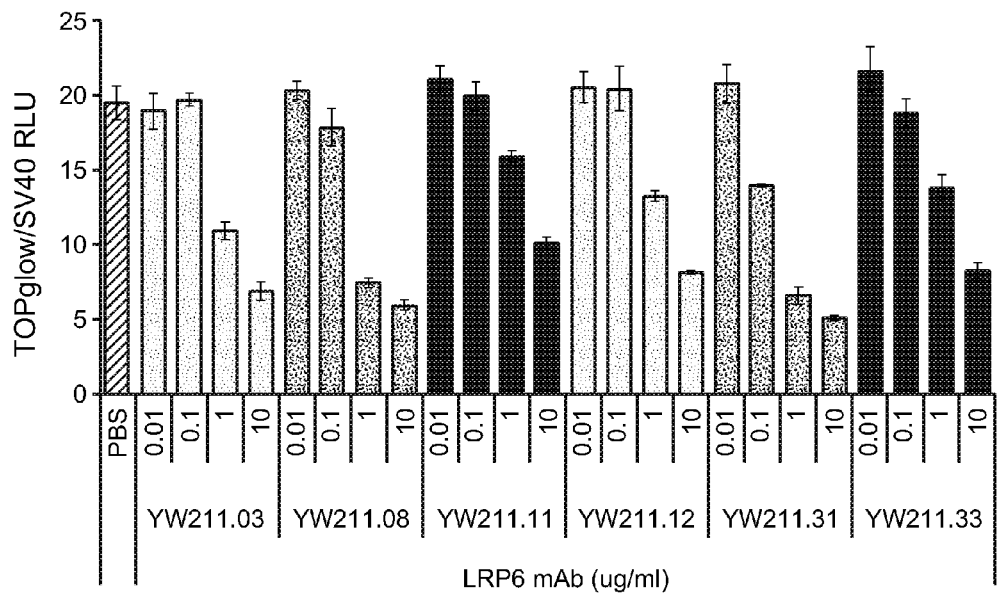
FIG. 1A. Graph showing inhibition of Wnt luciferase reporter activity in HEK293 cells induced with 0.1 mg/ml purified Wnt3a by antibodies against LRP6.E3-E4 protein.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-LRP6 antibody" and "an antibody that binds to LRP6" refer to an antibody that is capable of binding LRP6 with sufficient affinity such that the antibody is useful as a diagnostic and/or therapeutic agent in targeting LRP6. In one embodiment, the extent of binding of an anti-LRP6 antibody to an unrelated, non-LRP6 protein is less than about 10% of the binding of the antibody to LRP6 as measured, e.g., by a radioimmunoassay (RIA). In certain embodiments, an antibody that binds to LRP6 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-LRP6 antibody binds to an epitope of LRP6 that is conserved among LRP6 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/ zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyl-transferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $SM^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-LRP6 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "LRP6", as used herein, refers to any native LRP6 from any vertebrate source, including mammals such as primates (e.g. humans) and rodents (e.g., mice and rats), unless otherwise indicated. The term encompasses "full-length," unprocessed LRP6 as well as any form of LRP6 that results from processing in the cell. The term also encompasses naturally occurring variants of LRP6, e.g., splice variants or allelic variants. The amino acid sequence of an exemplary human LRP6 is shown in SEQ ID NO: 29. See also NCBI accession number AAI43726, Strausberg, R. L., et al., Proc. Natl. Acad. Sci. U.S.A. 99: 16899-16903 (2002) (He, X, et al., Development, 131:1663-1677 (2004); Chen, M., et al., J. Biol. Chem., 284:35040-35048 (2009).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6*th* ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al. *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

The present invention provides anti-LRP6 antibodies with the unexpected ability to inhibit signaling by some Wnt isoforms and potentiate signaling by other isoforms. As described in the Examples, two anti-LRP6 antibodies characterized further show reciprocal activities on most Wnts, with one antibody antagonizing and the other potentiating. These two antibodies bind to different regions of LRP6 (as do different Wnt isoforms) and inhibition of signaling results from blocking Wnt binding.

Based on their functional interaction with anti-LRP6 antibodies of the invention, the 14 Wnt isoforms tested can be grouped into three classes: Wnt3 and Wnt3a are inhibited by anti-LRP6 antibody YW211.31 and potentiated by anti-LRP6 antibody YW210.09; Wnts 1, 2, 2B, 6, 8A, 9A, 9B, and 10B are potentiated by anti-LRP6 antibody YW211.31 and antagonized by anti-LRP6 antibody YW210.09; and Wnts 4, 7A, 7B, and 10A are potentiated by anti-LRP6 antibody YW211.31 and not inhibited by anti-LRP6 antibody YW210.09 (FIG. 3C). These classifications do not obviously correspond to the proposed phylogeny of Wnt genes, although the Wnt3/3a subfamily is the most evolutionarily divergent (Cho et al., 2010). Combinations of anti-LRP6 antibodies that inhibit the different classes of Wnt isoforms can be used to provide an effective therapeutic for treating diseases associated with Wnt signaling.

Antibody-mediated dimerization of LRP6 can potentiate signaling only when a Wnt isoform is also able to bind the complex, presumably recruiting FZD. Endogenous autocrine Wnt signaling in different tumor cell lines can be either antagonized or enhanced by the LRP6 antibodies. This complexity of coreceptor-ligand interactions may allow for differential regulation of signaling by Wnt isoforms, and can be exploited with antibodies to differentially manipulate Wnt signaling in specific tissues or disease states.

In some embodiments, the anti-LRP6 antibodies can inhibit autocrine, or endogenous, Wnt signaling in some cell types and potentiate autocrine signaling in other cell types. In some embodiments, the anti-LRP6 antibodies mediate dimerization of LRP6 and enhance, or potentiate, signaling in the presence of a Wnt isoform that simultaneously binds to LRP6. In some embodiments, the anti-LRP6 antibodies potentiate Wnt signaling by inhibiting binding of Wnt antagonists, such as DKK isoforms and SOST.

The anti-LRP6 antibodies can be used to selectively modulate processes that are activated or inhibited by Wnt isoform induced signaling. Such processes include, for example, cell proliferation, cell fate specification, and stem cell self-renewal in different cancer types, and developmental processes. The anti-LRP6 are useful, e.g., for the treatment of Wnt mediated disorders such as cancer and disorders of the bones or skeletal system and vascular disorders. Examples of cancers that can be treated using anti-LRP6 antibodies include small-cell lung cancer, non-small cell lung cancer, hepatocellular cancer, gastrointestinal cancer, pancreatic cancer, ovarian cancer, liver cancer, bladder cancer, hepatoma, breast cancer, colon cancer, colorectal cancer, endometrial or uterine carcinoma, salivary gland carcinoma, kidney cancer (including renal cell carcinoma), liver cancer, prostate cancer. Examples of skeletal or bone disorders that can be treated using anti-LRP6 antibodies include osteoporosis, osteoarthritis, bone fractures, and bone lesions. Examples of vascular disorders that can be treated using anti-LRP6 antbodies include retinal vascular diseases such as Norrie disease, osteoporosis-pseudoglioma syndrome (OPPG), familial exudative vitreoretinopathy (FEVR), retinopathy of prematurity (ROP), diabetic retinopathy, age-related macular degeneration, retinopathy of prematurity, Coats' disease and Coats' like reaction, and retinal artery or vein occlusion, and myocardial-related conditions, such as myocardial infarction and ischemic heart disease.

Accordingly, one aspect of the invention provides for an antibody that binds to LRP6, wherein the antibody inhibits signaling induced by a Wnt isoform and potentiates signaling induced by another Wnt isoform. In one embodiment, the antibody inhibits signaling by Wnt3 and/or Wnt3a. In one embodiment, the antibody potentiates signaling by Wnt 1, 2, 2b, 4, 6, 7a, 7b, 8a, 9a, 9b, 10a, and/or 10b. In one embodiment, the antibody inhibits signaling by Wnt3 and/or Wnt3a and potentiates signaling by Wnt 1, 2, 2b, 4, 6, 7a, 7b, 8a, 9a, 9b, 10a, and/or 10b. In one embodiment, the antibody inhibits signaling by Wnt3 and Wnt3a and potentiates signaling by Wnt 1, 2, 2b, 4, 6, 7a, 7b, 8a, 9a, 9b, 10a, and 10b. In one embodiment, the anti-LRP6 antibody binds to the E3-E4 region (first and second beta-propellers) of LRP6.

In another embodiment, the antibody inhibits signaling by Wnt 1, 2, 2b, 6, 8a, 9a, 9b, and/or 10b. In one embodiment, the antibody potentiates signaling by Wnt3 and/or Wnt3a. In one embodiment, the antibody inhibits signaling by Wnt 1, 2, 2b, 6, 8a, 9a, 9b, and/or 10b and potentiates signaling by Wnt3 and/or Wnt3a. In one embodiment, the antibody inhibits signaling by Wnt 1, 2, 2b, 6, 8a, 9a, 9b, and/or 10b and potentiates signaling by Wnt3 and/or Wnt3a. In one embodiment, the anti-LRP6 antibody binds to the E1-E2 region (third and fourth beta-propellers) of LRP6.

Another aspect of the invention provides for multispecific anti-LRP6 antibodies. As shown in the Examples, the multispecific antibodies, in some embodiments, have the benefit of inhibiting all three classes of Wnt isoforms. In one embodiment, the anti-LRP6 antibody is a multispecific antibody capable of binding two or more different regions or epitopes of LRP6. In one embodiment, the multispecific antibody is a bispecific antibody capable of specifically binding to two different regions of LRP6. In one embodiment, the bispecific antibody binds to the E1-E2 region of LRP6 and binds to the E3-E4 region of LRP6. In one embodiment, the multispecific antibody inhibits signaling induced by a Wnt isoform selected from the group consisting of Wnt3 and Wnt3a and inhibits signaling induced by a Wnt isoform selected from the group consisting of Wnt 1, 2, 2b, 6, 8a, 9a, 9b, and 10b. In one embodiment, the multispecific antibody inhibits signaling induced by a Wnt isoform selected from the group consisting of Wnt3 and Wnt3a and inhibits signaling induced by a Wnt isoform selected from the group consisting of Wnt 1, 2, 2b, 6, 8a, 9a, 9b, and 10b and further inhibits signaling induced by a Wnt isoform selected from the group consisting of Wnt 4, 7a, 7b, and 10a. In one embodiment, the multispecific antibody inhibits Wnt signaling induced by the combination of Wnt1 and Wnt3a. In one embodiment, the multispecific antibody inhibits autocrine Wnt signaling.

In certain embodiments, the multispecific antibody is a bispecific antibody that inhibits signaling induced by a Wnt isoform selected from the group consisting of Wnt3 and Wnt3a and inhibits signaling induced by a Wnt isoform selected from the group consisting of Wnt 1, 2, 2b, 6, 8a, 9a, 9b, and 10b. In certain embodiments, the multispecific antibody is a bispecific antibody that inhibits signaling induced by a Wnt isoform selected from the group consisting of Wnt3 and Wnt3a and inhibits signaling induced by a Wnt isoform selected from the group consisting of Wnt 1, 2, 2b, 6, 8a, 9a, 9b, and 10b and further inhibits signaling induced by a Wnt isoform selected from the group consisting of Wnt 4, 7a, 7b, and 10a. In certain embodiments, the multispecific antibody is a bispecific antibody that inhibits signaling induced by the combination of Wnt1 and Wnt3a. In one embodiment, the multispecific antibody is a bispecific antibody that inhibits signaling induced by the combination of Wnt1 and Wnt3a more effectively than a combination of monospecific antibodies that have the same specificities as the bispecific antibody.

In certain embodiments, the multispecific antibody is a bispecific antibody that inhibits autocrine Wnt signaling more effectively than a combination of monospecific antibodies that have the same specificities as the bispecific antibody.

In certain embodiments, the anti-LRP6 antibody or multispecific anti-LRP6 antibody inhibits Wnt signaling by at least about 10%, 20%, 30%, 40%, 50%, 60%, 70%, 80%, 90%, or more Inhibition of Wnt signaling can be determined using assays known in the art and described herein. For example, inhibition of Wnt signaling can be determined using a Wnt reporter assay, such as the Wnt luciferase reporter assay described in the Examples.

Inhibition of Wnt signaling can also be determined by monitoring expression of Wnt target genes, such as APCDD1, AXIN2, GAD1, LEFTY2, and SAX1, as described in the Examples.

In certain embodiments, the anti-LRP6 antibody or multispecific anti-LRP6 antibody inhibits expression of Wnt target genes, such as APCDD1, AXIN2, GAD1, LEFTY2, and SAX1 by at least about 10%, 20%, 30%, 40%, 50%, 60%, 70%, 80%, or 90%. In one embodiment, expression of the Wnt target genes is determined using a gene expression assay, such as PCR, including qPCR.

Another aspect of the invention provides for antibodies that bind to LRP6 and compete for binding with any of the anti-LRP6 antibodies described herein. Another aspect of the invention provides for antibodies that bind to the same epitope on LRP6 as any of the anti-LRP6 antibodies described herein.

A. Exemplary Anti-LRP6 Antibodies

One aspect of the invention provides for an anti-LRP6 antibody which is a monoclonal antibody, including a chimeric, humanized or human antibody. In one embodiment, an anti-LRP6 antibody is generated using phage libraries. In one embodiment, an anti-LRP6 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In one embodiment, the anti-LRP6 antibody comprises a heavy chain sequence comprising an amino acid sequence of Table 2. In one embodiment, the anti-LRP6 antibody comprises a light chain sequence comprising an amino acid sequence of Table 2. In one embodiment, the anti-LRP6 antibody comprises a heavy chain sequence and a light chain sequence comprising an amino acid sequence of Table 2.

In one embodiment, the anti-LRP6 antibody comprises a heavy chain sequence comprising the amino acid sequence of SEQ ID NO: 1. In one embodiment, the anti-LRP6 antibody comprises a light chain sequence comprising the amino acid sequence of SEQ ID NO: 2. In one embodiment, the anti-LRP6 antibody comprises a heavy chain sequence comprising the amino acid sequence of SEQ ID NO: 1 and a light chain sequence comprising the amino acid sequence of SEQ ID NO: 2.

In one embodiment, the anti-LRP6 antibody comprises a heavy chain sequence comprising the amino acid sequence of SEQ ID NO: 3. In one embodiment, the anti-LRP6 antibody comprises a light chain sequence comprising the amino acid sequence of SEQ ID NO: 4. In one embodiment, the anti-LRP6 antibody comprises a heavy chain sequence comprising the amino acid sequence of SEQ ID NO: 3 and a light chain sequence comprising the amino acid sequence of SEQ ID NO: 4.

In one embodiment, the anti-LRP6 antibody comprises a heavy chain sequence comprising the amino acid sequence of SEQ ID NO: 5. In one embodiment, the anti-LRP6 antibody comprises a light chain sequence comprising the amino acid sequence of SEQ ID NO: 6. In one embodiment, the anti-LRP6 antibody comprises a heavy chain sequence comprising the amino acid sequence of SEQ ID NO: 5 and a light chain sequence comprising the amino acid sequence of SEQ ID NO: 6.

In one embodiment, the anti-LRP6 antibody comprises a heavy chain sequence comprising the amino acid sequence of SEQ ID NO: 7. In one embodiment, the anti-LRP6 antibody comprises a light chain sequence comprising the amino acid sequence of SEQ ID NO: 8. In one embodiment, the anti-LRP6 antibody comprises a heavy chain sequence comprising the amino acid sequence of SEQ ID NO: 7 and a light chain sequence comprising the amino acid sequence of SEQ ID NO: 8.

In one embodiment, the anti-LRP6 antibody comprises a heavy chain variable domain (VH) from the amino sequences of Table 3. In one embodiment, the anti-LRP6 antibody comprises a light chain variable domain (VL) from the amino sequences of Table 3. In one embodiment, the anti-LRP6 antibody comprises a VH and a VL from the amino sequences of Table 3.

In one embodiment, the anti-LRP6 antibody comprises the heavy chain variable domain (VH) from the heavy chain of the amino sequence of SEQ ID NO: 1. In one embodiment, the anti-LRP6 antibody comprises the light chain variable domain (VL) from the light chain sequence of the amino acid sequence of SEQ ID NO: 2. In one embodiment, the anti-LRP6 antibody comprises the VH from the heavy chain of the amino sequence of SEQ ID NO: 1 and the VL from the light chain sequence of the amino acid sequence of SEQ ID NO: 2.

In one embodiment, the anti-LRP6 antibody comprises a heavy chain variable domain (VH) comprising the amino sequence of SEQ ID NO: 9. In one embodiment, the anti-LRP6 antibody comprises a light chain variable domain (VL) comprising the amino acid sequence of SEQ ID NO: 10.

In one embodiment, the anti-LRP6 antibody comprises a VH comprising the amino sequence of SEQ ID NO: 9 and a VL comprising the amino sequence of SEQ ID NO: 10.

In one embodiment, the anti-LRP6 antibody comprises the heavy chain variable domain (VH) from the heavy chain of the amino sequence of SEQ ID NO: 3. In one embodiment, the anti-LRP6 antibody comprises the light chain variable domain (VL) from the light chain sequence of the amino acid sequence of SEQ ID NO: 4. In one embodiment, the anti-LRP6 antibody comprises the VH from the heavy chain of the amino sequence of SEQ ID NO: 3 and the VL from the light chain sequence of the amino acid sequence of SEQ ID NO: 4.

In one embodiment, the anti-LRP6 antibody comprises a heavy chain variable domain (VH) comprising the amino sequence of SEQ ID NO: 11. In one embodiment, the anti-LRP6 antibody comprises a light chain variable domain (VL) comprising the amino acid sequence of SEQ ID NO: 12. In one embodiment, the anti-LRP6 antibody comprises a VH comprising the amino sequence of SEQ ID NO: 11 and a VL comprising the amino sequence of SEQ ID NO: 12.

In one embodiment, the anti-LRP6 antibody comprises the heavy chain variable domain (VH) from the heavy chain of the amino sequence of SEQ ID NO: 5. In one embodiment, the anti-LRP6 antibody comprises the light chain variable domain (VL) from the light chain sequence of the amino acid sequence of SEQ ID NO: 6. In one embodiment, the anti-LRP6 antibody comprises the VH from the heavy chain of the amino sequence of SEQ ID NO: 5 and the VL from the light chain sequence of the amino acid sequence of SEQ ID NO: 6.

In one embodiment, the anti-LRP6 antibody comprises a heavy chain variable domain (VH) comprising the amino sequence of SEQ ID NO: 13. In one embodiment, the anti-LRP6 antibody comprises a light chain variable domain (VL) comprising the amino acid sequence of SEQ ID NO: 14. In one embodiment, the anti-LRP6 antibody comprises a VH comprising the amino sequence of SEQ ID NO: 13 and a VL comprising the amino acid sequence of SEQ ID NO: 14.

In one embodiment, the anti-LRP6 antibody comprises the heavy chain variable domain (VH) from the heavy chain of the amino sequence of SEQ ID NO: 7. In one embodiment, the anti-LRP6 antibody comprises the light chain variable domain (VL) from the light chain sequence of the amino acid sequence of SEQ ID NO: 8. In one embodiment, the anti-LRP6 antibody comprises the VH from the heavy chain of the amino sequence of SEQ ID NO: 7 and the VL from the light chain sequence of the amino acid sequence of SEQ ID NO: 8.

In one embodiment, the anti-LRP6 antibody comprises a heavy chain variable domain (VH) comprising the amino sequence of SEQ ID NO: 15. In one embodiment, the anti-LRP6 antibody comprises a light chain variable domain (VL) comprising the amino acid sequence of SEQ ID NO: 16. In one embodiment, the anti-LRP6 antibody comprises a VH comprising the amino sequence of SEQ ID NO: 15 and a VL comprising the amino acid sequence of SEQ ID NO: 16.

Another aspect of the invention provides for a multispecific anti-LRP6 antibody. In one embodiment, the multispecific antibody comprises a heavy chain comprising the amino acid sequence of at least one of SEQ ID NO: 1, SEQ ID NO: 3, SEQ ID NO: 5, or SEQ ID NO: 7. In one embodiment, the multispecific antibody comprises a heavy chain comprising the amino acid sequence of at least two of SEQ ID NO: 1, SEQ ID NO: 3, SEQ ID NO: 5, or SEQ ID NO: 7. In one embodiment, the multispecific antibody is a bispecific antibody which comprises a heavy chain comprising the amino acid sequence of at least one of SEQ ID NO: 1, SEQ ID NO: 3, SEQ ID NO: 5, or SEQ ID NO: 7. In one embodiment, the bispecific antibody comprises a first heavy chain comprising the amino acid sequence of SEQ ID NO: 1 and a second heavy chain comprising the amino acid sequence of SEQ ID NO: 7. In one embodiment, the bispecific antibody comprises a first heavy chain comprising the amino acid sequence of SEQ ID NO: 3 and a second heavy chain comprising the amino acid sequence of SEQ ID NO: 7. In one embodiment, the bispecific antibody comprises a first heavy chain comprising the amino acid sequence of SEQ ID NO: 5 and a second heavy chain comprising the amino acid sequence of SEQ ID NO: 7.

In one embodiment, the multispecific anti-LRP6 antibody comprises the VH from the heavy chain of the amino sequence of at least one of SEQ ID NO: 1, SEQ ID NO: 3, SEQ ID NO: 5, or SEQ ID NO: 7. In one embodiment, the multispecific antibody comprises the VH from the heavy chain of the amino sequence of at least two of SEQ ID NO: 1, SEQ ID NO: 3, SEQ ID NO: 5, or SEQ ID NO: 7. In one embodiment, the multispecific antibody is a bispecific antibody which comprises the VH from the heavy chain of the amino sequence of SEQ ID NO: 1, SEQ ID NO: 3, SEQ ID NO: 5, or SEQ ID NO: 7. In one embodiment, the bispecific antibody comprises the VH from the heavy chain of the amino sequence of SEQ ID NO: 1 and comprises the VH from the heavy chain of the amino sequence of SEQ ID NO: 7. In one embodiment, the bispecific antibody comprises the VH from the heavy chain of the amino sequence of SEQ ID NO: 3 and comprises the VH from the heavy chain of the amino sequence of SEQ ID NO: 7. In one embodiment, the bispecific antibody comprises the VH from the heavy chain of the amino sequence of SEQ ID NO: 5 and comprises the VH from the heavy chain of the amino sequence of SEQ ID NO: 7.

In one embodiment, the multispecific anti-LRP6 antibody comprises a VH comprising the amino sequence of at least one of SEQ ID NO: 9, SEQ ID NO: 11, SEQ ID NO: 13, or SEQ ID NO: 15. In one embodiment, the multispecific antibody comprises a VH comprising the amino sequence of at least two of SEQ ID NO: 9, SEQ ID NO: 11, SEQ ID NO: 13, or SEQ ID NO: 15. In one embodiment, the multispecific antibody is a bispecific antibody which comprises a VH comprising the amino sequence of SEQ ID NO: 9, SEQ ID NO: 11, SEQ ID NO: 13, or SEQ ID NO: 15. In one embodiment, the bispecific antibody comprises a first VH comprising the amino sequence of SEQ ID NO: 9 and a second VH comprising the amino sequence of SEQ ID NO: 15. In one embodiment, the bispecific antibody comprises a first VH comprising the amino sequence of SEQ ID NO: 11 and a second VH comprising the amino sequence of SEQ ID NO: 15. In one embodiment, the bispecific antibody comprises a first VH comprising the amino sequence of SEQ ID NO: 13 and a second VH comprising the amino sequence of SEQ ID NO: 15.

In one embodiment, the anti-LRP6 antibody comprises at least one, two, three, four, five, or six HVRs selected from (a) HVR-H1 from the HVR-H1 amino acid sequences of Table 4; (b) HVR-H2 from the HVR-H2 amino acid sequences of Table 4; (c) HVR-H3 from the HVR-H3 amino acid sequences of Table 4; (d) HVR-L1 from the HVR-L1 amino acid sequences of Table 4; (e) HVR-L2 from the HVR-L2 amino acid sequences of Table 4; and (f) HVR-L3 from the HVR-L3 amino acid sequences of Table 4.

In one embodiment, the anti-LRP6 antibody comprises a VH comprising at least one, two, three, four, five, or six HVRs selected from (a) HVR-H1 of the heavy chain of SEQ ID NO: 1; (b) HVR-H2 of the heavy chain of SEQ ID NO: 1; (c) HVR-H3 of the heavy chain of SEQ ID NO: 1; (d) HVR-L1 of the light chain of SEQ ID NO: 2; (e) HVR-L2 of the light chain of SEQ ID NO: 2; and (f) HVR-L3 of the light chain of SEQ ID NO: 2.

In one embodiment, the anti-LRP6 antibody comprises at least one, at least two, or all three VH HVR sequences selected from (a) HVR-H1 of the heavy chain of SEQ ID NO: 1; (b) HVR-H2 of the heavy chain of SEQ ID NO: 1; (c) HVR-H3 of the heavy chain of SEQ ID NO: 1. In one embodiment, the antibody comprises HVR-H3 of the heavy chain of SEQ ID NO: 1. In another embodiment, the antibody comprises HVR-H3 of the heavy chain of SEQ ID NO: 1 and HVR-L3 of the light chain of SEQ ID NO: 2. In a further embodiment, the antibody comprises HVR-H3 of the heavy chain of SEQ ID NO: 1, HVR-L3 of the light chain of SEQ ID NO: 2, and HVR-H2 of the heavy chain of SEQ ID NO: 1. In a further embodiment, the antibody comprises (a) HVR-H1 of the heavy chain of SEQ ID NO: 1; (b) HVR-H2 of the heavy chain of SEQ ID NO: 1; and (c) HVR-H3 of the heavy chain of SEQ ID NO: 1.

In one embodiment, the anti-LRP6 antibody comprises at least one, at least two, or all three VH HVR sequences selected from (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 19. In one embodiment, the antibody comprises HVR-H3 comprising the amino acid sequence of SEQ ID NO: 19. In another embodiment, the antibody comprises HVR-H3 comprising the amino acid sequence of SEQ ID NO: 19 and HVR-L3 comprising the amino acid sequence of SEQ ID NO: 27. In a further embodiment, the antibody comprises HVR-H3 comprising the amino acid sequence of SEQ ID NO: 19, HVR-L3 comprising the amino acid sequence of SEQ ID NO: 27, and HVR-H2 comprising the amino acid sequence of SEQ ID NO: 18. In a further embodiment, the antibody comprises (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 19.

In one embodiment, the anti-LRP6 antibody comprises at least one, at least two, or all three VL HVR sequences selected from (a) HVR-L1 of the light chain of SEQ ID NO: 2; (b) HVR-L2 of the light chain of SEQ ID NO: 2; and (c) HVR-L3 of the light chain of SEQ ID NO: 2. In one embodiment, the antibody comprises (a) HVR-L1 of the light chain of SEQ ID NO: 2; (b) HVR-L2 of the light chain of SEQ ID NO: 2; and (c) HVR-L3 of the light chain of SEQ ID NO: 2.

In one embodiment, the anti-LRP6 antibody comprises (a) a VH domain comprising at least one, at least two, or all three VH HVR sequences selected from (i) HVR-H1 of the heavy chain of SEQ ID NO: 1, (ii) HVR-H2 of the heavy chain of SEQ ID NO: 1, and (iii) HVR-H3 of the heavy chain of SEQ ID NO: 1; and (b) a VL domain comprising at least one, at least two, or all three VL HVR sequences selected from (i) HVR-L1 of the light chain of SEQ ID NO: 2, (ii) HVR-L2 of the light chain of SEQ ID NO: 2, and (c) HVR-L3 of the light chain of SEQ ID NO: 2.

In one embodiment, the anti-LRP6 antibody comprises (a) a VH domain comprising at least one, at least two, or all three VH HVR sequences selected from (i) HVR-H1 comprising the amino acid sequence of SEQ ID NO: 17, (ii) HVR-H2 comprising the amino acid sequence of SEQ ID NO: 18, and (iii) HVR-H3 comprising the amino acid sequence of SEQ ID NO: 19; and (b) a VL domain comprising at least one, at least two, or all three VL HVR sequences selected from (i) HVR-L1 comprising the amino acid sequence of SEQ ID NO: 25, (ii) HVR-L2 comprising the amino acid sequence of SEQ ID NO: 26, and (c) HVR-L3 comprising the amino acid sequence of SEQ ID NO: 27.

In another aspect, the invention provides an antibody comprising (a) HVR-H1 of the heavy chain of SEQ ID NO: 1; (b) HVR-H2 of the heavy chain of SEQ ID NO: 1; (c) HVR-H3 of the heavy chain of SEQ ID NO: 1; (d) HVR-L1 of the light chain of SEQ ID NO: 2; (e) HVR-L2 of the light chain of SEQ ID NO: 2; and (f) HVR-L3 of the light chain of SEQ ID NO: 2.

In another aspect, the invention provides an antibody comprising (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 19; (d) HVR-L1 comprising the amino acid sequence of SEQ ID NO: 25; (e) HVR-L2 comprising the amino acid sequence of SEQ ID NO: 26; and (f) HVR-L3 comprising the amino acid sequence of SEQ ID NO: 27.

In one embodiment, the anti-LRP6 antibody comprises at least one, two, three, four, five, or six HVRs selected from (a) HVR-H1 of the heavy chain of SEQ ID NO: 3; (b) HVR-H2 of the heavy chain of SEQ ID NO: 3; (c) HVR-H3 of the heavy chain of SEQ ID NO: 3; (d) HVR-L1 of the light chain of SEQ ID NO: 4; (e) HVR-L2 of the light chain of SEQ ID NO: 4; and (f) HVR-L3 of the light chain of SEQ ID NO: 4.

In one embodiment, the anti-LRP6 antibody comprises at least one, at least two, or all three VH HVR sequences selected from (a) HVR-H1 of the heavy chain of SEQ ID NO: 3; (b) HVR-H2 of the heavy chain of SEQ ID NO: 3; (c) HVR-H3 of the heavy chain of SEQ ID NO: 3. In one embodiment, the antibody comprises HVR-H3 of the heavy chain of SEQ ID NO: 3. In another embodiment, the antibody comprises HVR-H3 of the heavy chain of SEQ ID NO: 3 and HVR-L3 of the light chain of SEQ ID NO: 4. In a further embodiment, the antibody comprises HVR-H3 of the heavy chain of SEQ ID NO: 3, HVR-L3 of the light chain of SEQ ID NO: 4, and HVR-H2 of the heavy chain of SEQ ID NO: 3. In a further embodiment, the antibody comprises (a) HVR-H1 of the heavy chain of SEQ ID NO: 3; (b) HVR-H2 of the heavy chain of SEQ ID NO: 3; and (c) HVR-H3 of the heavy chain of SEQ ID NO: 3.

In one embodiment, the anti-LRP6 antibody comprises at least one, at least two, or all three VH HVR sequences selected from (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 21. In one embodiment, the antibody comprises a HVR-H3 comprising the amino acid sequence of SEQ ID NO: 21. In another embodiment, the antibody comprises a HVR-H3 of the heavy chain of SEQ ID NO: 21 and HVR-L3 comprising the amino acid sequence of SEQ ID NO: 28. In a further embodiment, the antibody comprises a HVR-H3 comprising the amino acid sequence of SEQ ID NO: 21, a HVR-L3 comprising the amino acid sequence of SEQ ID NO: 28, and a HVR-H2 comprising the amino acid sequence of SEQ ID NO: 18. In a further embodiment, the antibody comprises a (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 21.

In one embodiment, the anti-LRP6 antibody comprises at least one, at least two, or all three VL HVR sequences selected from (a) HVR-L1 of the light chain of SEQ ID NO: 4; (b) HVR-L2 of the light chain of SEQ ID NO: 4; and (c) HVR-L3 of the light chain of SEQ ID NO: 4. In one embodiment, the antibody comprises (a) HVR-L1 of the light chain of SEQ ID NO: 4; (b) HVR-L2 of the light chain of SEQ ID NO: 4; and (c) HVR-L3 of the light chain of SEQ ID NO: 4.

In one embodiment, the anti-LRP6 antibody comprises at least one, at least two, or all three VL HVR sequences selected from (a) HVR-L1 comprising the amino acid sequence of SEQ ID NO: 25; (b) HVR-L2 comprising the amino acid sequence of SEQ ID NO: 26; and (c) HVR-L3 comprising the amino acid sequence of SEQ ID NO: 28. In one embodiment, the antibody comprises (a) HVR-L1 comprising the amino acid sequence of SEQ ID NO: 25; (b) HVR-L2 comprising the amino acid sequence of SEQ ID NO: 26; and (c) HVR-L3 comprising the amino acid sequence of SEQ ID NO: 28.

In one embodiment, the anti-LRP6 antibody comprises (a) a VH domain comprising at least one, at least two, or all three VH HVR sequences selected from (i) HVR-H1 of the heavy chain of SEQ ID NO: 3, (ii) HVR-H2 of the heavy chain of SEQ ID NO: 3, and (iii) HVR-H3 of the heavy chain of SEQ ID NO: 3; and (b) a VL domain comprising at least one, at least two, or all three VL HVR sequences selected from (i) HVR-L1 of the light chain of SEQ ID NO: 4, (ii) HVR-L2 of the light chain of SEQ ID NO: 4, and (c) HVR-L3 of the light chain of SEQ ID NO: 4.

In one embodiment, the anti-LRP6 antibody comprises (a) a VH domain comprising at least one, at least two, or all three VH HVR sequences selected from a (i) HVR-H1 comprising the amino acid sequence of SEQ ID NO: 17, (ii) HVR-H2 comprising the amino acid sequence of SEQ ID NO: 18, and (iii) HVR-H3 comprising the amino acid sequence of SEQ ID NO: 21; and (b) a VL domain comprising at least one, at least two, or all three VL HVR sequences selected from a (i) HVR-L1 comprising the amino acid sequence of SEQ ID NO:

25, (ii) HVR-L2 comprising the amino acid sequence of SEQ ID NO: 26, and (c) HVR-L3 comprising the amino acid sequence of SEQ ID NO: 28.

In another aspect, the invention provides an antibody comprising (a) HVR-H1 of the heavy chain of SEQ ID NO: 3; (b) HVR-H2 of the heavy chain of SEQ ID NO: 3; (c) HVR-H3 of the heavy chain of SEQ ID NO: 3; (d) HVR-L1 of the light chain of SEQ ID NO: 4; (e) HVR-L2 of the light chain of SEQ ID NO: 4; and (f) HVR-L3 of the light chain of SEQ ID NO: 4.

In another aspect, the invention provides an antibody comprising a (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 21; (d) HVR-L1 comprising the amino acid sequence of SEQ ID NO: 25; (e) HVR-L2 comprising the amino acid sequence of SEQ ID NO: 26; and (f) HVR-L3 comprising the amino acid sequence of SEQ ID NO: 28.

In one embodiment, the anti-LRP6 antibody comprises at least one, two, three, four, five, or six HVRs selected from (a) HVR-H1 of the heavy chain of SEQ ID NO: 5; (b) HVR-H2 of the heavy chain of SEQ ID NO: 5; (c) HVR-H3 of the heavy chain of SEQ ID NO: 5; (d) HVR-L1 of the light chain of SEQ ID NO: 6; (e) HVR-L2 of the light chain of SEQ ID NO: 6; and (f) HVR-L3 of the light chain of SEQ ID NO: 6.

In one embodiment, the anti-LRP6 antibody comprises at least one, at least two, or all three VH HVR sequences selected from (a) HVR-H1 of the heavy chain of SEQ ID NO: 5; (b) HVR-H2 of the heavy chain of SEQ ID NO: 5; (c) HVR-H3 of the heavy chain of SEQ ID NO: 5. In one embodiment, the antibody comprises HVR-H3 of the heavy chain of SEQ ID NO: 5. In another embodiment, the antibody comprises HVR-H3 of the heavy chain of SEQ ID NO: 5 and HVR-L3 of the light chain of SEQ ID NO: 6. In a further embodiment, the antibody comprises HVR-H3 of the heavy chain of SEQ ID NO: 5, HVR-L3 of the light chain of SEQ ID NO: 6, and HVR-H2 of the heavy chain of SEQ ID NO: 5. In a further embodiment, the antibody comprises (a) HVR-H1 of the heavy chain of SEQ ID NO: 5; (b) HVR-H2 of the heavy chain of SEQ ID NO: 5; and (c) HVR-H3 of the heavy chain of SEQ ID NO: 5.

In one embodiment, the anti-LRP6 antibody comprises at least one, at least two, or all three VH HVR sequences selected from a (a) HVR-H1 comprising the amino acid sequence of SEQ ID NO: 20; (b) HVR-H2 comprising the amino acid sequence of SEQ ID NO: 18; (c) HVR-H3 comprising the amino acid sequence of SEQ ID NO: 19. In one embodiment, the antibody comprises a HVR-H3 comprising the amino acid sequence of SEQ ID NO: 19. In another embodiment, the antibody comprises a HVR-H3 comprising the amino acid sequence of SEQ ID NO: 19 and a HVR-L3 comprising the amino acid sequence of SEQ ID NO: 27. In a further embodiment, the antibody comprises a HVR-H3 comprising the amino acid sequence of SEQ ID NO: 19, HVR-L3 comprising the amino acid sequence of SEQ ID NO: 27, and HVR-H2 comprising the amino acid sequence of SEQ ID NO: 18. In a further embodiment, the antibody comprises a (a) HVR-H1 comprising the amino acid sequence of SEQ ID NO: 20; (b) HVR-H2 comprising the amino acid sequence of SEQ ID NO: 18; and (c) HVR-H3 comprising the amino acid sequence of SEQ ID NO: 19.

In one embodiment, the anti-LRP6 antibody comprises at least one, at least two, or all three VL HVR sequences selected from (a) HVR-L1 of the light chain of SEQ ID NO: 6; (b) HVR-L2 of the light chain of SEQ ID NO: 6; and (c) HVR-L3 of the light chain of SEQ ID NO: 6. In one embodiment, the antibody comprises (a) HVR-L1 of the light chain of SEQ ID NO: 6; (b) HVR-L2 of the light chain of SEQ ID NO: 6; and (c) HVR-L3 of the light chain of SEQ ID NO: 6.

In one embodiment, the anti-LRP6 antibody comprises (a) a VH domain comprising at least one, at least two, or all three VH HVR sequences selected from (i) HVR-H1 of the heavy chain of SEQ ID NO: 5, (ii) HVR-H2 of the heavy chain of SEQ ID NO: 5, and (iii) HVR-H3 of the heavy chain of SEQ ID NO: 5; and (b) a VL domain comprising at least one, at least two, or all three VL HVR sequences selected from (i) HVR-L1 of the light chain of SEQ ID NO: 6, (ii) HVR-L2 of the light chain of SEQ ID NO: 6, and (c) HVR-L3 of the light chain of SEQ ID NO: 6.

In one embodiment, the anti-LRP6 antibody comprises (a) a VH domain comprising at least one, at least two, or all three VH HVR sequences selected from a (i) HVR-H1 comprising the amino acid sequence of SEQ ID NO: 20, (ii) HVR-H2 comprising the amino acid sequence of SEQ ID NO: 18, and (iii) HVR-H3 comprising the amino acid sequence of SEQ ID NO: 19; and (b) a VL domain comprising at least one, at least two, or all three VL HVR sequences selected from a (i) HVR-L1 comprising the amino acid sequence of SEQ ID NO: 25, (ii) HVR-L2 comprising the amino acid sequence of SEQ ID NO: 26, and (c) HVR-L3 comprising the amino acid sequence of SEQ ID NO: 27.

In another aspect, the invention provides an antibody comprising (a) HVR-H1 of the heavy chain of SEQ ID NO: 5; (b) HVR-H2 of the heavy chain of SEQ ID NO: 5; (c) HVR-H3 of the heavy chain of SEQ ID NO: 5; (d) HVR-L1 of the light chain of SEQ ID NO: 6; (e) HVR-L2 of the light chain of SEQ ID NO: 6; and (f) HVR-L3 of the light chain of SEQ ID NO: 6.

In another aspect, the invention provides an antibody comprising a (a) HVR-H1 comprising the amino acid sequence of SEQ ID NO: 20; (b) HVR-H2 comprising the amino acid sequence of SEQ ID NO: 18; (c) HVR-H3 comprising the amino acid sequence of SEQ ID NO: 19; (d) HVR-L1 comprising the amino acid sequence of SEQ ID NO: 25; (e) HVR-L2 comprising the amino acid sequence of SEQ ID NO: 26; and (f) HVR-L3 comprising the amino acid sequence of SEQ ID NO: 27.

In one embodiment, the anti-LRP6 antibody comprises at least one, two, three, four, five, or six HVRs selected from (a) HVR-H1 of the heavy chain of SEQ ID NO: 7; (b) HVR-H2 of the heavy chain of SEQ ID NO: 7; (c) HVR-H3 of the heavy chain of SEQ ID NO: 7; (d) HVR-L1 of the light chain of SEQ ID NO: 8; (e) HVR-L2 of the light chain of SEQ ID NO: 8; and (f) HVR-L3 of the light chain of SEQ ID NO: 8.

In one embodiment, the anti-LRP6 antibody comprises at least one, at least two, or all three VH HVR sequences selected from (a) HVR-H1 of the heavy chain of SEQ ID NO: 7; (b) HVR-H2 of the heavy chain of SEQ ID NO: 7; (c) HVR-H3 of the heavy chain of SEQ ID NO: 7. In one embodiment, the antibody comprises HVR-H3 of the heavy chain of SEQ ID NO: 7. In another embodiment, the antibody comprises HVR-H3 of the heavy chain of SEQ ID NO: 7 and HVR-L3 of the light chain of SEQ ID NO: 8. In a further embodiment, the antibody comprises HVR-H3 of the heavy chain of SEQ ID NO: 7, HVR-L3 of the light chain of SEQ ID NO: 8, and HVR-H2 of the heavy chain of SEQ ID NO: 7. In a further embodiment, the antibody comprises (a) HVR-H1 of the heavy chain of SEQ ID NO: 7; (b) HVR-H2 of the heavy chain of SEQ ID NO: 7; and (c) HVR-H3 of the heavy chain of SEQ ID NO: 7.

In one embodiment, the anti-LRP6 antibody comprises at least one, at least two, or all three VH HVR sequences selected from a (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24. In one embodiment, the antibody comprises a HVR-H3 comprising the amino acid sequence of SEQ ID NO: 24. In another embodiment, the antibody comprises a HVR-H3 comprising the amino acid sequence of SEQ ID NO: 24 and a HVR-L3 comprising the amino acid sequence of SEQ ID NO: 27. In a further embodiment, the antibody comprises a HVR-H3 comprising the amino acid sequence of SEQ ID NO: 24, HVR-L3 comprising the amino acid sequence of SEQ ID NO: 27, and HVR-H2 comprising the amino acid sequence of SEQ ID NO: 23. In a further embodiment, the antibody comprises a (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24.

In one embodiment, the anti-LRP6 antibody comprises at least one, at least two, or all three VL HVR sequences selected from (a) HVR-L1 of the light chain of SEQ ID NO: 8; (b) HVR-L2 of the light chain of SEQ ID NO: 8; and (c) HVR-L3 of the light chain of SEQ ID NO: 8. In one embodiment, the antibody comprises (a) HVR-L1 of the light chain of SEQ ID NO: 8; (b) HVR-L2 of the light chain of SEQ ID NO: 8; and (c) HVR-L3 of the light chain of SEQ ID NO: 8.

In one embodiment, the anti-LRP6 antibody comprises (a) a VH domain comprising at least one, at least two, or all three VH HVR sequences selected from (i) HVR-H1 of the heavy chain of SEQ ID NO: 7, (ii) HVR-H2 of the heavy chain of SEQ ID NO: 7, and (iii) HVR-H3 of the heavy chain of SEQ ID NO: 7; and (b) a VL domain comprising at least one, at least two, or all three VL HVR sequences selected from (i) HVR-L1 of the light chain of SEQ ID NO: 8, (ii) HVR-L2 of the light chain of SEQ ID NO: 8, and (c) HVR-L3 of the light chain of SEQ ID NO: 8.

In one embodiment, the anti-LRP6 antibody comprises (a) a VH domain comprising at least one, at least two, or all three VH HVR sequences selected from a (i) HVR-H1 comprising the amino acid sequence of SEQ ID NO: 22, (ii) HVR-H2 comprising the amino acid sequence of SEQ ID NO: 23, and (iii) HVR-H3 comprising the amino acid sequence of SEQ ID NO: 24; and (b) a VL domain comprising at least one, at least two, or all three VL HVR sequences selected from a (i) HVR-L1 comprising the amino acid sequence of SEQ ID NO: 25, (ii) HVR-L2 comprising the amino acid sequence of SEQ ID NO: 26, and (c) HVR-L3 comprising the amino acid sequence of SEQ ID NO: 27.

In another embodiment, the invention provides an antibody comprising (a) HVR-H1 of the heavy chain of SEQ ID NO: 7; (b) HVR-H2 of the heavy chain of SEQ ID NO: 7; (c) HVR-H3 of the heavy chain of SEQ ID NO: 7; (d) HVR-L1 of the light chain of SEQ ID NO: 8; (e) HVR-L2 of the light chain of SEQ ID NO: 8; and (f) HVR-L3 of the light chain of SEQ ID NO: 8.

In another embodiment, the invention provides an antibody comprising a (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 25; (e) HVR-L2 comprising the amino acid sequence of SEQ ID NO: 26; and (f) HVR-L3 comprising the amino acid sequence of SEQ ID NO: 27.

In one embodiment, the anti-LRP6 antibody is a multispecific anti-LRP6 antibody that comprises a first VH domain comprising at least one, at least two, or all three VH HVR sequences selected from (a) HVR-H1 of the heavy chain of SEQ ID NO: 1; (b) HVR-H2 of the heavy chain of SEQ ID NO: 1; (c) HVR-H3 of the heavy chain of SEQ ID NO: 1 and comprises a second VH domain comprising at least one, at least two, or all three VH HVR sequences selected from (d) HVR-H1 of the heavy chain of SEQ ID NO: 7; (e) HVR-H2 of the heavy chain of SEQ ID NO: 7; (f) HVR-H3 of the heavy chain of SEQ ID NO: 7.

In one embodiment, the anti-LRP6 antibody is a multispecific anti-LRP6 antibody that comprises a first VH domain comprising at least one, at least two, or all three VH HVR sequences selected from a (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 19 and comprises a second VH domain comprising at least one, at least two, or all three VH HVR sequences selected from a (d) HVR-H1 comprising the amino acid sequence of SEQ ID NO: 22; (e) HVR-H2 comprising the amino acid sequence of SEQ ID NO: 23; (f) HVR-H3 comprising the amino acid sequence of SEQ ID NO: 24.

In one embodiment, the anti-LRP6 antibody is a multispecific anti-LRP6 antibody that comprises a first VH domain comprising all three VH HVR sequences from (a) HVR-H1 of the heavy chain of SEQ ID NO: 1; (b) HVR-H2 of the heavy chain of SEQ ID NO: 1; (c) HVR-H3 of the heavy chain of SEQ ID NO: 1 and comprises a second VH domain comprising all three VH HVR sequences from (d) HVR-H1 of the heavy chain of SEQ ID NO: 7; (e) HVR-H2 of the heavy chain of SEQ ID NO: 7; (f) HVR-H3 of the heavy chain of SEQ ID NO: 7.

In one embodiment, the anti-LRP6 antibody is a multispecific anti-LRP6 antibody that comprises a first VH domain comprising all three VH HVR sequences from a (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 19 and comprises a second VH domain comprising all three VH HVR sequences from a (d) HVR-H1 comprising the amino acid sequence of SEQ ID NO: 22; (e) HVR-H2 comprising the amino acid sequence of SEQ ID NO: 23; (f) HVR-H3 comprising the amino acid sequence of SEQ ID NO: 24.

In one embodiment, the anti-LRP6 antibody is a multispecific anti-LRP6 antibody that comprises a first VH domain comprising at least one, at least two, or all three VH HVR sequences selected from (a) HVR-H1 of the heavy chain of SEQ ID NO: 3; (b) HVR-H2 of the heavy chain of SEQ ID NO: 3; (c) HVR-H3 of the heavy chain of SEQ ID NO: 3 and comprises a second VH domain comprising at least one, at least two, or all three VH HVR sequences selected from (d) HVR-H1 of the heavy chain of SEQ ID NO: 7; (e) HVR-H2 of the heavy chain of SEQ ID NO: 7; (f) HVR-H3 of the heavy chain of SEQ ID NO: 7.

In one embodiment, the anti-LRP6 antibody is a multispecific anti-LRP6 antibody that comprises a first VH domain comprising at least one, at least two, or all three VH HVR sequences selected from a (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 21 and comprises a second VH domain comprising at least one, at least two, or all three VH HVR sequences selected from a (d) HVR-H1 comprising the amino acid sequence of SEQ ID NO: 22; (e) HVR-H2 comprising the amino acid sequence of SEQ ID NO: 23; (f) HVR-H3 comprising the amino acid sequence of SEQ ID NO: 24.

In one embodiment, the anti-LRP6 antibody is a multispecific anti-LRP6 antibody that comprises a first VH domain comprising all three VH HVR sequences from (a) HVR-H1 of the heavy chain of SEQ ID NO: 3; (b) HVR-H2 of the heavy chain of SEQ ID NO: 3; (c) HVR-H3 of the heavy chain of SEQ ID NO: 3 and comprises a second VH domain comprising all three VH HVR sequences from (d) HVR-H1 of the heavy chain of SEQ ID NO: 7; (e) HVR-H2 of the heavy chain of SEQ ID NO: 7; (f) HVR-H3 of the heavy chain of SEQ ID NO: 7.

In one embodiment, the anti-LRP6 antibody is a multispecific anti-LRP6 antibody that comprises a first VH domain comprising all three VH HVR sequences from a (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 21 and comprises a second VH domain comprising all three VH HVR sequences from a (d) HVR-H1 comprising the amino acid sequence of SEQ ID NO: 22; (e) HVR-H2 comprising the amino acid sequence of SEQ ID NO: 23; (f) HVR-H3 comprising the amino acid sequence of SEQ ID NO: 24.

In one embodiment, the anti-LRP6 antibody is a multispecific anti-LRP6 antibody that comprises a first VH domain comprising at least one, at least two, or all three VH HVR sequences selected from (a) HVR-H1 of the heavy chain of SEQ ID NO: 5; (b) HVR-H2 of the heavy chain of SEQ ID NO: 5; (c) HVR-H3 of the heavy chain of SEQ ID NO: 5 and comprises a second VH domain comprising at least one, at least two, or all three VH HVR sequences selected from (d) HVR-H1 of the heavy chain of SEQ ID NO: 7; (e) HVR-H2 of the heavy chain of SEQ ID NO: 7; (f) HVR-H3 of the heavy chain of SEQ ID NO: 7.

In one embodiment, the anti-LRP6 antibody is a multispecific anti-LRP6 antibody that comprises a first VH domain comprising at least one, at least two, or all three VH HVR sequences selected from a (a) HVR-H1 comprising the amino acid sequence of SEQ ID NO: 20; (b) HVR-H2 comprising the amino acid sequence of SEQ ID NO: 18; (c) HVR-H3 comprising the amino acid sequence of SEQ ID NO: 19 and comprises a second VH domain comprising at least one, at least two, or all three VH HVR sequences selected from a (d) HVR-H1 comprising the amino acid sequence of SEQ ID NO: 22; (e) HVR-H2 comprising the amino acid sequence of SEQ ID NO: 23; (f) HVR-H3 comprising the amino acid sequence of SEQ ID NO: 24.

In one embodiment, the anti-LRP6 antibody is a multispecific anti-LRP6 antibody that comprises a first VH domain comprising all three VH HVR sequences from (a) HVR-H1 of the heavy chain of SEQ ID NO: 5; (b) HVR-H2 of the heavy chain of SEQ ID NO: 5; (c) HVR-H3 of the heavy chain of SEQ ID NO: 5 and comprises a second VH domain comprising all three VH HVR sequences from (d) HVR-H1 of the heavy chain of SEQ ID NO: 7; (e) HVR-H2 of the heavy chain of SEQ ID NO: 7; (f) HVR-H3 of the heavy chain of SEQ ID NO: 7.

In one embodiment, the anti-LRP6 antibody is a multispecific anti-LRP6 antibody that comprises a first VH domain comprising all three VH HVR sequences from a (a) HVR-H1 comprising the amino acid sequence of SEQ ID NO: 20; (b) HVR-H2 comprising the amino acid sequence of SEQ ID NO: 18; (c) HVR-H3 comprising the amino acid sequence of SEQ ID NO: 19 and comprises a second VH domain comprising all three VH HVR sequences from a (d) HVR-H1 comprising the amino acid sequence of SEQ ID NO: 22; (e) HVR-H2 comprising the amino acid sequence of SEQ ID NO: 23; (f) HVR-H3 comprising the amino acid sequence of SEQ ID NO: 24.

In any of the above embodiments of multispecific anti-LRP6 antibodies, the antibodies further comprises at least one, at least two, or all three VL HVR sequences selected from (a) HVR-L1 of the light chain of SEQ ID NO: 2; (b) HVR-L2 of the light chain of SEQ ID NO: 2; and (c) HVR-L3 of the light chain of SEQ ID NO: 2 or SEQ ID NO: 4. In one embodiment, the antibody comprises (a) HVR-L1 of the light chain of SEQ ID NO: 2; (b) HVR-L2 of the light chain of SEQ ID NO: 2; and (c) HVR-L3 of the light chain of SEQ ID NO: 2. In one embodiment, the antibody comprises (a) HVR-L1 of the light chain of SEQ ID NO: 2; (b) HVR-L2 of the light chain of SEQ ID NO: 2; and (c) HVR-L3 of the light chain of SEQ ID NO: 4.

In any of the above embodiments of multispecific anti-LRP6 antibodies, the antibodies further comprises at least one, at least two, or all three VL HVR sequences selected from a (a) HVR-L1 comprising the amino acids of SEQ ID NO: 25; (b) HVR-L2 comprising the amino acids of SEQ ID NO: 26; and (c) HVR-L3 comprising the amino acids of SEQ ID NO: 27 or SEQ ID NO: 28. In one embodiment, the antibody comprises a (a) HVR-L1 comprising the amino acids of SEQ ID NO: 25; (b) HVR-L2 comprising the amino acids of SEQ ID NO: 26; and (c) HVR-L3 comprising the amino acids of SEQ ID NO: 27. In one embodiment, the antibody comprises (a) HVR-L1 comprising the amino acids of SEQ ID NO: 25; (b) HVR-L2 comprising the amino acids of SEQ ID NO: 26; and (c) HVR-L3 comprising the amino acids of SEQ ID NO: 28.

In one embodiment, the anti-LRP6 antibody or multispecific anti-LRP6 antibody comprises a HVR-H3 comprising the amino acid sequence N $X_1$ $X_2$ K (SEQ ID NO: 41). In one embodiment, the anti-LRP6 antibody or multispecific anti-LRP6 antibody a HVR-H3 comprising the amino acid sequence N $X_1$ $X_2$ KN (SEQ ID NO: 42). In one embodiment, the anti-LRP6 antibody or multispecific anti-LRP6 antibody comprises a HVR-H3 comprising the amino acid sequence N $X_1$ VK (SEQ ID NO: 43). In one embodiment, the anti-LRP6 antibody or multispecific anti-LRP6 antibody comprises a HVR-H3 comprising the amino acid sequence N$X_1$IK (SEQ ID NO: 44). In one embodiment, the anti-LRP6 antibody or multispecific anti-LRP6 antibody comprises a HVR-H3 comprising the amino acid sequence N$X_1$VKN (SEQ ID NO: 45). In one embodiment, the anti-LRP6 antibody or multispecific anti-LRP6 antibody comprises a HVR-H3 comprising the amino acid sequence N$X_{11}$KN (SEQ ID NO: 46). In the above embodiments, $X_1$ is an amino acid and $X_2$ is I or V; or $X_1$ is A, S, F, T, Y, or L and $X_2$ is I or V; or $X_1$ is A, S, F, T, Y, or L and $X_2$ is I; or $X_1$ is A, S, F, T, Y, or L and $X_2$ is V.

In one embodiment, the anti-LRP6 antibody or multispecific anti-LRP6 antibody comprises a HVR-H3 comprising the amino acid sequence NAVK (SEQ ID NO: 47). In one embodiment, the anti-LRP6 antibody or multispecific anti-LRP6 antibody comprises a HVR-H3 comprising the amino acid sequence NAIK (SEQ ID NO: 48). In one embodiment, the anti-LRP6 antibody or multispecific anti-LRP6 antibody comprises a HVR-H3 comprising the amino acid sequence NAVKN (SEQ ID NO: 49). In one embodiment, the anti-LRP6 antibody or multispecific anti-LRP6 antibody comprises a HVR-H3 comprising the amino acid sequence NAIKN (SEQ ID NO: 50).

In any of the above embodiments, an anti-LRP6 antibody is humanized. In one embodiment, an anti-LRP6 antibody comprises HVRs as in any of the above embodiments, and further comprises an acceptor human framework, e.g. a human immunoglobulin framework or a human consensus framework.

In another aspect, an anti-LRP6 antibody comprises a heavy chain variable domain (VH) sequence having at least 90%, 91%, 92%, 93%, 94%, 95%, 96%, 97%, 98%, 99%, or 100% sequence identity to a VH of the heavy chain of the amino acid sequence of SEQ ID NO: 1, SEQ ID NO: 3, SEQ ID NO: 5, or SEQ ID NO: 7. In another aspect, an anti-LRP6 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 9, SEQ ID NO: 11, SEQ ID NO: 13, or SEQ ID NO: 15. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-LRP6 antibody comprising that sequence retains the ability to bind to LRP6. In certain embodiments, a total of 1 to 10 amino acids have been substituted, inserted and/or deleted in the VH of SEQ ID NO: 1, SEQ ID NO: 3, SEQ ID NO: 5, or SEQ ID NO: 7 or in SEQ ID NO: 9, SEQ ID NO: 11, SEQ ID NO: 13, or SEQ ID NO: 15.1.

In another aspect, an anti-LRP6 antibody comprises a heavy chain sequence having at least 90%, 91%, 92%, 93%, 94%, 95%, 96%, 97%, 98%, 99%, or 100% sequence identity to the amino acid sequence of SEQ ID NO: 1, SEQ ID NO: 3, SEQ ID NO: 5, or SEQ ID NO: 7. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-LRP6 antibody comprising that sequence retains the ability to bind to LRP6. In certain embodiments, a total of 1 to 10 amino acids have been substituted, inserted and/or deleted in SEQ ID NO: 1, SEQ ID NO: 3, SEQ ID NO: 5, or SEQ ID NO: 7.

In certain embodiments, substitutions, insertions, or deletions occur in regions outside the HVRs (i.e., in the FRs). Optionally, the anti-LRP6 antibody comprises the heavy chain and/or VH of the heavy chain of SEQ ID NO: 1, SEQ ID NO: 3, SEQ ID NO: 5, or SEQ ID NO: 7, including post-translational modifications of that sequence.

In another aspect, an anti-LRP6 antibody is provided, wherein the antibody comprises a light chain variable domain (VL) having at least 90%, 91%, 92%, 93%, 94%, 95%, 96%, 97%, 98%, 99%, or 100% sequence identity to a VL of the light chain of the amino acid sequence of SEQ ID NO: 2, SEQ ID NO: 4, SEQ ID NO: 6, or SEQ ID NO: 8. In another aspect, an anti-LRP6 antibody is provided, wherein the antibody comprises a light chain variable domain (VL) having at least 90%, 91%, 92%, 93%, 94%, 95%, 96%, 97%, 98%, 99%, or 100% sequence identity the amino acid sequence of SEQ ID NO: 10, SEQ ID NO: 12, SEQ ID NO: 14, or SEQ ID NO: 16. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-LRP6 antibody comprising that sequence retains the ability to bind to LRP6. In certain embodiments, a total of 1 to 10 amino acids have been substituted, inserted and/or deleted in the VL of SEQ ID NO: 2, SEQ ID NO: 4, SEQ ID NO: 6, or SEQ ID NO: 8, or in SEQ ID NO: 10, SEQ ID NO: 12, SEQ ID NO: 14, or SEQ ID NO: 16

In another aspect, an anti-LRP6 antibody is provided, wherein the antibody comprises a light chain having at least 90%, 91%, 92%, 93%, 94%, 95%, 96%, 97%, 98%, 99%, or 100% sequence identity to the amino acid sequence of SEQ ID NO: 2, SEQ ID NO: 4, SEQ ID NO: 6, or SEQ ID NO: 8. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-LRP6 antibody comprising that sequence retains the ability to bind to LRP6. In certain embodiments, a total of I to 10 amino acids have been substituted, inserted and/or deleted in SEQ ID NO: 2, SEQ ID NO: 4, SEQ ID NO: 6, or SEQ ID NO: 8.

In certain embodiments, the substitutions, insertions, or deletions occur in regions outside the HVRs (i.e., in the FRs). Optionally, the anti-LRP6 antibody comprises the light chain and/or VL sequence in SEQ ID NO: 2, SEQ ID NO: 4, SEQ ID NO: 6, or SEQ ID NO: 8, including post-translational modifications of that sequence.

In another aspect, an anti-LRP6 antibody is provided, wherein the antibody comprises a VH as in any of the embodiments provided above, and a VL as in any of the embodiments provided above.

In a further aspect, the invention provides an antibody that binds to the same epitope as an anti-LRP6 antibody provided herein. For example, in certain embodiments, an antibody is provided that binds to the same epitope as an anti-LRP6 antibody selected from an anti-LRP6 antibody comprising a VH sequence of SEQ ID NO: 9 and a VL sequence of SEQ ID NO:10, or a VH sequence of SEQ ID NO: 11 and a VL sequence of SEQ ID NO:12, or a VH sequence of SEQ ID NO: 13 and a VL sequence of SEQ ID NO:14, or a VH sequence of SEQ ID NO: 15 and a VL sequence of SEQ ID NO: 16. In one embodiment, the anti-LRP6 antibody binds to an epitope that is comprised of amino acid residues in the E1-E2 region of LRP6. In one embodiment, the anti-LRP6 antibody binds to an epitope that is comprised of amino acid residues in the E3-E4 region of LRP6. In one embodiment, the anti-LRP6 antibody is a bispecific antibody that binds to an epitope that is comprised of amino acid residues present in the E1-E2 region of LRP6 and binds to an epitope that is comprised of amino acid residues present in the E3-E4 region of LRP6.

In one embodiment, the anti-LRP6 antibody binds to a conformational epitope that includes residues R28, E51, D52, V70, S71, E73, L95, S96, D98, E115, R141, and N185 of LRP6. In one embodiment, the anti-LRP6 antibody binds to a conformational epitope that includes residues R28, E51, D52, V70, S71, E73, L95, S96, D98, E115, R141, N185, R29, W188, $K_{202}$, P225, H226, S243, and F266 of LRP6.

In one embodiment, the anti-LRP6 antibody interacts with at least one, at least two, at least three, at least four, at least five, at least six, at least seven, at least eight, at least nine, at least ten, at least eleven, or all of the amino acid residues R28, E51, D52, V70, S71, E73, L95, S96, D98, E115, R141, and N185 of the E1 β-propeller of LRP6. In a further embodiment, the anti-LRP6 antibody further interacts with at least one, at least two, at least three, at least four, at least five, at least six, at least seven of the LRP6 residues R29, W188, K202, P225, H226, S243, and F266.

In a further aspect, an anti-LRP6 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μL1/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall' Acqua et al., *Meth-* ods 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMABO technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for LRP6 and the other is for any other antigen. In certain embodiments, a bispecific antibody binds to two different epitopes of LRP6. Bispecific antibodies may also be used to localize cytotoxic agents to cells which express LRP6. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to LRP6 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |

TABLE 1-continued

| Original Residue | Exemplary Substitutions | Preferred Substitutions |
| --- | --- | --- |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166: 1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S, and M. J. Glennie, *Blood* 103:2738-2743 (2004)). FcRn binding and in vivo clearance/half life determinations can also be performed using methods known in the art (see, e.g., Petkova, S. B. et al., *Int'l Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-LRP6 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-LRP6 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-LRP6 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B.K.C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g. U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B.K.C. Lo, ed., Humana Press, Totowa, N.J.), pp. 255-268 (2003).

C. Assays

Anti-LRP6 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with an anti-LRP6 antibody of the invention for binding to LRP6. In certain embodiments, such a competing antibody binds to the same epitope (e.g., a linear or a conformational epitope) that is bound by an anti-LRP6 antibody of the invention. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized LRP6 is incubated in a solution comprising a first labeled antibody that binds to LRP6 and a second unlabeled antibody that is being tested for its ability to compete with the first antibody for binding to LRP6. The second antibody may be present in a hybridoma supernatant. As a control, immobilized LRP6 is incubated in a solution comprising the first labeled antibody but not the second unlabeled antibody. After incubation under conditions permissive for binding of the first antibody to LRP6, excess unbound antibody is removed, and the amount of label associated with immobilized LRP6 is measured. If the amount of label associated with immobilized LRP6 is substantially reduced in the test sample relative to the control sample, then that indicates that the second antibody is competing with the first antibody for binding to LRP6. See Harlow and Lane (1988) *Antibodies: A Laboratory Manual* ch.14 (Cold Spring Harbor Laboratory, Cold Spring Harbor, N.Y.).

2. Activity Assays

In one aspect, assays are provided for identifying anti-LRP6 antibodies thereof having biological activity. Biological activity may include, e g inhibiting or potentiating Wnt isoform mediated signaling, modulated bone mass/content, inhibiting cellular proliferation, increasing cellular proliferation. Antibodies having such biological activity in vivo and/or in vitro are also provided.

In certain embodiments, an antibody of the invention is tested for such biological activity. Specific assays used to test the biological activities are provided in the Examples.

D. Immunoconjugates

The invention also provides immunoconjugates comprising an anti-LRP6 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethyl-lauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770, 701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.*

45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-LRP6 antibodies provided herein is useful for detecting the presence of LRP6 in a biological sample. The term "detecting" as used herein encompasses quantitative or qualitative detection. In certain embodiments, a biological sample comprises a cell or tissue.

In one embodiment, an anti-LRP6 antibody for use in a method of diagnosis or detection is provided. In a further aspect, a method of detecting the presence of LRP6 in a biological sample is provided. In certain embodiments, the method comprises contacting the biological sample with an anti-LRP6 antibody as described herein under conditions permissive for binding of the anti-LRP6 antibody to LRP6, and detecting whether a complex is formed between the anti-LRP6 antibody and LRP6. Such method may be an in vitro or in vivo method. In one embodiment, an anti-LRP6 antibody is used to select subjects eligible for therapy with an anti-LRP6 antibody, e.g. where LRP6 is a biomarker for selection of patients.

Exemplary disorders that may be diagnosed using an antibody of the invention include cancer and disorders of the skeletal system.

In certain embodiments, labeled anti-LRP6 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-LRP6 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-LRP6 antibodies provided herein may be used in therapeutic methods.

In one aspect, an anti-LRP6 antibody for use as a medicament is provided. In further aspects, an anti-LRP6 antibody for use in treating a Wnt mediated disorder, such as cancer or a skeletal or bone disorder, is provided. In certain embodiments, an anti-LRP6 antibody for use in a method of treatment is provided. In certain embodiments, the invention provides an anti-LRP6 antibody for use in a method of treating an individual having cancer or a skeletal or bone disorder comprising administering to the individual an effective amount of the anti-LRP6 antibody. In one such embodiment, the method further comprises administering to the individual an effective amount of at least one additional therapeutic agent, e.g., as described below. In further embodiments, the invention provides an anti-LRP6 antibody for use in inhibiting signaling induced by a first Wnt isoform and potentiating signaling induced by a second Wnt isoform. In certain embodiments, the invention provides an anti-LRP6 antibody for use in a method of inhibiting signaling induced by a first Wnt isoform and potentiating signaling induced by a second Wnt isoform in an individual comprising administering to the individual an effective of the anti-LRP6 antibody to inhibit signaling induced by a first Wnt isoform and potentiate signaling induced by a second Wnt isoform. An "individual" according to any of the above embodiments is preferably a human.

In a further aspect, the invention provides for the use of an anti-LRP6 antibody in the manufacture or preparation of a medicament. In one embodiment, the medicament is for treatment of a Wnt mediated disorder, such as cancer or a skeletal or bone disorder, In a further embodiment, the medicament is for use in a method of treating a Wnt mediated disorder, such as cancer or a skeletal or bone disorder, comprising administering to an individual having the Wnt mediated disorder an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating a Wnt mediated disorder, such as cancer or a skeletal or bone disorder. In one embodiment, the method comprises administering to an individual having such Wnt mediated disorder an effective amount of an anti-LRP6 antibody. In one such embodiment, the method further comprises administering to the individual an effective amount of at least one additional therapeutic agent, as described below. An "individual" according to any of the above embodiments may be a human.

In one embodiment, the Wnt mediated disorder is a cancer such as, for example, non-small cell lung cancer, breast cancer, pancreatic cancer, ovarian cancer, kidney cancer, or prostate cancer. In another embodiment, the Wnt mediated disorder is a skeletal or bone disorder, such as, for example, osteoporosis, osteoarthritis, bone fractures, or bone lesions.

One embodiment provides for a method of treating an individual having cancer comprising administering to the individual an effective amount of an antibody that binds to LRP6 and inhibits signaling induced by a Wnt isoform selected from the group consisting of Wnt3 and Wnt3a, and an antibody that binds to LRP6 and inhibits signaling induced by a Wnt isoform selected from the group consisting of Wnt 1, 2, 2b, 6, 8a, 9a, 9b, and 10b. Another embodiment provides for a method of treating an individual having cancer comprising administering to the individual an effective amount of an antibody that binds to LRP6 and inhibits signaling induced Wnt3 and Wnt3a, and an antibody that binds to LRP6 and inhibits signaling induced by Wnt 1, 2, 2b, 6, 8a, 9a, 9b, and 10b. Another embodiment provides for a method of treating an individual having cancer comprising administering to the individual an effective amount of an antibody that binds to LRP6 and inhibits signaling induced Wnt3 and Wnt3a, and an antibody that binds to LRP6 and inhibits signaling induced by Wnt 1, 2, 2b, 4, 6, 7a, 7b, 8a, 9a, 9b, 10a, and 10b.

In a further aspect, the invention provides a method for potentiating Wnt signaling induced by a Wnt isoform in an individual comprising administering to the individual an effective amount of an anti-LRP6 antibody that potentiates signaling by the Wnt isoform and the Wnt isoform to potentiate Wnt signaling induced by the Wnt isoform. In one In a further aspect, the invention provides pharmaceutical formulations comprising any of the anti-LRP6 antibodies provided herein, e.g., for use in any of the above therapeutic methods. In one embodiment, a pharmaceutical formulation comprises any of the anti-LRP6 antibodies provided herein and a pharmaceutically acceptable carrier. In another embodiment, a pharmaceutical formulation comprises any of the anti-LRP6 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent. In another embodiment, the agent is an antibody that is effective in treating cancer or in treating skeletal or bone disorders. Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-LRP6 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-LRP6 antibody.

III. Examples

The following are examples of methods and compositions of the invention. It is understood that various other embodiments may be practiced, given the general description provided above.

Example 1

Experimental Procedures
Cell Culture and Cell Assays

Cell lines EKVX and M14 were grown in RPMI-1640 medium supplemented with 10% fetal bovine serum and 2 mM glutamine; JHH-1 cells were grown in Williams' Medium E with the same supplements. All other cell lines were obtained from American Type Culture Collection (ATCC) and maintained as recommended.

Cell were transfected with FuGENE 6 transfection reagent (Roche) in 24-well plates according to the manufacturer's recommendations. For luciferase reporter assays, a mixture of expression plasmid DNA was transfected: 7.5 ng TOPglow (Upstate) or TOPbrite (Zhang et al., 2009) firefly luciferase Wnt reporter, 0.5 ng pRL-SV40 *Renilla* luciferase (Promega), and 1 ng LEF1. Cells were treated with antibodies for 16-20 h, starting 24 h after transfection. Wnt3a protein (purified according to X, or purchased from R&D Systems)

was added to cells starting 1 h after initiating antibody treatment. Cells were harvested in 150 ul of lysis buffer (DeAlmeida et al., 2007), and luminescence was assayed for 30-50 ul of lysate using the Dual-Glo Luciferase System (Promega) and Envision Multilabel Reader (PerkinElmer). Firefly luciferase levels were normalized for transfection efficiency to *Renilla luciferase* levels, and the relative luciferase units (RLU) were additionally normalized to the level in cells not stimulated with Wnt3a.

HEK293 and Hs578T cell lines stably integrated with TOPbrite reporter were selected for hygromycin resistance. Expression of Wnt luciferase reporter is normalized to cell number based on stably integrated SV40-driven *Renilla* luciferase for HEK293 cells or on the MultiTox-Fluor cell viability assay (Promega) for Hs578T cells.

Wnt chimera constructs were made by cloning full-length Wnt1 or Wnt3a upstream of full-length FZD4, FZD5, or LRP6 in pRK5 expression vector. The 24-amino acid linker $(GGGSGGGT)_3$ was inserted between Wnt and FZD or LRP6 sequences (Cong et al., 2004).

The one-armed YW211.31 antibody variant was produced in *E. coli* by co-expressing the YW211.31.62 heavy and light chains with a truncated Fc domain using 'knobs-into-holes' engineering technology (Ridgway, J. B. B. et al, *Protein Engineering* 9:617-621 (1996). For antibody cross-linking, Fc-specific goat-anti-human IgG antibody or F(ab')2 fragment (Sigma-Aldrich) was incubated with one-armed YW211.31 antibody for 1 h before adding the mixture to cells.

For Western analysis, $1.2 \times 10^6$ HEK293 cells were seeded onto 10-cm dishes and treated 3 days later with 10 μg/ml antibody, or X μg/ml DKK1 (R&D Systems) or Fzd8CRD-Fc (DeAlmeida et al., 2007) protein for 1 h before adding 0.2 ug/ml Wnt3a protein for an additional 1 h. Cells were washed twice with cold PBS and lysed in 0.5 ml lysis buffer on ice. 20 μg of protein was electrophoretically resolved on a denaturing SDS-polyacrylamide gel (4-12%), transferred to nitrocellulose membrane, and probed with antibodies against phospho- and total LRP6 (Cell Signaling Technology), β-catenin (BD Transduction Laboratories), β-actin and GAPDH. Proteins were visualized using infrared labeled secondary antibodies (Rockland Immunochemicals) and Odyssey imager (LI-COR).

For quantitative real-time PCR (qPCR) expression analysis, RNA was isolated from cells using the RNeasy kit (QIAGEN), and reactions were performed with the TaqMan One-Step RT-PCR Master Mix Reagents Kit (Applied Biosystems) on the 7900 HT Fast Real-Time PCR System (Applied Biosystems). Relative RNA levels were calculated using the ΔΔCt method and normalized to human GAPDH or mouse Rpl19RNA levels within the same sample, and additionally normalized to samples from cells with no addition (NA) of Wnt3a, antibody, or other proteins. The primer and probe sets, listed 5' to 3' for forward primer, reverse primer, and probe sequences, respectively, are

SPS:
(SEQ ID NO: 32)
AATGCTGCTGAACTGAATAGAAA, (SEQ ID NO: 33)
AACCGGTCCTAGCGAAAA, (SEQ ID NO: 34)
CCGAGCACTGTTTCAAATCTCCCA;

ZNRF3:

(SEQ ID NO: 35)
TGAGAGTGTGACATTGTTGGAA, (SEQ ID NO: 36)
GTAAAATCTGTGTGCAATTATCATGT, (SEQ ID NO: 37)
AATCATTGAAAATGACTAACACAAGACCCTGTAAAT;

mouse Mmp7:
(SEQ ID NO: 38)
TGAGGACGCAGGAGTGAA, (SEQ ID NO: 39)
CCCAGAGAGTGGCCAAAT, (SEQ ID NO: 40)
CCTGTTTGCTGCCACCCATGA.

Primers and probes used for human APCDD1, AXIN2, GAD1, LEFTY2, and SAX1, and for mouse Rpl19 and Axin2, were previously described (DeAlmeida, et al. (2007); Liu et al., (2010)).

GAPDH primers and probe were purchased from Applied Biosystems. For reporter gene and qPCR assays, all figures represent the mean and standard deviation of three or four experimental replicates.

LRP6 Antibody Screening and Affinity Maturation

Human LRP6 cDNA fragments encoding regions E1-E2 (amino acids A19—R644 of SEQ ID NO: 29) and E3-E4 (amino acids V629-G1244 of SEQ ID NO:29) were separately cloned into a mammalian expression vector containing the HSV signal sequence and human IgG Fc region as a protein tag (SEQ ID NO: 30 (E1-E2-fc); SEQ ID NO: 31 (E3-E4-fc)). LRP6.E1-E2-Fc and LRP6.E3-E4-Fc proteins were expressed in CHO cells by transient transfection and purified by Protein A/G affinity chromatography. LRP6.E1-E2-Fc and LRP6.E3-E4-Fc proteins were also used individually to screen a human synthetic Fab phage display library. After selection on immobilized LRP6 protein, phage clones were isolated and confirmed by phage ELISA for binding to the LRP6-Fc fusion protein fragment and not Fc protein. Phage Fab clones were then reformatted for expression as human IgG1 monoclonal antibodies. 24 unique antibody heavy chain clones against LRP6.E1-E2-Fc and 22 clones against LRP6.E3-E4-Fc were transfected and transiently expressed in HEK293 cells with a common Herceptin-derived human kappa light chain, and IgG protein was purified by affinity chromatography. Subsequent large-scale antibody preparations were produced by transient transfection in CHO cells.

YW211.31 antibody was affinity-matured using His-tagged LRP6.E3-E4 protein. Three different combinations of CDR loops (H1/L3, H2/L3, and H3/L3) were targeted for randomization in separate libraries by soft-randomizing selected residues. In addition, the L1/L2/L3 CDR combination was targeted for hard randomization. In the first round of selection, phage from the randomized libraries were selected with immobilized LRP6.E3-4-His protein, followed by five rounds of solution-phase sorting in which the concentration of LRP6.E3-4-His was gradually reduced from 300 nM to 0.5 nM, and a 100-fold excess of LRP6.E3-4-Fc protein was added to deplete antibodies with faster dissociation rates. Eleven phage clones were purified, and all showed improved affinity for LRP3.E3-E4 as determined by phage competition ELISA. The sequence of these clones displayed 1 to 6 amino acid changes in CDR-H1, CDR-H3, and CDR-L3. Dissociation rate constants of the purified antibodies were assessed by surface plasmon resonance analysis using a BIAcore instrument.

Biolayer Interferometry LRP6 Protein Binding Assay

Biolayer interferometry was performed as previously described (Bourhis et al., 2010). Briefly, biotinylated, His-tagged LRP6 proteins were purified from baculovirus-infected insect cells using the AviTag system (GeneCopoeia). Binding kinetics were measured on the Octet RED System (ForteBio) using Streptavidin High Binding FA Biosensors loaded with 20 µg/ml LRP6 protein. Carrier-free purified human Wnt3a and mouse Wnt9b were obtained from R&D Systems, and purified DKK1 protein was produced as previously described (Bourhis et al., 2010).

Tumor and Bone Studies

Tumors from MMTV-Wnt1 transgenic mice were passaged in mammary fat pads of C57BL/6 mice, mechanically and enzymatically dissociated, resuspended in Matrigel and Hank's Balanced Salt Solution (HBSS), and injected into the mammary fat pad of athymic NCr nude mice (Taconic). Treatments were initiated once tumor volumes reached 250-800 mm$^3$. For each treatment group, ten mice were administered 30 mg/kg of antibody or protein intraperitoneally (IP) every two days. Tumor volume was analyzed using caliper measurement.

Ntera-2 xenograft tumor growth and in vivo studies were performed as previously described (DeAlmeida et al., 2007). Briefly, NU/NU athymic nude mice (Charles River) were injected subcutaneously with 10 million Ntera-2 cells (in 50% Matrigel in HBSS) per mouse, divided into groups of four or five animals with once mean tumor volumes reached 535-595 mm$^3$, and injected with a single IP dose of 100 mg/kg antibody or 30 mg/kg Fzd8CRD-Fc protein. Tumor and blood serum samples were collected 16 h after treatment. Tumors were homogenized using the TissueLyser system (QIAGEN), and RNA was extracted using the RNeasy kit (QIAGEN).

Calvariae were harvested and cultured as described by Mohammad et al., 2008. Briefly, calvariae were dissected from 2-day-old mouse pups, cut into halves, and separated from dura mater, vessels, and scalp. Calvariae were cultured in tissue culture plates in BGJb medium supplemented with 0.1% bovine serum albumin and 100 U/ml each of penicillin and streptomycin for 1 day before treating with 10 µg/ml antibody or protein for 7 days. The bones were cultured in a humidified atmosphere of 5% $CO_2$ at 37° C. Mouse calvariae were imaged with a µCT 40 (SCANCO Medical, Basserdorf, Switzerland) x-ray micro-CT system. The micro-CT data were acquired with the following parameters: x-ray tube energy level=45 kV, current=177 µA, integration time=300 msec, 2000 projections. Axial images were obtained at an isotropic resolution of 6 µm. A hydroxyapatite (HA) phantom was used for calibration. Micro-CT scans were analyzed with Analyze (AnalyzeDirect Inc., Lenexa, Kans., USA). Maximum-intensity projections and three-dimensional surface renderings in the transverse plane were created for each sample. Parietal bone borders were manually drawn using the Trace tool in order to segment the parietal region. Within this region, sample volume and mean bone mineral density (BMD) were calculated. A threshold of 0.3 gm-HA/cm$^3$ was applied to the region in order to calculate the mean BMD of only calcified tissue within the region. The threshold was also used to calculate percentage calcified volume of the parietal region by dividing the number of calcified voxels over the total voxels for the parietal region. The following parameters were analyzed for each sample: parietal region volume, BMD of calcified voxels of the parietal region, and parietal region percentage calcified. Differences between groups were considered significant if p-values were less than 0.05 by Dunnett's test.

All experiments using mice were performed in accordance with Genentech Institutional Animal Care and Use Committee guidelines.

Example 2

Isolation of Wnt Antagonist and Potentiating LRP6 Monoclonal Antibodies

Figure 1B:
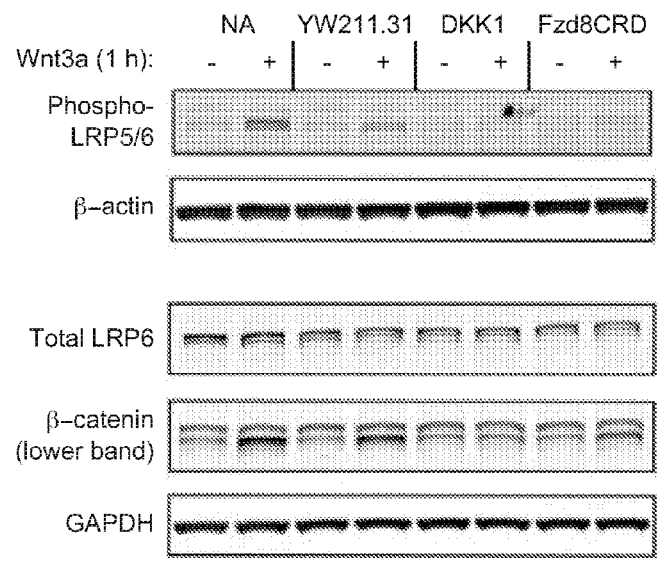
FIG. 1B. Western blot analysis of HEK293 cells either unstimulated or induced with Wnt3a and treated with the indicated LRP6 antibody or purified protein FIG. 1C. Graph showing that the YW210.09 antibody potentiates Wnt reporter gene activity in a manner proportional to Wnt3a concentration in HEK293 cells.

To develop candidate therapeutic molecules to manipulate Wnt signaling, antibodies that can either inhibit or enhance signaling induced by Wnt3a protein were generated. Recombinant LRP6.E1-E2-Fc (SEQ ID NO: 30) and LRP6.E3-E4-Fc (SEQ ID NO: 31) proteins were used to screen a human synthetic Fab phage display library and confirmed binding of isolated phage clones to LRP6 by ELISA. 24 unique antibody heavy chain clones against LRP6.E1-E2 and 22 clones against LRP6.E3-E4 were isolated, reformatted and expressed as human IgG1 antibodies. Six of the LRP6.E3-E4 antibodies inhibited in a concentration-dependent manner the Wnt luciferase reporter activity in HEK293 cells induced with 0.1 mg/ml purified Wnt3a (FIG. 1A. Error bars of this and all other graphs, except where noted, represent standard deviation of at least 3 replicate samples). These antibodies were designated YW211.03, YW211.08, YW211.11, YW211.12, YW211.31, and YW211.33. None of the LRP6.E1-E2 antibodies exhibited this inhibition. The YW211.31 antibody recognizing the LRP6.E3-E4 domain was the most potent in inhibiting signaling in Wnt3a-stimulated HEK293 cells, with an $IC_{50}$ of approximately 1 ug/ml (or 6 nM). YW211.31 antibody inhibited Wnt3a-induced LRP6 phosphorylation and β-catenin protein stabilization without affecting levels of LRP6 protein, similar to purified Fzd8CRD and DKK1 proteins (FIG. 1B, showing Western analysis of HEK293 cells either unstimulated or induced with Wnt3a and treated with the indicated LRP6 antibody or purified protein (b-actin and GAPDH protein levels are shown as sample loading controls)). RNAi experiments demonstrated that only the lower molecular weight band recognized by the b-catenin polyclonal antibody represents b-catenin protein. YW211.31 antibody can also antagonize mouse Lrp6 function since it partially inhibits Wnt3a-induced reporter activity in mouse NIH/3T3 cells and β-catenin protein stabilization in mouse L cells.

YW211.31 antibody has a binding affinity of about 2 nM by surface plasmon resonance (SPR) and 0.6 nM by Scatchard analysis. To improve affinity and potential potency of YW211.31 antibody, the clone was affinity-matured using His-tagged LRP6 E3-E4 protein and CDR combinatorial libraries in which selected CDR residues were targeted for randomization. Four phage clones showing the most improved affinity by phage competition ELISA, YW211.31.11, YW211.31.11, 35, YW211.31.57, and YW211.31.62, were reformatted and expressed as full length human IgGs. The dissociation rate constants of all four affinity-matured IgGs were decreased, leading to improved affinities for the best two antibodies, YW211.31.57 and YW211.31.62, of KD 0.27 and 0.17 nM, respectively. YW211.31.57 and YW211.31.62 also show improved potency in inhibiting signaling in Wnt3a-stimulated HEK293 cells, with IC50 values of approximately 0.1 µg/ml (0.6 nM).

Figure 1C:
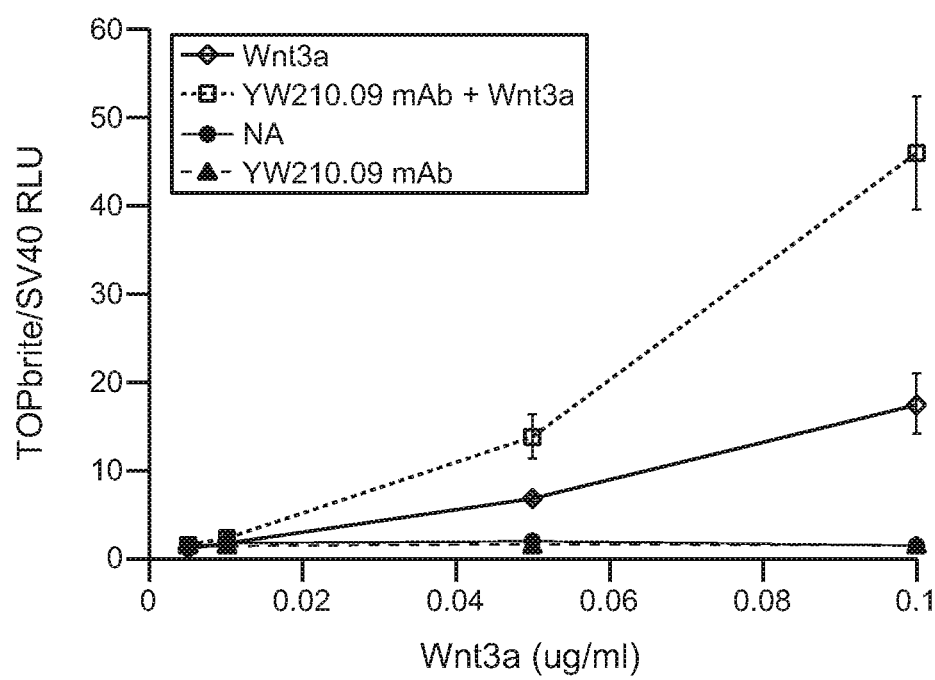

None of the antibodies isolated in the screen activated signaling in HEK293 cells in the absence of stimulation with exogenous Wnt3a protein, however five of the LRP6 E1-E2 and two of the E3-E4 antibodies potentiated Wnt3a-induced signaling at least 2-fold. In mouse NIH/3T3 cells, YW210.09, an E1-E2 antibody, also potentiated Wnt3a-induced signaling at least 1.5-fold, indicating that it also recognizes mouse LRP6. In HEK293 cells, the magnitude of enhancement of Wnt3a-induced signaling by YW210.09 antibody is proportional to Wnt3a concentration (FIG. 1C). YW210.09 antibody interacts with human LRP6 E1-E2 protein with a KD of 5 nm as measured by SPR analysis. ELISA testing shows that all antagonist and potentiating antibodies specifically bind only the LRP6 protein fragment employed for their isolation, and none recognize both E1-E2 and E3-E4. FACS analysis indicated that soluble LRP6 E1-E4 protein efficiently and completely blocks binding of YW211.31.57 and YW210.09 to HEK293 cells, indicating that these antibodies do not recognize other cell surface proteins.

Example 3

Effects of LRP6 Monoclonal Antibodies on Autocrine Wnt Signaling

Figure 2A:
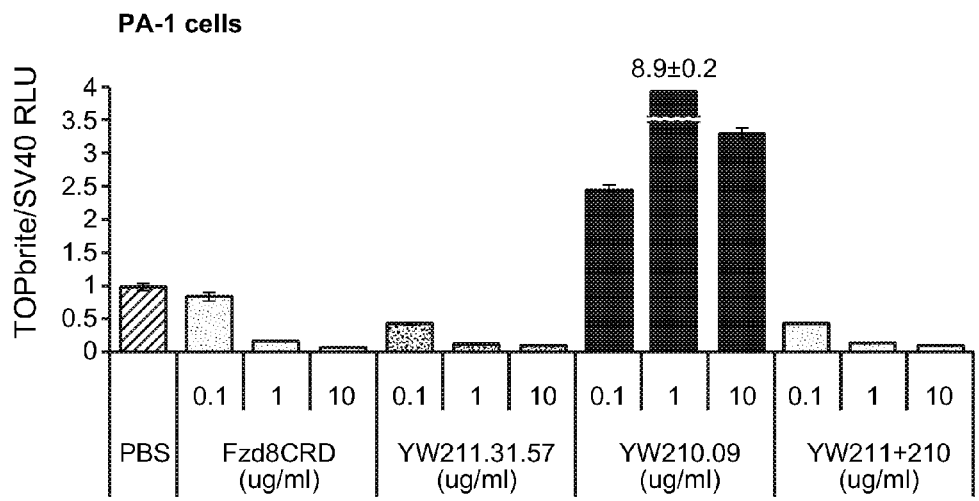
FIG. 2A. Graph showing concentration-dependent inhibition and potentiation of autocrine Wnt signaling in PA-1 teratocarcinoma cells transfected with luciferase reporters and treated with LRP6 antibodies, either individually or in combination, or Fzd8CRD-Fc protein.

The ability of the LRP6 antibodies to antagonize or potentiate endogenous, or autocrine, Wnt signaling was determined using a variety of tumor cell lines (Bafico et al., 2004; DeAlmeida et al., 2007; Akiri et al., 2009). In teratocarcinoma cell lines PA-1 and NTERA-2, the YW211.31 antibody inhibits reporter activity induced by autocrine Wnt signaling with similar potency to that observed with exogenous Wnt3a (FIG. 2A showing concentration-dependent inhibition and potentiation of autocrine Wnt signaling in PA-1 teratocarcinoma cells transfected with luciferase reporters and treated with LRP6 antibodies, either individually or in combination, or Fzd8CRD-Fc protein (positive control)).

Figure 2B:
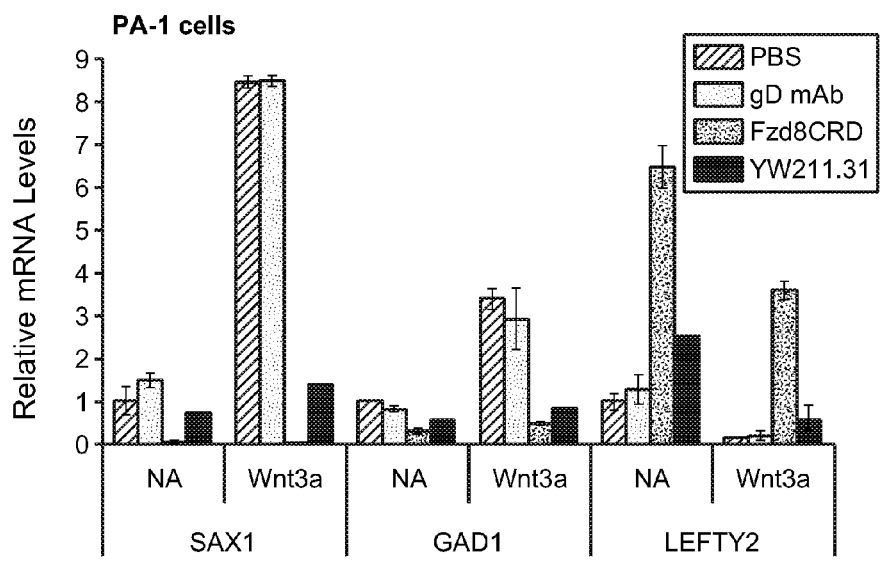

In PA1 cells, inhibition of Wnt signaling by YW211.31 antibody is also observed for expression of endogenous Wnt target genes (FIG. 2B). FIG. 2B shows the results of qPCR expression analysis of Wnt-induced genes SAX1 and GAD1 and Wnt-repressed gene LEFTY2 in PA-1 cells treated with or without 0.3 mg/ml Wnt3a protein, and treated with 10 mg/ml YW211.31 antibody, anti-gD monoclonal antibody as a negative control, or Fzd8CRD-Fc protein as a positive control sample, and additionally normalized to samples from cells with no addition (NA) of Wnt3a.

The antibody partially inhibits expression of SAX1, GAD1, and APCDD1 that is either induced by exogenous Wnt3a protein or maintained by endogenous, autocrine Wnt signaling. Conversely, repression of LEFTY2 expression by either Wnt3a protein or autocrine Wnt signaling is relieved by YW211.31 antibody. In contrast to YW211.31, YW210.09 antibody potentiates both Wnt3a-induced and autocrine Wnt signaling in PA-1 and NTERA-2 cell lines by reporter gene assays (FIG. 2A). Whereas inhibition of Wnt signaling by YW211.31.57 antibody increases progressively with greater antibody concentration, potentiation by YW210.09 and other antibodies can decrease at high antibody concentrations in some cell types, such as PA-1 cells. This may suggest that receptor LRP6 dimerization is required for potentiation, since high antibody concentrations would favor monovalent interactions and thus limit crosslinking of LRP6 molecules. Treatment of PA-1 or NTERA-2 cells with a combination of both YW211.31.57 and YW210.09 antibodies antagonizes both Wnt3a-induced and autocrine Wnt signaling, similar to the effect of YW211.31.57 alone.

Figures 3, 4A:
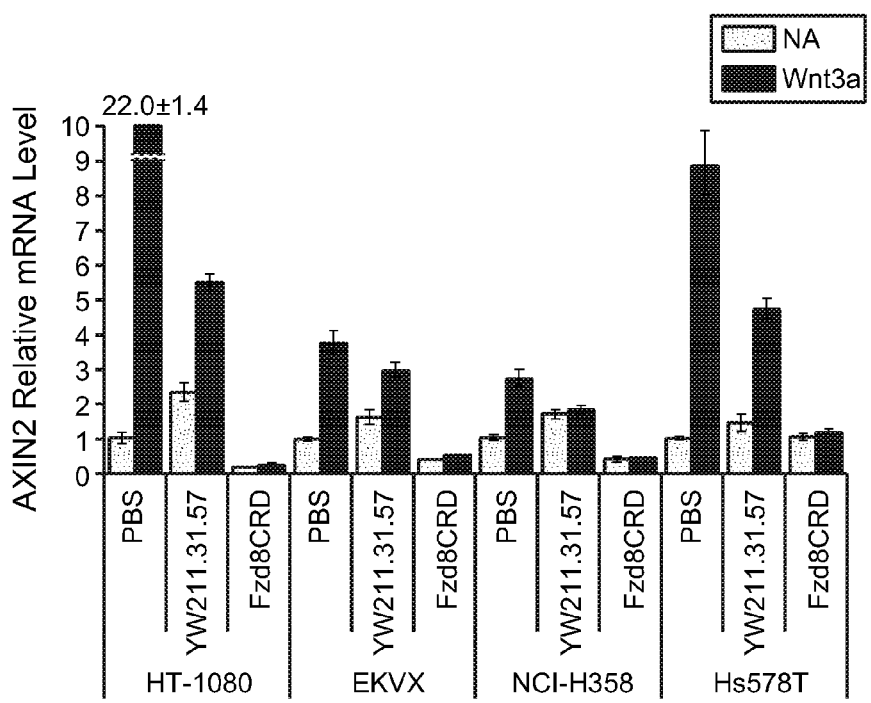

To identify additional cell lines that display autocrine Wnt signaling, cell lines with relatively high expression of Axin2 mRNA or phospho-LRP5/6 were tested for inhibition of Wnt signaling by Fzd8CRD-Fc protein in Wnt luciferase reporter gene assays. Nine cell lines exhibited autocrine Wnt signaling that was inhibited by Fzd8CRD-Fc protein, including NSCLC cells NCI-H23 and NCI-H2030 and soft tissue sarcoma cells SW872 and HT-1080 that have previously been reported to have endogenous Wnt signaling based on assays with other Wnt antagonists (Guo et al., 2008; Akiri et al., 2009; Nguyen et al., 2009) FIG. 3 shows a summary of data analyzed by one-way analysis of variance (ANOVA) (with p-value <0.01). The assays were performed using 10 mg/ml of the antibodies, except for NCI-H358 and HT-1080 cells which were treated with 1 mg/ml YW211.31.57 or YW210.09 antibody, respectively, to increase potentiation effects.

Figure 4B:
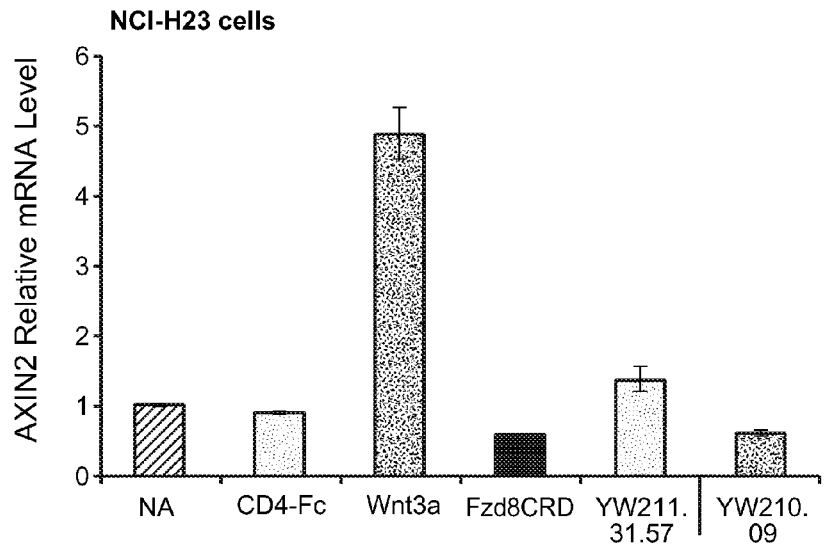
FIG. 4B. Graph depicting expression of Wnt-induced genes in NCI-H23cells is potentiated by YW211.31.57 and antagonized by YW210.09 antibody (30 μg/ml). CD4-Fc protein (30 μg/ml) serves as a negative control.
Figure 4C:
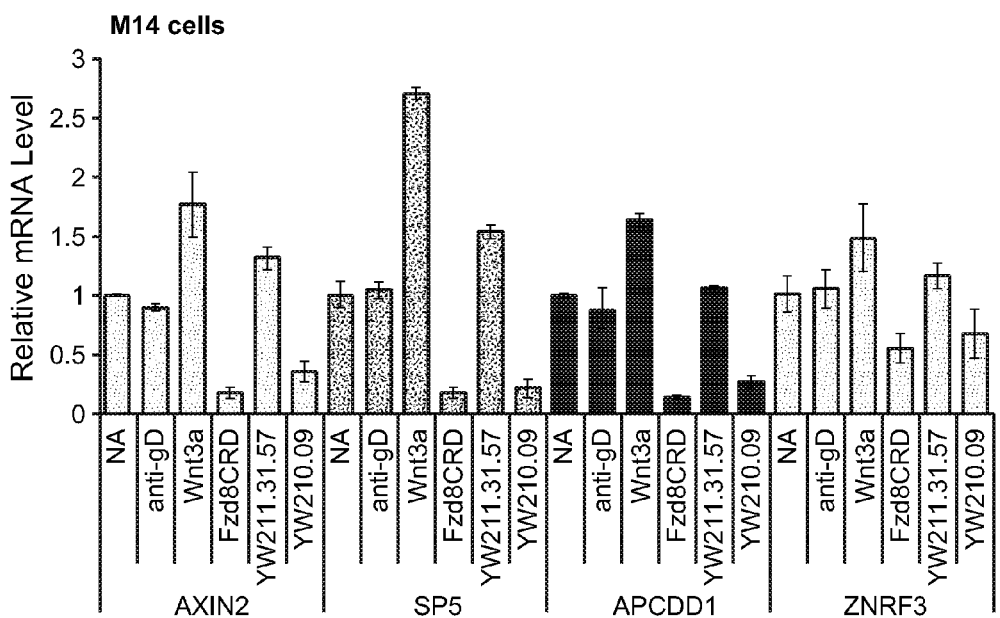
FIG. 4C. Graph depicting expression of Wnt-induced genes in M14 cells is potentiated by YW211.31.57 and antagonized by YW210.09 antibody (30 μg/ml).
Figure 4D:
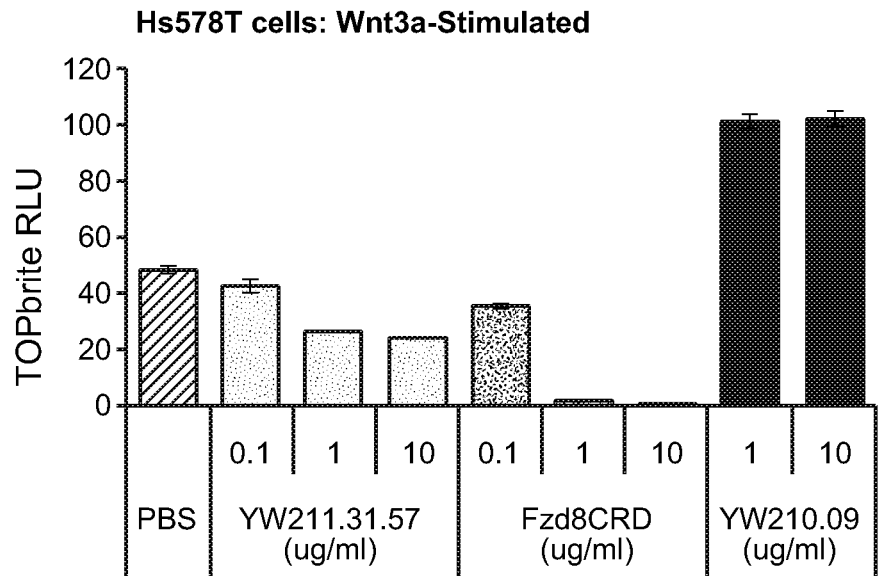
FIG. 4D. Graph showing concentration-dependent inhibition of Wnt3a-stimulated signaling by YW211.31.57 antibody in Hs578T cells stably integrated with Wnt luciferase reporter.
Figure 4E:
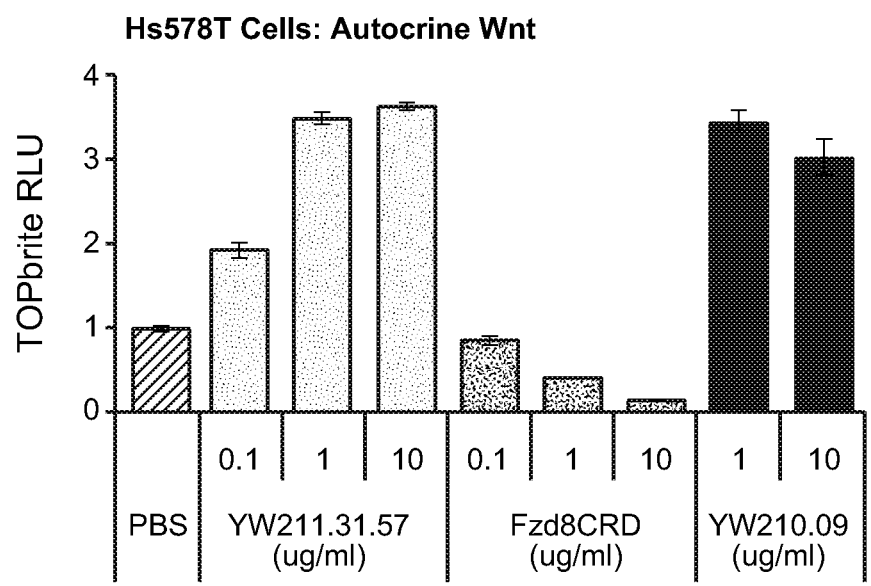
FIG. 4E. Graph showing concentration-dependent potentiation of autocrine Wnt signaling signaling by YW211.31.57 antibody in Hs578T cells stably integrated with Wnt luciferase reporter.
Figure 4F:
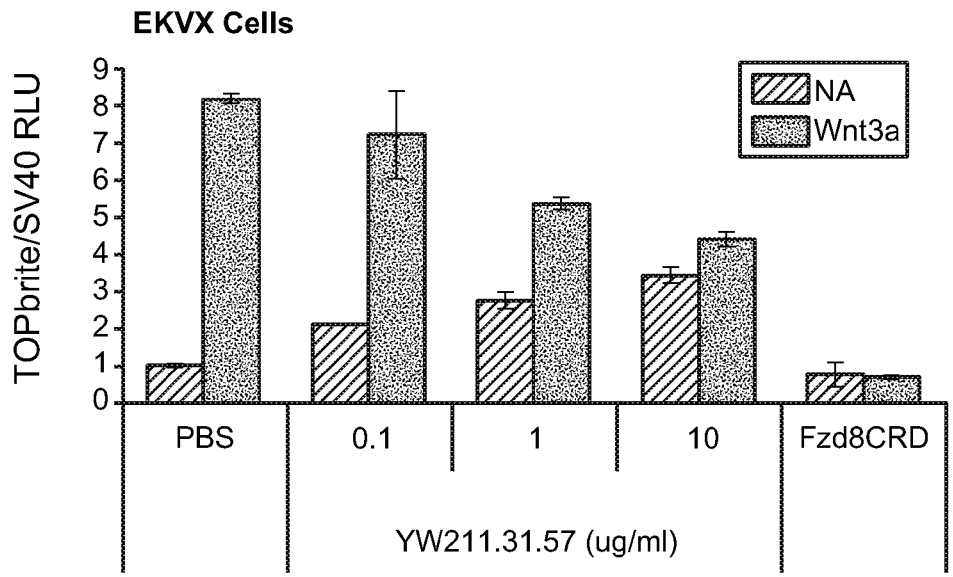
FIG. 4F. Graph showing that EKVX cells transfected with Wnt luciferase reporter display potentiation of autocrine Wnt signaling (NA) and antagonism of Wnt3a-induced signaling by YW211.31.57 antibody.
Figure 4G:
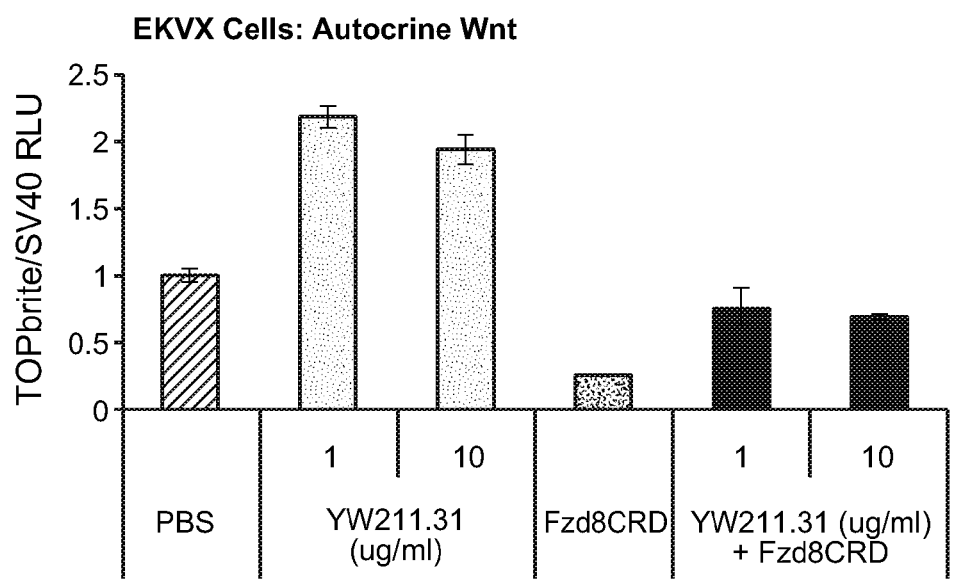
FIG. 4G. Graph showing that antibody-mediated potentiation of autocrine Wnt signaling is inhibited by 5 μg/mlFzd8CRD-Fc protein.

Wnt signaling was further induced in all nine cell lines by exogenous Wnt3a protein, and YW211.31.57 antibody inhibited this response to Wnt3a (FIG. 3, 4A, 4D, and 4F). Surprisingly, YW211.31.57 antibody potentiated autocrine Wnt signaling in all nine of these cell lines, whereas YW210.09 potentiated autocrine Wnt signaling in five lines and inhibited in three lines (FIG. 3, 4A-4C, 4E, and 4F). This reciprocal activity of YW211.31.57 antibody on autocrine and Wnt3a-induced signaling was observed not only using the luciferase reporter, but also for expression of endogenous Wnt target genes such as Axin2 in the six cell lines tested (FIGS. 4A, 4B, and 4C). In EKVX and breast carcinoma Hs578T cell lines, the increase in Wnt signaling by YW211.31 antibody was confirmed to be dependent on autocrine Wnt(s) by demonstrating that this increase is blocked by Fzd8CRD-Fc protein (FIG. 4G). Potentiation of autocrine Wnt signaling in EKVX and Hs578T cells is also observed with the other five antibody antagonists of Wnt3a-induced signaling identified in the screen.

In FIG. 4A, qPCR expression analysis of AXIN2 mRNA in HT-1080, EKVX, NCI-H358, and Hs578T indicates that YW211.31.57 (25 mg/ml) antibody potentiates autocrine (NA) Wnt signaling and inhibits signaling induced by Wnt3a (0.2 mg/ml), whereas Fzd8CRD-Fc (25 mg/ml) antagonizes both autocrine (NA) and Wn3a-induced signaling. In FIGS. 4B and 4C, expression of Wnt-induced gene in NCI-H23 (B) and M14 (C) cells is potentiated by YW211.31.57 and antagonized by YW210.09 antibody (30 mg/ml). Wnt3a (0.2 mg/ml) and Fzd8CRD-Fc (30 mg/ml) treatments are shown as positive controls for potentiation and inhibition, respectively, of autocrine Wnt signaling, and CD4-Fc protein (B) or anti-gD antibody (C) serve as a negative controls (30 mg/ml). For M14 cells (C), $AX_1N2$ and SP5 expression is potentiated more potently by Wnt3a protein or YW211.31.57 antibody than is APCDD1 and ZNRF3 expression. FIGS. 4D and 4E show that in Hs578T cells stably integrated with Wnt luciferase reporter, YW211.31.57 antibody shows concentration-dependent inhibition of Wnt3a-stimulated signaling (D) and potentiation of autocrine Wnt signaling (E), whereas Fzd8CRD-Fc protein inhibits and YW210.09 antibody potentiates signaling with or without (NA) 0.1 mg/ml Wnt3a stimulation. RNAi experiments indicate that at least 41% of Wnt3a-induced signaling in Hs578T cells is dependent on LRP5 expression, and this signaling is predicted to be inhibited by Fzd8CRD-Fc protein but not YW211.31.57 antibody. In this experiment, SV40-driven luciferase was not transfected for normalization and, instead, antibody and protein treatments were independently confirmed to have no significant effect on viability of this cell line. FIGS. 4F and 4G show that EKVX cells transfected with Wnt luciferase reporter also display potentiation of autocrine Wnt signaling and antagonism of Wnt3a-induced signaling by YW211.31.57 antibody. Antibody-mediated potentiation of autocrine Wnt signaling is inhibited by 5 mg/ml Fzd8CRD-Fc protein).

Example 4

Reciprocal Activities of LRP6 Antibodies on Different Wnt Isoforms

YW211.31 antibody inhibits signaling induced by exogenous Wnt3a protein in all cell lines, but can either inhibit or potentiate autocrine Wnt signaling in a cell line-dependent manner, suggesting that the specific Wnt isoform driving the autocrine signal specifies the activity of the antibody. Therefore, the activity of the antibody on signaling induced by exogenous expression of Wnt3a and other Wnt isoforms was determined Wnt signaling induced by transfection of Wnt3a in either HEK293 or Hs578T cells is inhibited by YW211.31.57 antibody with similar potency to inhibition of signaling induced by Wnt3a protein treatment. Surprisingly, signaling induced by Wnt1 expression in both cell lines was potentiated by YW211.31.57 antibody. Both Wnt1 and Wnt3a signaling are inhibited by Fzd8CRD-Fc protein as expected. Potentiation of Wnt1 signaling was also observed with the other Wnt3a antagonist antibodies identified in the screen. YW210.09 antibody also displayed opposing activities against Wnt3a- and Wnt1-induced signaling, which were the reciprocal of YW211.31.57 activities; i.e., potentiation of Wnt3a and inhibition of Wnt1 signaling. YW210.09 antibody also inhibits Wnt1 signaling in tumor cells grown in culture from MMTV-Wnt1 mouse tumors, as observed by reduced expression of Wnt target genes Axin2 and Mmp7 to a similar extent as Fzd8CRD-Fc protein treatment. In MMTV-Wnt1 cells, YW211.31.57 antibody failed to potentiate Wnt1 signaling, possibly because Wnt1 signaling is already maximal in these cells.

Having demonstrated that YW211.31.57 and YW210.09 antibodies have reciprocal activities on Wnt signaling initiated by Wnt3a and Wnt1, this analysis was also performed on an additional 11 of 19 Wnt genes that induce the luciferase reporter greater than two-fold in HEK293 cells. FIG. 5 provides a summary of the data, assays performed using 10 mg/ml of antibodies, 10 mg/mlFzd8CRD. Only Wnt3a and Wnt3 activities are inhibited by YW211.31.57 antibody, and both are potentiated by YW210.09. Seven Wnt isoforms in addition to Wnt1 are potentiated by YW211.31.57 and inhibited by YW210.09. A third class of Wnt isoforms (Wnt7a, 7b, and 10a) exhibit signaling activity that is not inhibited by either antibody and is potentiated by at least YW211.31.57. In Hs578T cells transfected with different Wnt isoforms, the antibodies display most of these same activities. In particular, YW211.31.57 inhibits Wnt3 and Wnt3a and potentiates all 11 of the other Wnt isoforms that induce the luciferase reporter at least two-fold. YW210.09 also potentiates Wnt3 and Wnt3a in Hs578T cells, as well as inhibits 5 of the 7 Wnt isoforms that are antagonized in HEK293 cells and able to be tested in Hs578T cells. The other two Wnt isoforms in this class, Wnt8a and Wnt9b, are not affected by YW210.09 antibody in Hs578T cells. Since RNAi experiments indicate that Wnt3a signaling in Hs578T but not HEK293 cells is transduced by both LRP6 and LRP5, Wnt 8a and Wnt9b might signal primarily through LRP5 in Hs578T cells. As in HEK293 cells, Wnt isoforms in the third class are not inhibited by either antibody in Hs587T cells, and we can add to this class Wnt4, which did not induce signaling in HEK293 cells. Only the activity of Wnt7b in this class behaves differently in that YW210.09 antibody potentiates its signaling in Hs578T but not HEK293 cells. In contrast to the Wnt isoform-specific activities of YW211.31.57 and YW210.09 antibodies, Fzd8CRD-Fc protein can potently inhibit the activity of all Wnts with the exception of Wnt6 and Wnt9b in HEK293 cells. In Hs578T cells, autocrine Wnt signaling is potentiated by both YW211.31.57 and YW210.09 antibodies, as is signaling induced by expression of Wnt4, Wnt7a, and Wnt7b. Thus these three Wnt isoforms are candidates for those that drive autocrine signaling in Hs578T cells.

Multiple siRNAs against Wnt7b, but not the other Wnt isoforms, inhibit autocrine signaling in Hs578T cells, identifying the specific Wnt protein mediating signaling. Since autocrine Wnt signaling in PA-1 cells is inhibited by YW211.31.57 antibody and potentiated by YW210.09, Wnt3 or Wnt3a likely activate endogenous signaling in these cells. Indeed, siRNAs against Wnt3 but not Wnt3a inhibit autocrine Wnt signaling in PA-1 cells. In NCI-H$_{23}$NSCLC cells and in M14 melanoma cells, potentiation of autocrine Wnt signaling by YW211.31 antibody and antagonism by YW210.09 are consistent with Wnt2 RNAi inhibiting endogenous signaling in NCI-H23 cell, and with endogenous Wnt1 expression in M14 cells. Using multiple siRNAs, we confirm that Wnt2 expression in NCI-H23 cells and Wnt1 in M14 cells are required for autocrine Wnt signaling.

Since all of the antibodies isolated from the screen in Example 2 that antagonize signaling in Wnt3a-stimulated HEK293 cells also inhibit Wnt3a stimulation in all other cell lines tested, and also inhibit autocrine Wnt signaling in teratocarcinoma cell lines, it was unexpected that these antibodies potentiate autocrine Wnt signaling in the other 9 cell lines tested. In addition, the YW210.09 antibody potentiates Wnt3a signaling in all cell lines tested and enhances autocrine Wnt signaling in 7 cell lines, but it inhibits endogenous signaling in 3 other lines. These studies show that different Wnt isoforms (expressed in the same cell line) determine the activity of the LRP6 antibodies, and that Wnt3a antagonist and potentiating antibodies also have reciprocal effects on most other Wnt proteins. The studies also show that the introduction of different Wnt isoforms into the same cell line determines the activity of the LRP6 antibodies, and that Wnt3a antagonist and potentiating antibodies also have reciprocal effects on most other Wnt proteins. Based on their functional interaction with two LRP6 antibodies, the 14 Wnt isoforms tested can be grouped into three classes: Wnt3 and Wnt3a are inhibited by YW211.31 and potentiated by YW210.09; Wnts 1, 2, 2b, 6, 8a, 9a, 9b, and 10b are potentiated by YW211.31 and antagonized by YW210.09; and Wnts 4, 7a, 7b, and 10a are potentiated by YW211.31 and not inhibited by YW210.09 (FIG. 5). These classifications do not obviously correspond to the proposed phylogeny of Wnt genes, although the Wnt3/3a subfamily is the most evolutionarily divergent (Cho et al., 2010).

Example 5

Wnt Isoforms Specify Different Activities of LRP6 Antibodies

Different Wnt isoforms may preferentially bind different FZD isoforms expressed endogenously in the various cell lines, and could conceivably account for the differential activities of our LRP6 antibodies. To examine this possibility, chimeric proteins covalently linking different Wnt-FZD pairs were constructed to test whether the specific Wnt or FZD isoform determines the activity of the LRP6 antibody. Wnt3a or Wnt1 fused to either FZD4 or FZD5 potently activates Wnt signaling in HEK293 cells in the presumed absence of endogenous Wnt expression, whereas overexpression of FZD4 or FZD5 does not induce Wnt signaling. YW211.31.57 antibody inhibits the signaling activity of Wnt3a fused to either FZD4 or FZD5, and potentiates the activity of Wnt1 fused to either FZD4 or FZD5 (FIG. 6 provides a summary of the data, assays performed using 10 µg/ml of antibodies, 10 mg/mlFzd8CRD). YW210.09 antibody shows the reciprocal activity against the Wnt1 chimeras, inhibiting both. Thus the activity of the antibody correlates with the Wnt isoform, and not the FZD isoform. Fzd8CRD-Fc protein has no effect on signaling induced by any of the four Wnt-FZD chimeras, consistent with the chimeras functioning independently of the FZD-binding site of Wnts.

Expression of chimeras that fuse Wnt1 or Wnt3a to LRP6 induce Wnt signaling much more potently than LRP6 overexpression. YW211.31.57 and YW210.09 antibodies are not able to inhibit this induction, consistent with the hypothesis that the inhibitory function of the antibodies is dependent on blocking Wnt binding to LRP6 (FIG. 6).

This study confirms that the isoform of Wnt, and not FZD, determines the activities of the antibodies Chimeric protein fusions of Wnt isoforms with LRP6, but not FZD, are insensitive to inhibition by the LRP6 antibodies, suggesting that antagonism may be mediated by blocking ligand-coreceptor interactions. This is confirmed by binding studies in vitro for Wnt3a and YW210.09 antibody, which both bind competitively within the E3-E4 region of LRP6, and for Wnt9b and YW211.31 antibody, which compete for binding within the E1-E2 region. The epitopes of the two LRP6 antibodies each define a binding site for a different class of Wnt isoforms, one within the E1-E2 and one within the E3-E4 domains. At least a third Wnt binding site is predicted for isoforms that are not inhibited by either antibody nor their combination, and it seems likely each of the four repeat domains binds a different subset of Wnt isoforms. This modular organization might allow for structural divergence of different Wnts and their binding sites to accommodate differential regulation by Wnt-binding and coreceptor binding antagonists such as SFRP and DKK protein isoforms, respectively.

Example 6

Antibody-mediated Potentiation of Wnt Signaling Involves LRP6 Dimerization

Potentiation of autocrine Wnt signaling by YW211.31 antibody requires avidity effects, presumably through LRP6 dimerization. The monovalent Fab fragment of YW211.31 and recombinant one-armed YW211.31 antibody exhibit no potentiation of autocrine Wnt signaling in EKVX and Hs578T cells at concentrations that inhibit Wnt3a-induced signaling in these cell lines). In contrast, the YW211.31 Fab fragment and one-armed mAb inhibit both autocrine Wnt and Wnt3a-induced signaling in the PA-1 teratocarcinoma cell line with similar potency to the intact IgG antibody. To test whether crosslinking of one-armed YW211.31 antibody would restore the Wnt potentiating function of the whole IgG molecule, the HT-1080 soft tissue sarcoma cell line that exhibits autocrine Wnt and Wnt2-induced signaling potentiated by YW211.31.57 antibody was used, as well as Apomab antibody-induced apoptosis that is enhanced by Fc crosslinking (Adams et al., 2008). The one-armed YW211.31 antibody has no effect on autocrine Wnt signaling or signaling induced by Wnt2 transfection. Under crosslinking conditions with anti-Fc antibodies that augment Apomab-mediated apoptosis, it was determined that crosslinking of the one-armed antibody partially reconstitutes the potentiation of both autocrine Wnt and Wnt2 signaling observed with the YW211.31.57 whole antibody.

Antibody-mediated Wnt potentiation requires coreceptor dimerization, since one-armed and Fab antibody formats fail to enhance Wnt signaling unless crosslinked. In addition, the cell-based and biochemical data presented herein indicate that Wnt binding to crosslinked LRP6 is also necessary for potentiation of signaling, presumably reflecting a requirement for Wnt-mediated recruitment of FZD into the complex. A small fraction of overexpressed LRP6 can be identified as a homodimer at the cell surface, and dimerization requires the extracellular domain, however it is not clear whether this contributes to the Wnt-independent b-catenin signaling induced by LRP6 overexpression (Liu et al., 2003). Deletion of the LRP6 extracellular domain also activates signaling in a Wnt-independent manner, and forced extracellular dimerization of this recombinant protein by different methods can either enhance or inhibit this activity (Liu et al., 2003; Cong et al., 2004). Wnt induces LRP6 aggregation and phosphorylation at the plasma membrane that both require the homo-oligomerization function of intracellular DVL protein (Bilic et al., 2007). These large aggregates also contain Axin and GSK3, and likely inhibit b-catenin degradation.

Example 7

Antibody-mediated Potentiation of Wnt Signaling by Inhibiting Binding of Wnt Antagonists Inhibiting the activity of extracellular LRP6 antagonists such as DKK1 isoforms and SOST can also potentiate Wnt signaling (Niida et al., 2004). Exogenous DKK1 protein inhibits Wnt1-induced signaling in HEK293 cells, and YW211.31.57 antibody can block this antagonism and even potentiate signaling at high enough concentration in the presence of DKK1 protein (FIG. 4G). In contrast, YW211.31 one-armed antibody only very weakly inhibits DKK1 antagonism of Wnt1 signaling at these same concentrations. YW211.31.57 whole antibody effectively antagonizes DKK1 activity at all DKK1 concentrations tested, whereas the one-armed antibody has minimal or no effect even at low DKK1 concentration. The potent antagonism of exogenous DKK1 activity observed with the whole but not the one-armed YW211.31 antibody may contribute to the Wnt-potentiating activity specific to the whole antibody. Alternatively, since DKK1 protein was not able to inhibit completely the Wnt1-induced signaling in this assay, it is also possible that the intact YW211.31 antibody simply potentiates the remaining signal through LRP6 dimerization.

Since antibody inhibition of DKK1 interaction with LRP6 does not necessarily confer Wnt potentiation activity, and DKK1 antagonism seems to require LRP6 dimerization, the inhibition of DKK1 activity is likely mediated predominantly by potentiation of residual signaling by Wnt bound to coreceptor.

Example 8

Wnt Signaling Antagonism Predominates in LRP6 Antibody Combinations

Figure 8A:
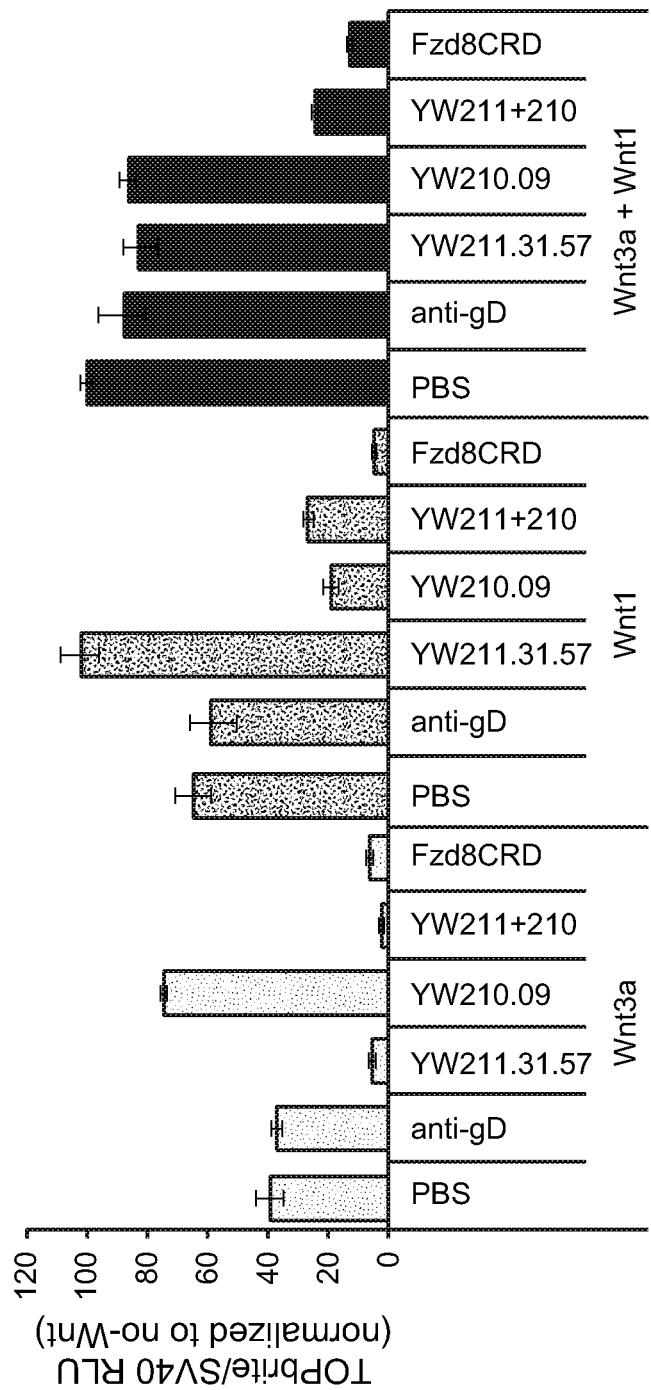
FIG. 8A. Graph showing the combination of YW211.31.57 and YW210.09 antibodies inhibits signaling in HEK293 cells stably integrated with Wnt luciferase reporter that have been transfected for expression of either Wnt3a, Wnt1, or both Wnt3a and Wnt1. Anti-gD antibody and Fzd8CRD-Fc protein are shown as negative and positive controls, respectively, for inhibition of Wnt signaling.

The above assays indicate that Wnt3a and Wnt3 bind within the E1-E2 region of LRP6 and are inhibited from binding by YW211.31.57 antibody. Wnt isoforms in the Wnt1 class are predicted to bind the E3-E4 region, and this binding is blocked by YW210.09 antibody. Without being bound by any one theory, potentiation of Wnt signaling could occur when both a Wnt isoform and an antibody are able to bind the same LRP6 molecule, presumably requiring recruitment of FZD by the Wnt and LRP6 dimerization by the antibody. This model predicts that the combination of both antibodies would inhibit signaling induced by either class of Wnt isoforms since, although LRP6 dimerization would likely still occur, Wnt binding would be blocked by one or the other antibody. As predicted, treating HEK293 cells simultaneously with YW211.31.57 and YW210.09 antibodies inhibits signaling initiated by expression of either Wnt3a or Wnt1 (FIGS. 7 and 8A). The assay shown in FIG. 8A was performed in HEK293 cells stably integrated with Wnt luciferase reporter that have been transfected with expression constructs for either Wnt3a, Wnt1, or both Wnt3a and Wnt1. All antibodies and proteins were used at 10 μg/ml each. This analysis was extended to three other Wnt isoforms in the Wnt1 class and the combination of YW211.31.57 and YW210.09 antibodies was found to inhibit Wnt signaling to a similar extent as YW210.09 alone (FIG. 7). When both Wnt3a and Wnt1 are expressed simultaneously, neither antibody antagonizes Wnt signaling, but the combination of both antibodies does inhibit signaling (FIG. 8A). One possible explanation of this result is that each antibody inhibits binding of only one Wnt isoform, and both antibodies are able to bind LRP6 molecules simultaneously to block both Wnt binding sites.

The four Wnt isoforms in the third class that are not antagonized by YW211.31.57 or YW210.09 antibody might bind to a site on LRP6 not blocked by either antibody or, alternatively, they may have the ability to bind to either of the Wnt-binding sites defined by the antibodies. For each of these Wnt isoforms, the combination of both antibodies also does not inhibit their signaling, but rather potentiates or does not affect their activity, suggesting that these Wnt isoforms can bind a site that is distinct from the YW211.31.57 and YW210.09 epitopes (FIG. 7).

Figure 8B:
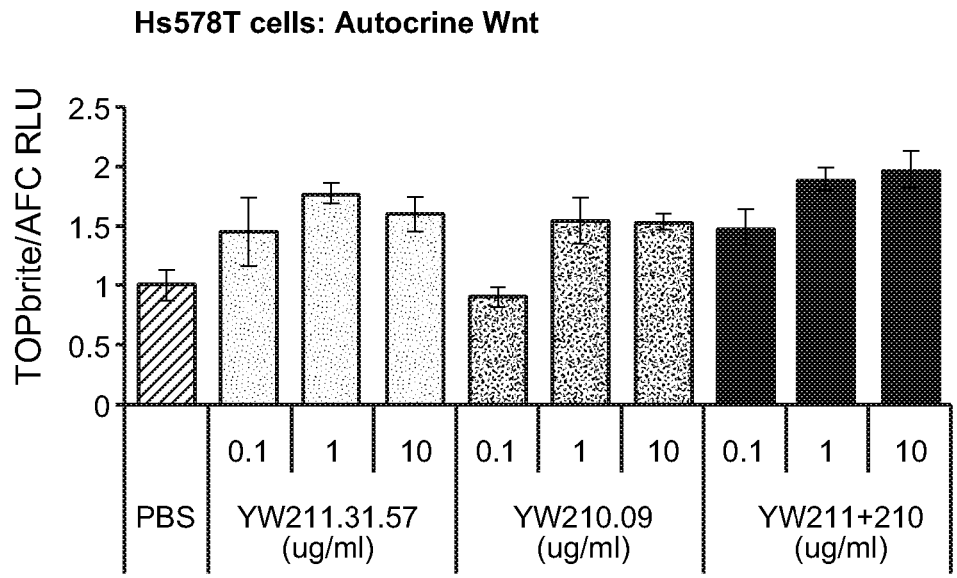
FIG. 8B. Graph showing the combination of YW211.31.57 and YW210.09 antibodies potentiates autocrine Wnt signaling in Hs578T cells.
Figure 8C:
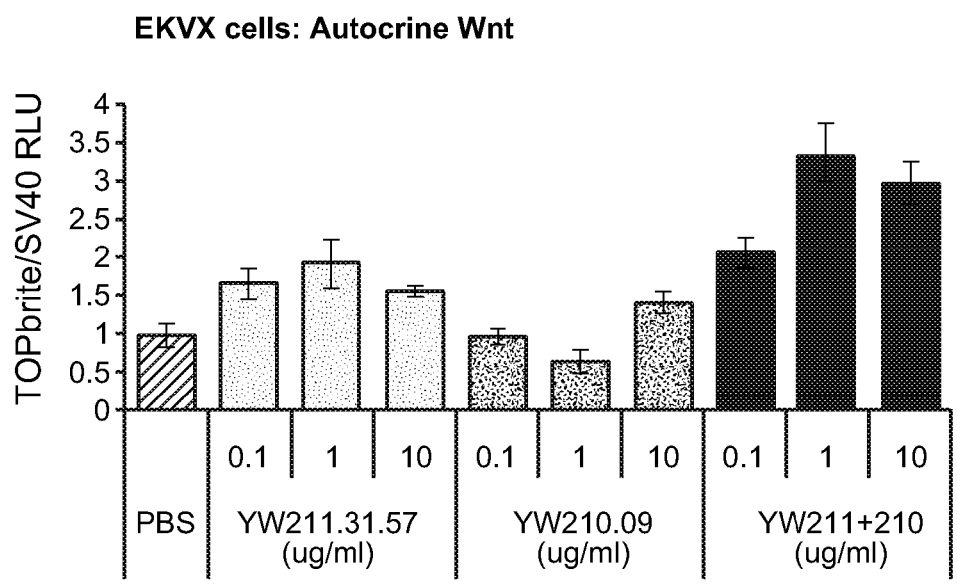
FIG. 8C. Graph showing the combination of YW211.31.57 and YW210.09 antibodies potentiates autocrine Wnt signaling in EKVX cells.

The observed activities of the YW211.31.57 and YW210.09 antibody combination on Wnt signaling induced by exogenous Wnt isoforms also extend to endogenous, autocrine Wnt signaling. In teratocarinoma cell lines PA-1 and Ntera-2, in which YW211.31.57 antibody inhibits and YW210.09 potentiates autocrine Wnt signaling, the antibody combination inhibits signaling (FIG. 2A). In Hs578T and EKVX cells, where both antibodies potentiate autocrine Wnt signaling, the antibody combination also potentiates (FIGS. 8B and 8C).

Example 9

LRP6 Antibodies Differentially Inhibit Wnt Binding to Multiple Sites

Figure 9A:
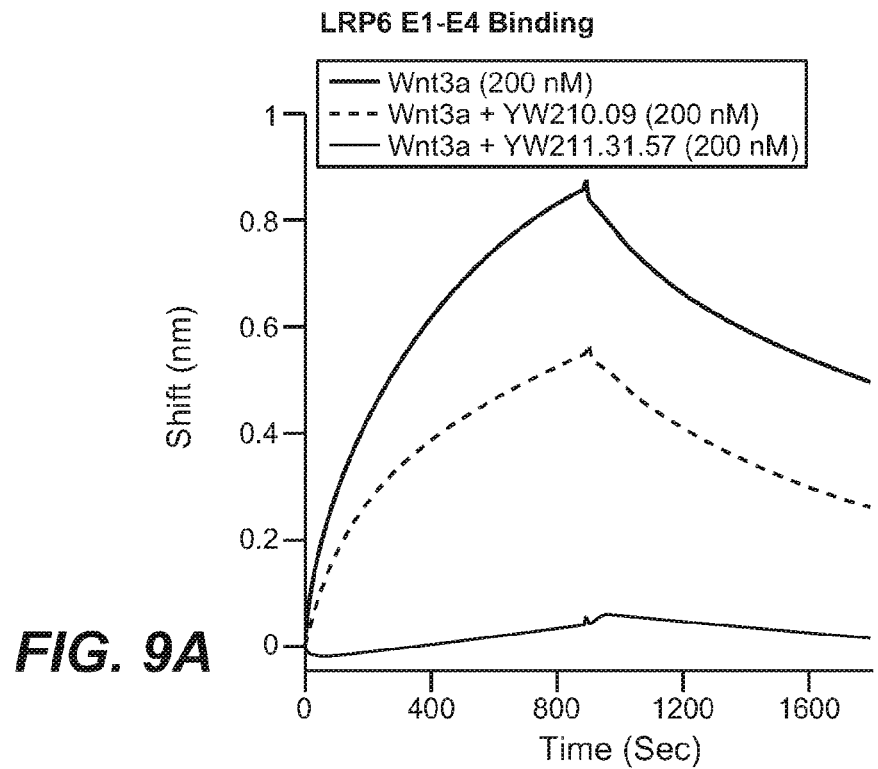
FIGS. 9A and B. Biolayer interferometry assay with biotinylated LRP6 E1-E4 protein immobilized on Streptavidin biosensors indicating that YW211.31.57 antibody inhibits binding of Wnt3a and Wnt9b to LRP6 and YW210.09 antibody inhibits only Wnt9b binding.
Figure 9B:
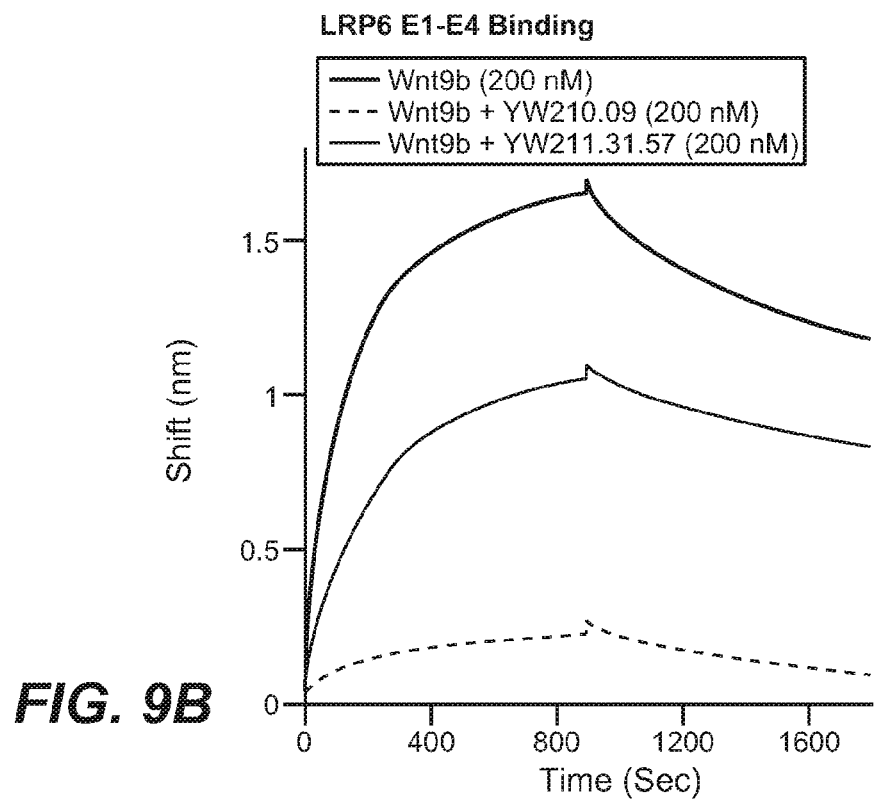
FIG. 9C. Biolayer interferometry assay with smaller, non-overlapping fragment of LRP6 shows that Wnt3a binds to the E3-E4 region, and this interaction is blocked by either the intact or one-armed YW211.31 antibody.
FIG. 9D. Biolayer interferometry assay with smaller, non-overlapping fragment of LRP6 shows that YW210.09 antibody binds the LRP6 E1-E2 protein fragment and competes with Wnt9b binding.
FIG. 9E. Biolayer interferometry assay showing that YW211.31.57 and YW210.09 antibodies can bind together to immobilized LRP6.E1-E4 protein when added sequentially in either order, confirming separate epitopes.

The reciprocal activities of the LRP6 antibodies suggested that YW211.31.57 and YW210.09 interact with distinct Wnt isoform binding sites on LRP6, and that Wnt binding was competed by the antagonist antibody but allowed by the potentiating antibody. A biolayer interferometry assay that measures purified Wnt proteins binding to purified, immobilized LRP6 extracellular domain protein fragments (see Example 1) demonstrated that Wnt3a binds to the E3-E4 region of LRP6, where the epitope for YW211.31.57 antibody resides, and Wnt9b (in the same class as Wnt1 for antibody interactions) binds only to the E1-E2 region, where YW210.09 antibody also binds (Bourhis et al. (2010). YW211.31.57 antibody, but not YW210.09, inhibits binding of Wnt3a to the LRP6.E1-E4 protein fragment (FIG. 9A). Conversely, YW210.09 but not YW211.31.57 inhibits Wnt9b binding to LRP6.E1-E4 (FIG. 9B). In these assays, antibody binding to LRP6 protein was allowed to reach equilibrium, and the subsequent wavelength shift in the interference pattern is shown for association and dissociation phases of Wnt protein binding.

Figure 9C:
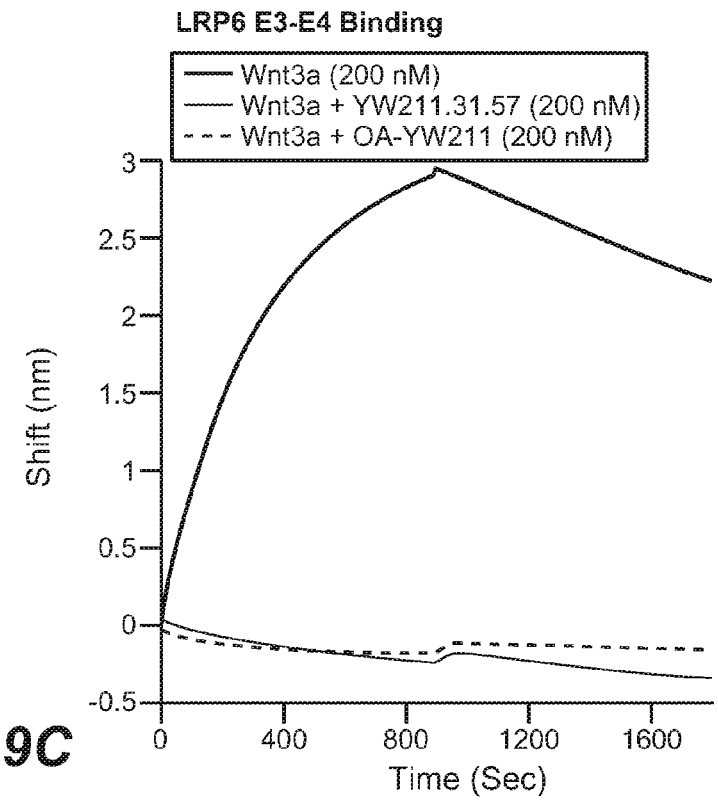
Figure 9D:
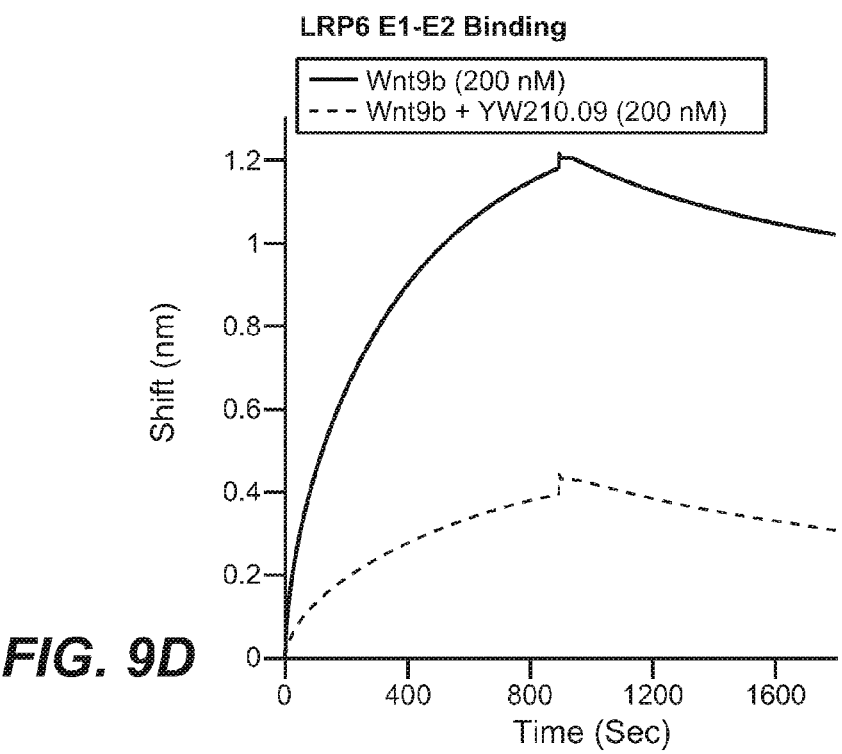
Figure 9E:
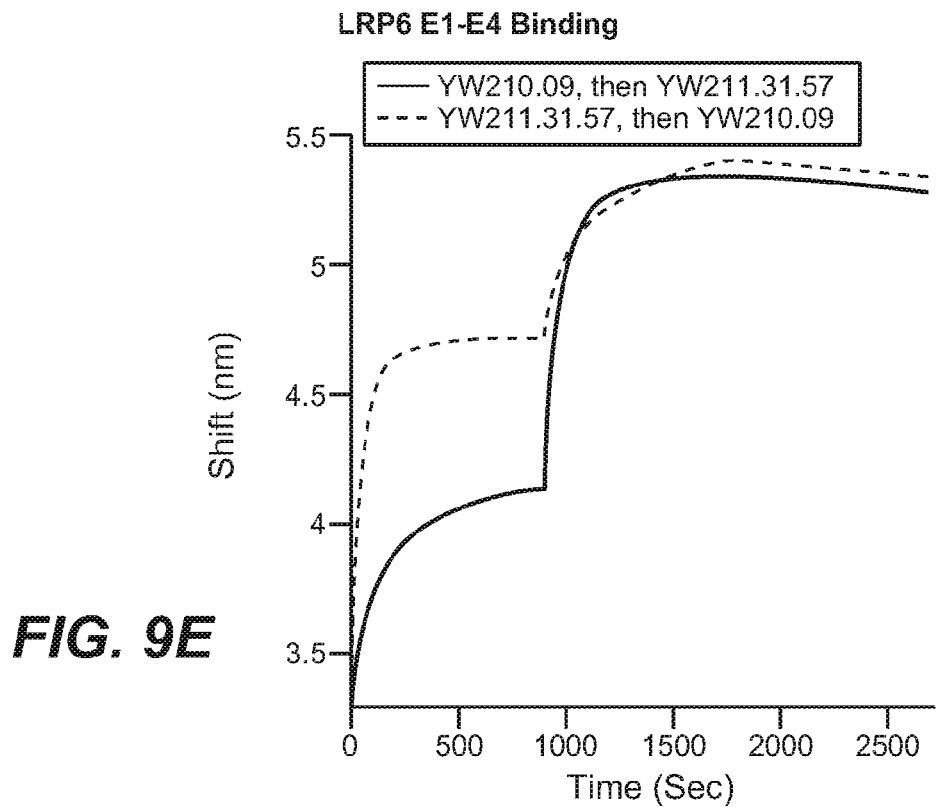

Antibody-mediated inhibition of Wnt binding can also be detected using the smaller Wnt-binding fragments, E3-E4 for Wnt3a and E1-E2 for Wnt9b (FIGS. 9C and 9D). The one-armed YW211.31 antibody can also inhibit Wnt3a binding to the E3-E4 fragment. Also, YW211.31.57 and YW210.09 can be bound sequentially to LRP6.E3-E4 protein without competition and when added in either order (FIG. 9E). Competition for binding between only Wnt3a and YW211.31.57 antibody, and between only Wnt9b and YW210.09, at different sites on LRP6 protein correlate with the inhibitory activity of each antibody against signaling by a specific Wnt isoform.

The biolayer interferometry assay previously showed that purified DKK1 protein could bind both E3-E4 and E1-E2 fragments of LRP6, and that this binding could inhibit binding of Wnt3a and Wnt9b to these respective protein regions. (Bourhis et al. (2010)). This assay was used to show that YW211.31.57 and YW210.09 antibodies can each inhibit DKK1 binding to LRP6.E1-E4 protein). YW211.31.57 antibody also inhibits DKK1 binding to LRP6.E3-E4 protein, and YW210.09 antibody blocks binding of DKK1 to the LRP6.E1-E2 fragment. The one-armed YW211.31 antibody fully retains this inhibitory activity, even though it cannot potentiate Wnt signaling nor significantly antagonize exogenous DKK1 activity on Wnt signaling in cells. This result suggests that DKK1 antagonism likely does not contribute significantly to antibody-mediated potentiation of Wnt signaling.

Example 10

LRP6 Antibodies are Active on Wnt-driven Tumors and Bone Formation

Figure 10A:
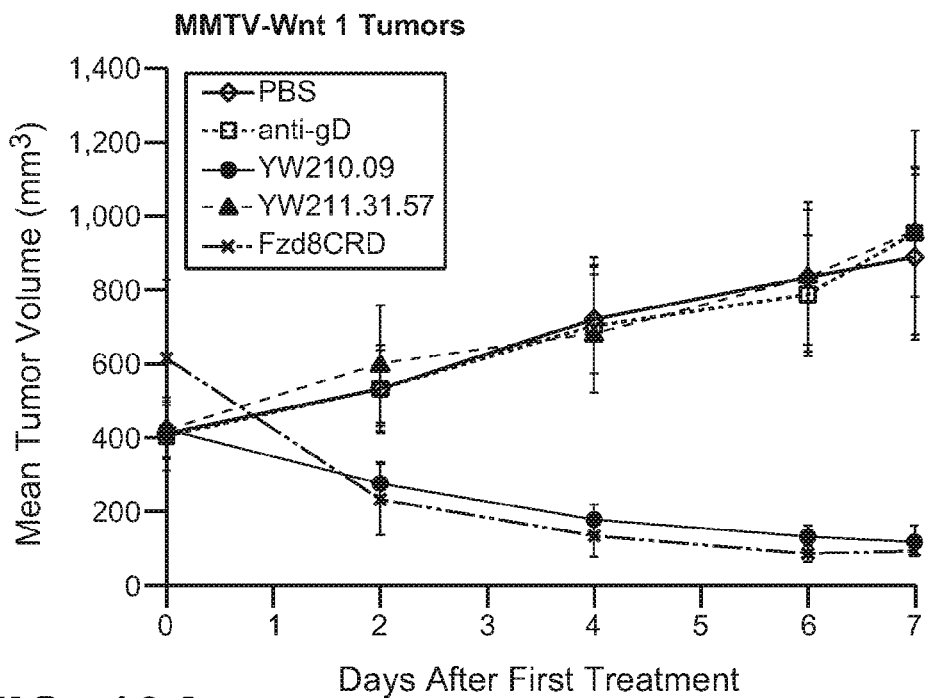
FIG. 10A. Graph showing MMTV-Wnt1 allograft tumors regression of growth when mice are treated with YW210.09 antibody, similar to that observed with Fzd8CRD-Fc protein.

To begin to explore the anti-tumor therapeutic efficacy of the LRP6 antibodies, two models of Wnt ligand-driven tumors were treated. MMTV-Wnt1 transgenic mammary tumor allografts dependent on Wnt1 expression and Ntera-2 human teratocarinoma xenografts driven by autocrine Wnt signaling of an unknown Wnt isoform (DeAlmeida et al., 2007). Cells isolated from MMTV-Wnt1 transgenic mouse mammary tumors were used to establish tumors into athymic nude mice, which were treated with antibody every two days. Rapid and sustained tumor regression was observed with YW210.09 antibody, similar to Fzd8CRD-Fc protein (FIG. 10A). YW211.31.57 antibody did not alter tumor growth under these conditions compared to control buffer (PBS) or anti-gD antibody treatment. Mice were administered 30 mg/kg of antibody or protein every two days (arrowheads) (FIG. 10A). These results are consistent with the antibody effects described above on Wnt target gene expression for MMTV-Wnt1 tumor cells treated in tissue culture.

Figure 10B:
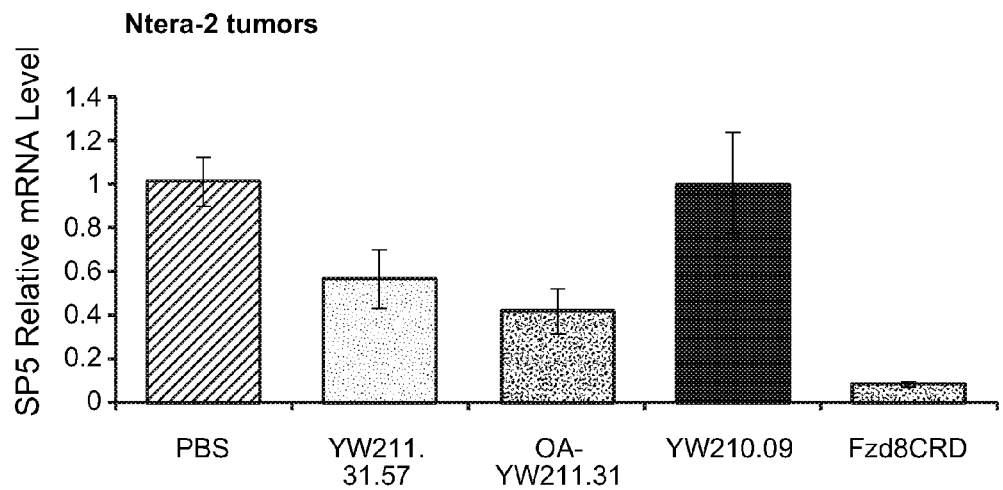
FIG. 10B. Graph showing Ntera-2 xenograft tumors display reduced expression of SP5 mRNA by qPCR analysis in mice treated with intact or one-armed YW211.31 antibody, but not with YW210.09 antibody.

Ntera-2 teratocarinoma cells were also used to establish xenograft tumors in athymic nude mice, which were treated with either antibody or Fzd8CRD-Fc protein. RNA extracted from tumors treated with antibodies YW211.31.57, one-armed YW211.31, or the combination of YW211.31.57 and YW210.09 reveals reduced expression of Wnt target gene SP5 to 41-57% the level of tumors from buffer-injected control mice, whereas Fzd8CRD-Fc protein treatment reduced SP5 expression to 8.0%. SP5 mRNA levels were normalized to GAPDH mRNA levels within the same tumor, and additionally normalized to PBS-treated tumors. All treatments except YW210.09 display p-value <0.005 by ANOVA compared to PBS control. (FIG. 10B). Axin2 expression was reduced to only 56.2% by Fzd8CRD-Fc, and no significant changes in Axin2 expression were detected with any of the antibody treatments. YW210.09 antibody treatment did not significantly affect expression of either SP5 or Axin2. Serum samples assayed for inhibition or potentiation of Wnt3a-induced signaling in HEK293 cells confirm that injected antibodies and protein retained at least some activity in vivo throughout the 16-h exposure.

Figure 10C:
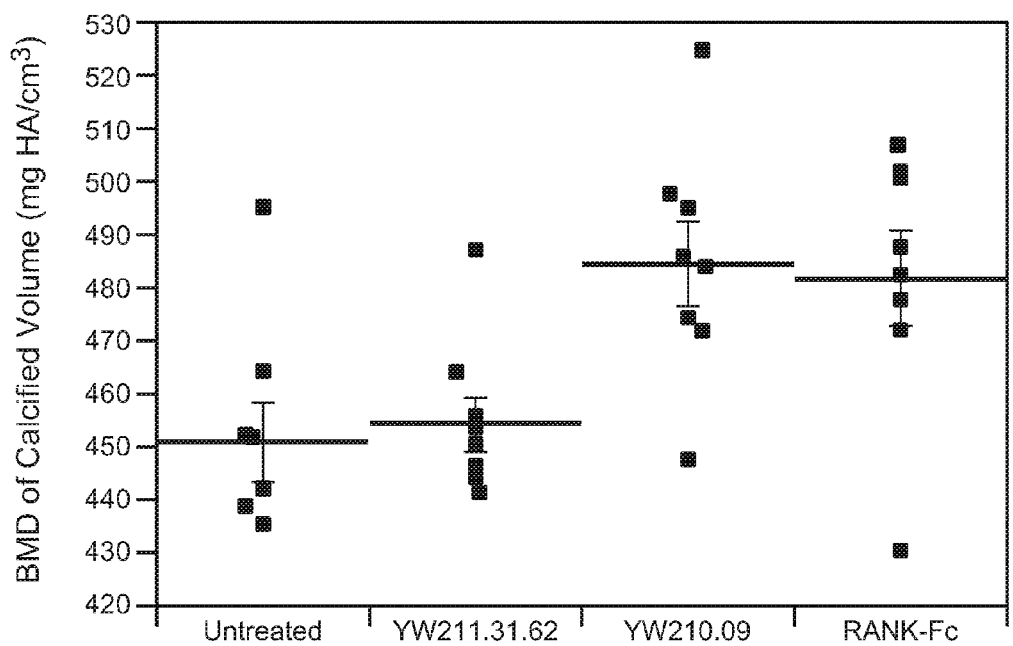
FIG. 10C. Graph showing YW210.09, but not YW211.31.62, antibody treatment of mouse calvaria explants in culture significantly increases bone mineral density (BMD) of calcified parietal bone, similar to treatment with RANK-Fc protein.

Since activation or potentiation of Wnt signaling can increase bone mass by enhancing osteoblast differentiation and function and, indirectly, by inhibiting osteoclast differentiation (Glass et al., 2005), the activity of LRP6 antibodies on mouse calvarial bones in organotypic culture was tested. Microdissected calvaria explants were cultured with antibody or RANK-Fc, and then parietal bone volume and density were analyzed by micro-computed tomography. Using histogram analysis of control samples, X-ray attenuation ranges were defined for calcified (bone) and non-calcified (cartilage) tissues. Treatment with YW210.09 antibody significantly increased the mean bone mineral density (BMD) of calcified parietal bone by 7.4%, similar to the 6.8% increase observed with RANK-Fc treatment to inhibit osteoclast differentiation (FIG. 10C; Hsu et al., 1999). Treatment with YW211.31.62 antibody did not significantly change calcified parietal BMD. All treatments were 10 µg/ml antibody or protein for 7 days. In FIG. 10C, data points represent eight calvaria halves from four mice for each treatment group; mean and standard error of the mean are shown as horizontal and vertical lines, respectively. Only YW210.09 and RANK-Fc treatments differ significantly from untreated samples with p-values less than 0.01 and 0.05, respectively, by Dunnett's test (<0.05 for both by t-test).

The volume of total parietal bone region (calcified and non-calcified) and the proportion of calcified bone in this region were not significantly changed by antibody or RANK-Fc treatments, suggesting that YW210.09 antibody may enhance mineralization without gross changes in cell proliferation.

Example 11

LRP6 Bispecific Antibody Acts as a Pan-Wnt Inhibitor

Figure 11A:
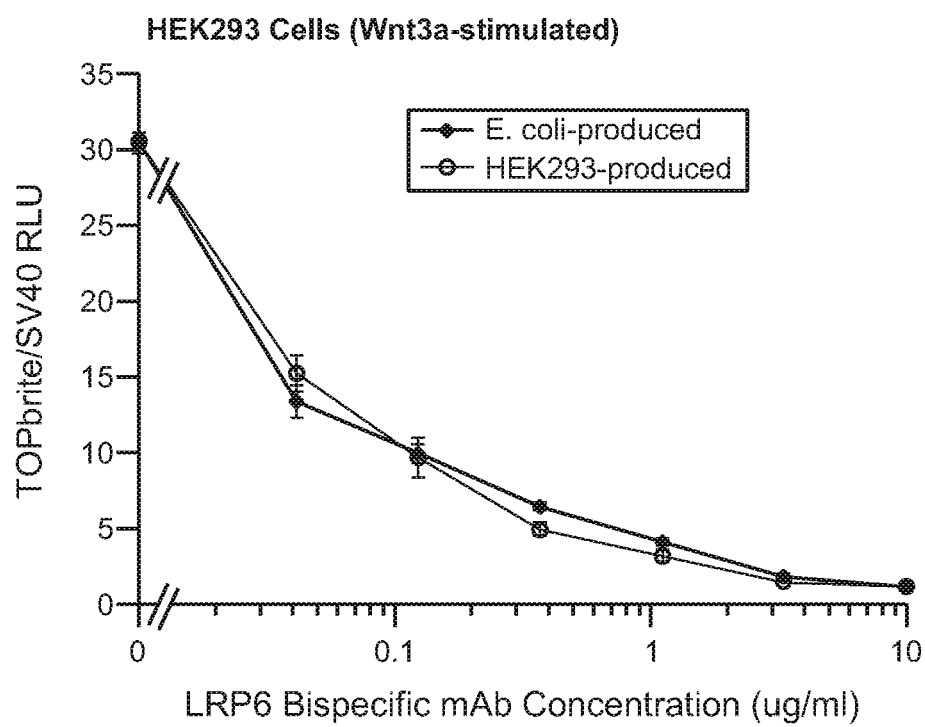
FIG. 11A. Graph showing bispecific anti-LRP6 antibody produced in *E. coli* or HEK293 cells similarly inhibits in a concentration-dependent manner the Wnt luciferase reporter activity in HEK293 cells induced with 0.1 μg/ml purified Wnt3a. $IC_{50}$ values are 0.032 and 0.014 μg/ml, respectively.
Figure 11B:
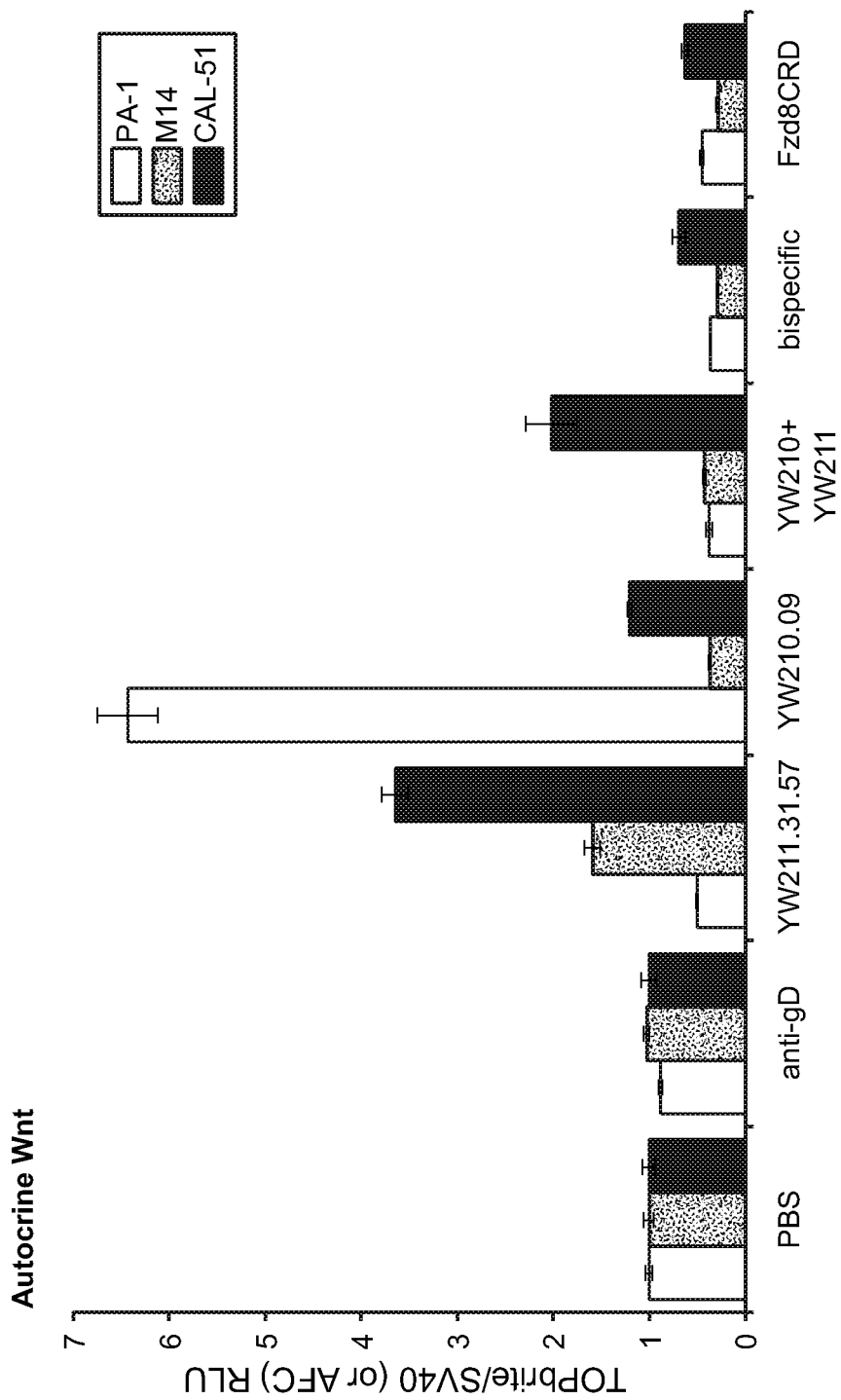
Figure 11C:
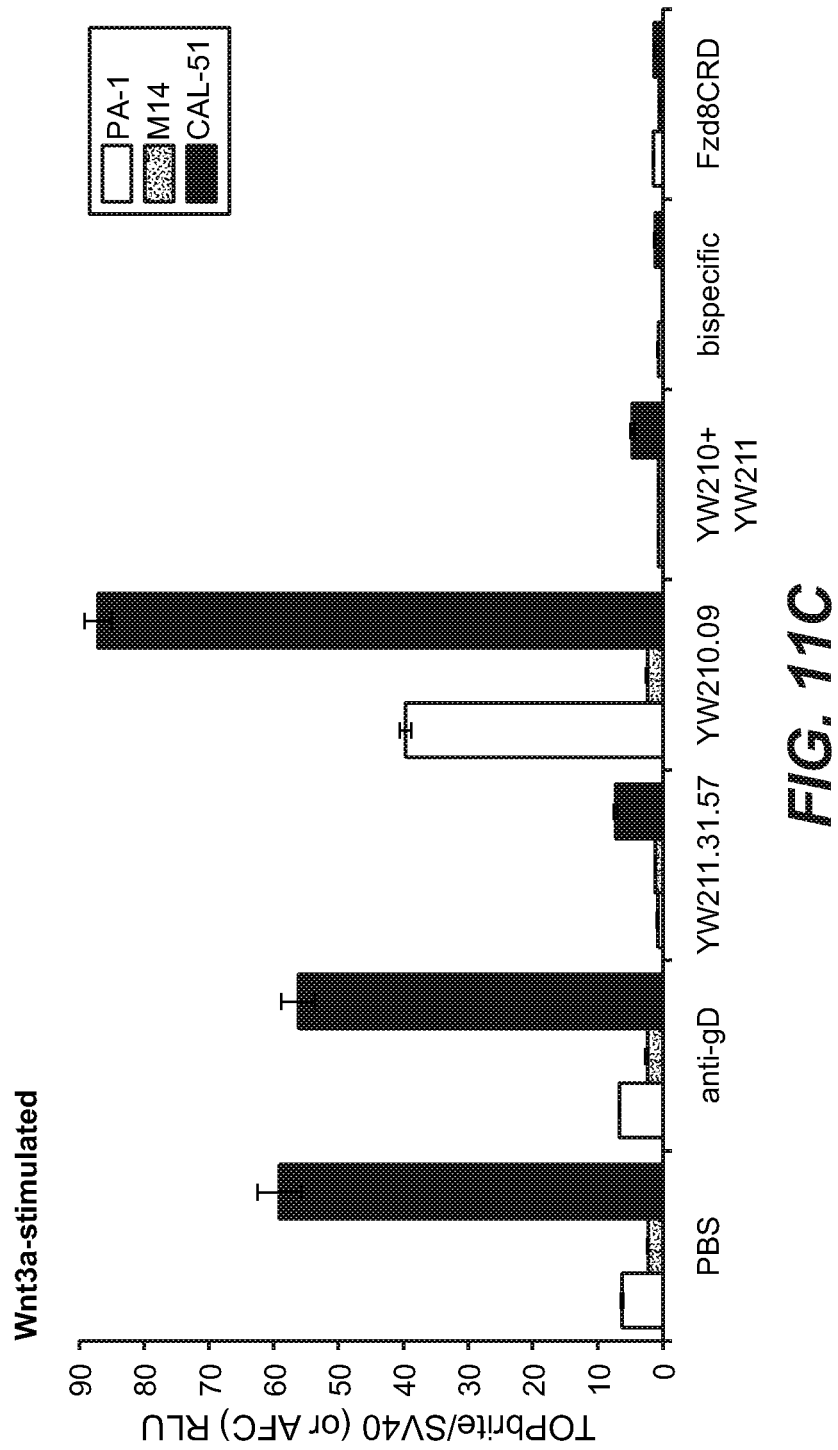

Knobs-into-holes engineering (Atwell et al., 1997) was used to construct a bispecific IgG hybrid with YW211.31.62 and YW210.09 heavy chain heterodimers. This LRP6 bispecific antibody, produced in either *E. coli* or HEK293 cells, antagonizes Wnt3a-induced (0.1 µg/ml) signaling in HEK293 cells (FIG. 11A) and tumor cell lines PA-1, M14, and CAL-51 (FIG. 11C). Notably, the bispecific antibody inhibits at least as potently as YW211.31 and does not retain the Wnt3a-potentiating activity of YW210.09. The bispecific antibody also inhibits autocrine Wnt signaling in all three tumor cell lines tested (FIG. 11B), preserving the inhibitory activity of YW211.31 antibody in PA-1 cells and of YW210.09 in M14 cells. Interestingly, even though YW211.31 potentiates and YW210.09 has no effect on autocrine Wnt signaling in CAL-51 breast carcinoma cells, the bispecific antibody inhibits signaling. This novel antagonistic activity is not observed with the combination of YW211.31 and YW210.09 antibodies. In the above assays, PA-1 and M14 cells stably integrated with Wnt luciferase reporter, and CAL-51 cells transfected with reporter, were treated with the indicated control buffer (PBS), antibody, antibody combination, or Fzd8CRD-Fc protein (10 µg/ml each) with (11C) or without (11B) stimulation by 0.1 µg/ml Wnt3a.

When tested on signaling induced by transfection of 13 Wnt isoforms in HEK293 cells, the bispecific antibody potently inhibits all Wnts that are blocked by either YW211.31 or YW210.09 (FIG. 12). The assays summarized in Table 12 determined the effects of antibodies or protein (10 µg/ml) on signaling induced by transfection of expression constructs for Wnt isoforms in HEK293 or Hs578T cell lines stably integrated with Wnt luciferase reporter. Reporter activity was normalized to cell number and additionally normalized to the level in cells transfected with the same expression construct but not treated with antibody or protein. Anti-gD was used as a control. Fold-change values were considered to be relevant when they were outside the range observed with control anti-gD antibody treatment: less than 0.80 for inhibition and greater than 1.30 for potentiation in HEK293 cells, and less than 0.65 for inhibition and greater than 1.30 for potentiation in Hs578T cells.

Similar to the combination of YW211.31 and YW210.09 antibodies, and unlike either antibody alone, the bispecific antibody blocks signaling induced by the combination of Wnt1 and Wnt3a (FIG. 12). Unexpectedly, the bispecific antibody also reduces signaling by the three Wnts that are not inhibited by the homodimeric antibodies alone or in combination. These antagonistic activities of the bispecific antibody are also observed in Hs578T cells, with the possible exception of a lack of effect on Wnt7a-induced signaling.

Figure 13A:
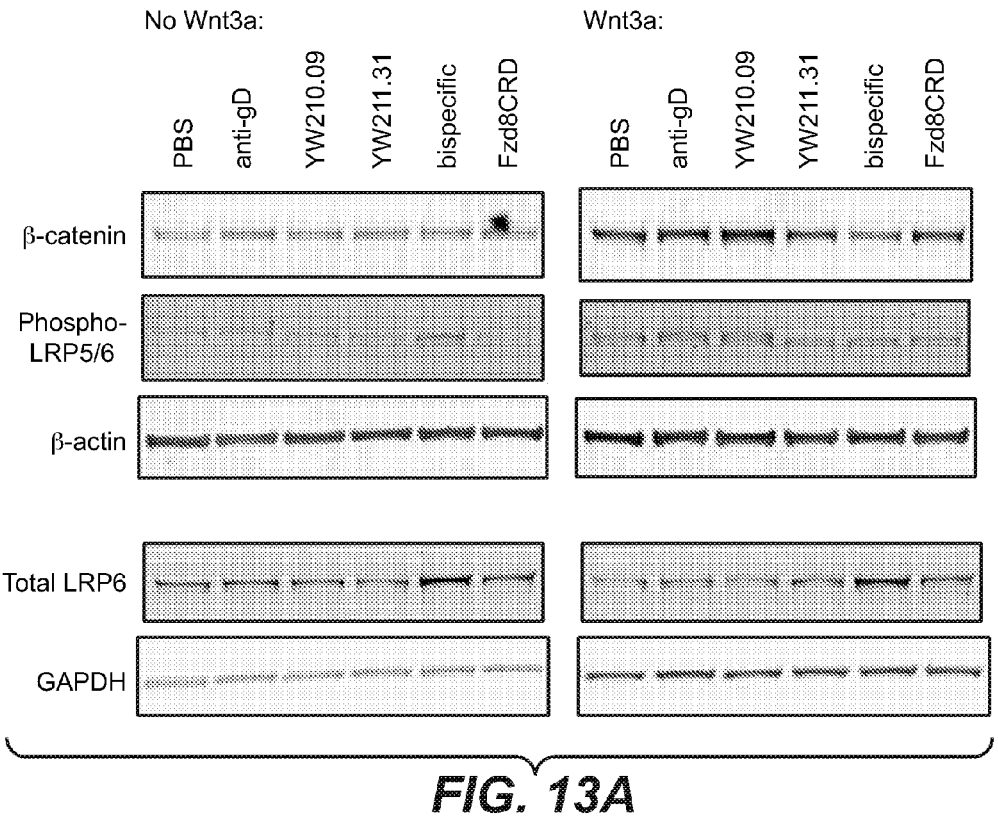
FIG. 13A. Western analysis of HEK293 cells with or without Wnt3a transfection and treated with the indicated antibody or Fzd8CRD-Fc protein (5 μg/ml) for 18 h. β-actin or GAPDH protein levels are shown as sample loading controls for the upper and lower gels, respectively.

The ability of the bispecific antibody to inhibit Wnt3a-induced stabilization of β-catenin protein was examined HEK293 cells with or without Wnt3a transfection were treated with YW211.31, YW210.09, or the bispecific antibody, or with controls Fzd8CRD-Fc protein or anti-gD, at a concentration of 5 µg/ml for 18 h and the β-catenin protein levels and phosphorylated LRP5/6 levels were determined by Western blot analysis. FIG. 13A. In HEK293 cells, the bispecific antibody inhibits Wnt3a-induced stabilization of β-catenin protein, similar to YW211.31 and unlike YW210.09 which increases β-catenin levels (FIG. 13A). Both the bispecific and YW211.31, but not YW210.09, antibody block induction by Wnt3a of a high-molecular-weight species of phosphorylated LRP5/6. Surprisingly, while YW211.31 and YW210.09 do not affect steady state levels of total LRP6 protein, the bispecific antibody increases LRP6 protein with or without Wnt3a induction. In the absence of Wnt stimulation, this stabilized LRP6 may have slightly increased Ser1490 phosphorylation, although the bispecific antibody does not affect Wnt reporter activity in HEK293 cells in the absence of Wnt.

Figure 13B:
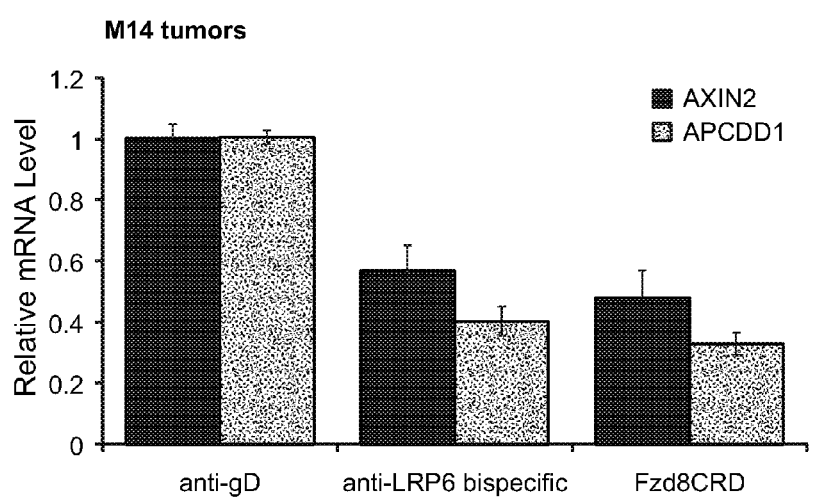
FIG. 13B. Graph showing M14 xenograft tumors in SCID-bg mice treated 16 h with 30 mg/kg LRP6 bispecific antibody or Fzd8CRD protein, but not with control anti-gD antibody, display reduced expression of AXIN2 and APCDD1 mRNA by qPCR analysis.

The bispecific antibody's ability to inhibit Wnt signaling in vivo was also determined SCID-bg mice with M14 melanoma xenograft tumors were injected with 30 mg/kg LRP6 bispecific antibody, Fzd8CRD protein (positive control), or anti-gD antibody (negative control). After 16 hours of treatment, RNA was extracted and examined by qPCR for expression of Wnt target genes. mRNA levels were normalized to GAPDH mRNA levels within the same tumor, and additionally normalized to anti-gD-treated tumors. All bispecific antibody and Fzd8CRD treatments display p-values <0.001 by ANOVA compared to anti-gD control. As shown in FIG. 13B, the LRP6 bispecific antibody inhibited Wnt signaling in the M14 melanoma cells grown as xenograft tumors. RNA extracted from tumors treated with the antibody show reduced expression of Wnt target genes AXIN2 and APCDD1 to 46-57% and 35-38%, respectively, of the levels in tumors treated with control anti-gD antibody. These reduced expression levels are similar to those observed with injection of Fzd8CRD protein, and indicate that the bispecific antibody is stable and active in vivo.

Example 12

Structure of the LRP6 E1-YW210.09 Fab Complex

The crystal structure of the first β-propeller and EGF domain of LRP6 (also called E1) in complex with YW210.09 Fab was determined by molecular replacement and refined to 1.9 Å resolution with an R and Rfree of 0.175 and 0.220 respectively. The crystallographic asymmetric unit is composed of one LRP6 E1 domain and one YW210.09 Fab. Interpretable electron density allowed tracing of the residues Ala 20 to Lys 324 for the E1 domain and, residues Asp 1 to Glu 213 and Glu 1 to Lys 214 for the Fab light chain and heavy chain respectively, with the exception of Fab heavy chain residues Ser 127 to Thr 131 (Kabat numbering is used throughout).

The LRP6 E1 domain is assembled in a modular architecture that comprises β-propeller module and an epidermal growth factor (EGF) like module. The β-propeller consists of six blades formed by a four-stranded anti-parallel β-sheet arranged radialy with the N-terminal edge facing the center channel and the YWTD motifs located in the second strand of each blade. The LRP6 E1 β-propeller structure closely resembles that of LDLr (Jeon, H., et al., 2001) with an rmsd of 0.83 Å when superimposed over 245 C-α atoms despite a sequence identity of only 36%. Most of the conserved residues are concentrated around the YWTD core motifs forming the β-sheets, essential to the β-propeller structure integrity whereas the surface residues are highly diverse contributing to the functional diversity of these receptors. LRP6 uses its EGF like domain to lock down the first and sixth blades of the propeller and maintain its mechanical strength. The EGF like module extends out C-terminally from the β-propeller via a ten-residue linker and folds back on to the bottom side of β-propeller, docking to a surface between the third and forth blades. The interaction between EGF and β-propeller is extensive as indicated by the large total buried surface area of 1226 Å2, and shape complimentarily of 0.74. Three residues, Leu 296, Leu 298 and Met 299, in the first β-strand of the EGF module constitute a hydrophobic core that packs into a complementary cavity of the β-propeller, surrounded by some direct or water mediated polar interactions. These features are also observed in the LDLR structures (Jeon, H., et al., 2001); Rudenko, G., et al., 2002).

Figure 14:
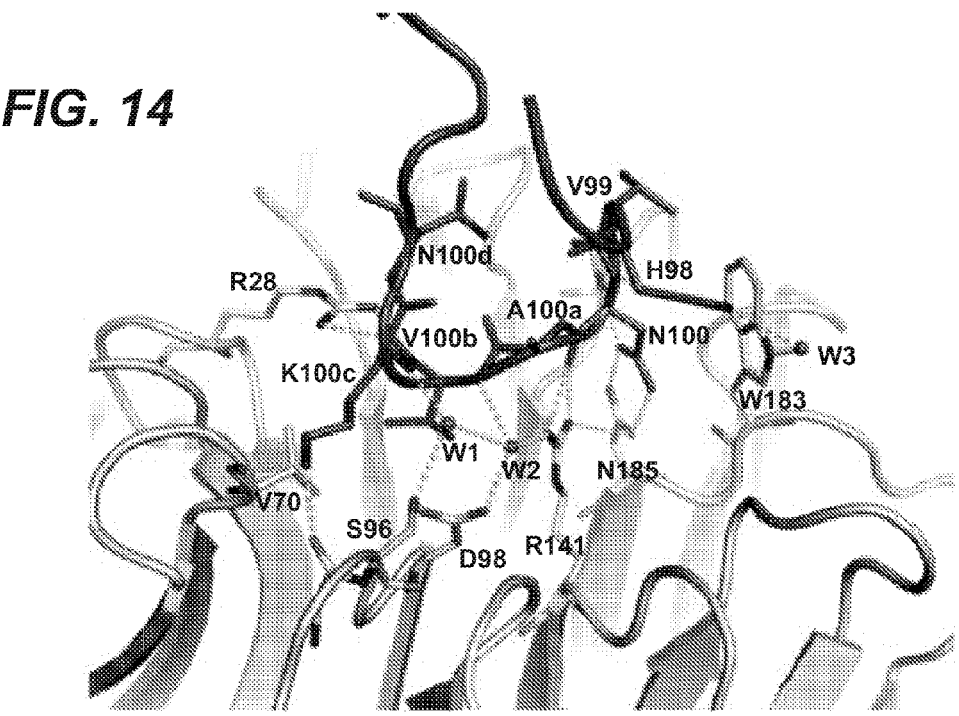
FIG. 14. Detailed view of the CDR H3 interaction with residues of the LRP6 groove which shows the important network of interaction made by the NAVK motif FIG. 15. Detail of the interaction made by CDR H1,2, L1,2 and 3.
Figure 15:
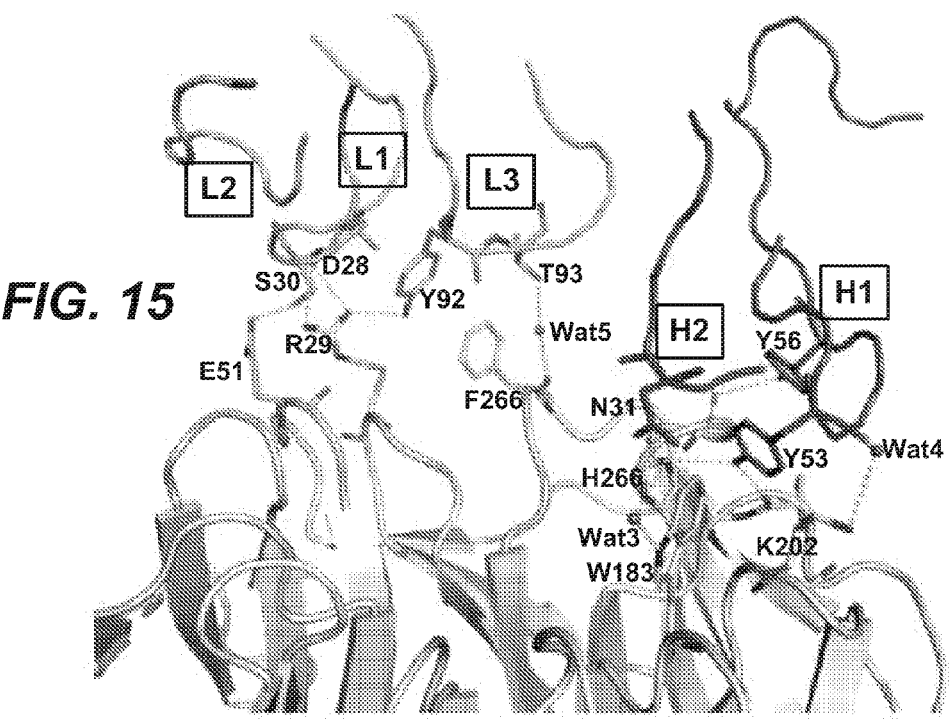

YW210.09 Fab recognizes a region at the top center of the β-propeller, an area that is frequently found to be involved in protein-protein interactions (Springer, T. A., 1998). The paratope is composed of residues from five of the CDRs, including three heavy chain CDRs (H1, H2, H3) and two light chain CDRs (L1 and L3). Antibody binding to the β-propeller buried a total area of 1691 Å2 with a shape complementarity score of 0.76. An acidic patch on the top face of the β-propeller occupies roughly a third of the total area but barely overlaps with the YW210 epitope. On the contrary, heavy chain and light chain recognize discrete areas. Direct contacts formed by the heavy chain CDRs represent 80% of the buried area with CDR H3 alone accounting for over 50%. This segment is composed of 17 residues, among which residues H is 98 to Lys 100c form direct contacts with the β-propeller. Importantly, Asn 100 of the antibody makes a pair of hydrogen bonds with Asn 185 of LRP6 forming a "hand shake" interaction (FIG. 16). In addition, Val 100b and Lys 100c main chains unusual conformation position a carbonyl group that interacts with Arg 28 of LRP6 in the back, and two NH groups which interact with the acidic patch through two water molecules (Wat1 and Wat2) in the front (FIG. 14). Lys 100c side chain also neutralizes the acidic patch by hydrogen bonding with Val 70 and Ser 96 main chain carbonyls of LRP6. Arg 141 of LRP6 is anchored in the middle and interacts with the bridging water Wat2, Asn 185 of LRP6, and Ala 100a of YW210.09. Arg 141 appears to integrate the two hydrogen bond networks together. Additionally, Val 100b side chain docks into a hydrophobic cavity in the center channel of the β-propeller. Therefore, the YW210.09 H3 sequence NAVK exhibits extraordinary binding pattern with the β-propeller E1 of LRP6. The other CDRs interact with residues in the parameters on the top of the β-propeller. Other residues involved in the H3 binding to LRP6 include E51, D52, V70, S71, E73, L95, S96, D98, and E115. H1 and H2 touch the fifth and sixth blades, while L1 and L3 touch the sixth, the first, and the second blades (FIG. 15). Additional LRP6 residues involved binding of YW210.09 to LRP6 include R29, W188, K202, P225, H226, S243, and F266. Crystal packing interactions are not directly involved in the areas where the YW210.09 contacts the LRP6 epitope, indicating that the crystal structure should reflect how the two molecules interact in solution. The interaction between the distinct CDR H3NAVKN (SEQ ID NO: 49) motif and LRP6 E1 β-propeller is highly similar to the interaction reported between Laminin and Nidogen (Takagi, J., et al., 2003). In both cases, significant contacts are made through the Asn handshake described above and a branched hydrophobic residue entering a hydrophobic cavity formed by the top of β-propeller center channel which is closed in both propellers by a Phe shutter. Human Dkk1 presents a motif (Amino acids 40 to 44: NAIKN (SEQ ID NO: 50)) which is, besides its Ile 42, identical to the motif found in the CDR H3 loop of YW210.09. This motif is strictly conserved among species and family members besides Dkk3, pointing toward a specific function for this motif in Dkks biology. The conserved motif is found on the N-terminus of Dkk1, a region which has not been considered before (Brott, B. K., and Sokol, S. Y., 2002) and predicted to be disordered. Additionally, this particular motif is also conserved in the two other proteins regulating Wnt signaling via interaction with LRP5/6 namely Sclerostin (Semenov, M., et al., 2005) and Wise (Itasaki, N., et al., 2003). These two proteins belong to the same super-family of cysteine knot proteins (McDonald, N. Q., and Hendrickson, W. A., 1993) and display the identified motif in their loop number 2, also called the "heel" of this conserved fold (Lintern, K. B., et al., 2009; Veverka, V., et al, 2009).

Example 13

Exemplary Anti-LRP6 Antibodies

The amino acid sequences of certain anti-LRP6 antibodies are provided in the Sequence Listing. Tables 2-4 provide a description of the sequences. Alignments of the amino acid sequences of the VH and VL domains of specific anti-LRP6 antibodies are provided in FIGS. 16 and 17.

TABLE 2

Heavy and Light Chains

| SEQ ID | Description |
| --- | --- |
| SEQ ID NO: 1 | YW211.31 Heavy Chain |
| SEQ ID NO: 2 | YW211.31 Light Chain |
| SEQ ID NO: 3 | YW211.31.57 Heavy Chain |
| SEQ ID NO: 4 | YW211.31.57 Light Chain |
| SEQ ID NO: 5 | YW211.31.62 Heavy Chain |
| SEQ ID NO: 6 | YW211.31.62 Light Chain |
| SEQ ID NO: 7 | YW210.09 Heavy Chain |
| SEQ ID NO: 8 | YW210.09 Light Chain |

TABLE 3

Heavy and Light Chain Variable Regions

| SEQ ID | Description |
| --- | --- |
| SEQ ID NO: 9 | YW211.31 Heavy Chain Variable Region |
| SEQ ID NO: 10 | YW211.31; YW211.03; YW211.08; YW211.11; YW211.12; YW211.33; YW211.31.35 Light Chain Variable Region |
| SEQ ID NO: 11 | YW211.31.57 Heavy Chain Variable Region |
| SEQ ID NO: 12 | YW211.31.57 Light Chain Variable Region |

TABLE 3-continued

Heavy and Light Chain Variable Regions

| SEQ ID | Description |
|---|---|
| SEQ ID NO: 13 | YW211.31.62 Heavy Chain Variable Region |
| SEQ ID NO: 14 | YW211.31.62 Light Chain Variable Region |
| SEQ ID NO: 15 | YW210.09 Heavy Chain Variable Region |
| SEQ ID NO: 16 | YW210.09 Light Chain Variable Region |
| SEQ ID NO: 51 | YW211.03 Heavy Chain Variable Region |
| SEQ ID NO: 52 | YW211.08 Heavy Chain Variable Region |
| SEQ ID NO: 53 | YW211.11 Heavy Chain Variable Region |
| SEQ ID NO: 54 | YW211.12 Heavy Chain Variable Region |
| SEQ ID NO: 55 | YW211.33 Heavy Chain Variable Region |
| SEQ ID NO: 56 | YW211.31.11 Heavy Chain Variable Region |
| SEQ ID NO: 57 | YW211.31.35 Heavy Chain Variable Region |
| SEQ ID NO: 58 | YW211.31.11 Light Chain Variable Region |

TABLE 4

Heavy and Light Chain HVRs

| SEQ ID NO: 17 | YW211.31 HVR-H1; YW211.31.57 HVR-H1 |
|---|---|
| SEQ ID NO: 18 | YW211.31 HVR-H2; YW211.31.57 HVR-H2; YW211.31.62 HVR-H2 |
| SEQ ID NO: 19 | YW211.31 HVR-H3; YW211.31.62 HVR-H3 |
| SEQ ID NO: 20 | YW211.31.62 HVR-H1 |
| SEQ ID NO: 21 | YW211.31.57 HVR-H3 |
| SEQ ID NO: 22 | YW210.09 HVR-H1 |
| SEQ ID NO: 23 | YW210.09 HVR-H2 |
| SEQ ID NO: 24 | YW210.09 HVR-H3 |
| SEQ ID NO: 25 | YW211.31 HVR-L1; YW211.31.57 HVR-L1; YW211.31.62 HVR-L1; YW210.09 HVR-L1 |
| SEQ ID NO: 26 | YW211.31 HVR-L2; YW211.31.57 HVR-L2; YW211.31.62 HVR-L2; YW210.09 HVR-L2 |
| SEQ ID NO: 27 | YW211.31 HVR-L3; YW211.31.62 HVR-L3; YW210.09 HVR-L3 |
| SEQ ID NO: 28 | YW211.31.57 HVR-L3 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

REFERENCES

Adams C, Totpal K, Lawrence D, Marsters S, Pitti R, Yee S, Ross S, Deforge L, Koeppen H, Sagolla M, Compaan D, Lowman H, Hymowitz S, Ashkenazi A. Structural and functional analysis of the interaction between the agonistic monoclonal antibody Apomab and the proapoptotic receptor DR5. Cell Death Differ. 2008 April; 15(4):751-61. Epub 2008 Jan. 25.

Akiri G, Cheman M M, Vijayakumar S, Liu G, Bafico A, Aaronson S A. Wnt pathway aberrations including autocrine Wnt activation occur at high frequency in human non-small-cell lung carcinoma. Oncogene. 2009 May 28; 28(21):2163-72. Epub 2009 Apr. 20.

Bafico A, Liu G, Goldin L, Harris V, Aaronson S A. An autocrine mechanism for constitutive Wnt pathway activation in human cancer cells. Cancer Cell. 2004 November; 6(5): 497-506.

Bilic J, Huang Y L, Davidson G, Zimmermann T, Cruciat C M, Bienz M, Niehrs C. Wnt induces LRP6 signalosomes and promotes dishevelled-dependent LRP6 phosphorylation. Science. 2007 Jun. 15; 316(5831):1619-22.

Binnerts M E, Tomasevic N, Bright J M, Leung J, Ahn V E, Kim K A, Zhan X, Liu S, Yonkovich S, Williams J, Zhou M, Gros D, Dixon M, Korver W, Weis W I, Abo A. The first propeller domain of LRP6 regulates sensitivity to DKK1. Mol Biol Cell. 2009 August; 20(15):3552-60. Epub 2009 May 28.

Bourhis E, Tam C, Franke Y, Bazan J F, Ernst J, Hwang J, Costa M, Cochran A G, Hannoush R N. Reconstitution of a Frizzled8-Wnt3a-LRP6 Signaling Complex Reveals Multiple Wnt and Dkk1 Binding Sites on LRP6. J Biol. Chem. 2010 Mar. 19; 285(12):9172-9. Epub 2010 Jan. 21.

Brott, B. K., and Sokol, S. Y. (2002) Mol Cell Bio122, 6100-6110.

Cho S J, Valles Y, Giani VC J r, Seaver E C, Weisblat D A. Evolutionary dynamics of the Wnt gene family: a lophotrochozoan perspective. Mol Biol Evol. 2010 Feb. 22. [Epub ahead of print]

Cong F, Schweizer L, Varmus H. Wnt signals across the plasma membrane to activate the beta-catenin pathway by forming oligomers containing its receptors, Frizzled and LRP. Development. 2004 October; 131(20):5103-15.

Cselenyi C S, Jernigan K K, Tahinci E, Thorne C A, Lee L A, Lee E. LRP6 transduces a canonical Wnt signal independently of Axin degradation by inhibiting GSK3's phosphorylation of beta-catenin. Proc Natl Acad Sci USA. 2008 Jun. 10; 105(23):8032-7. Epub 2008 May 28.

Cunningham S A, Stephan C C, Arrate M P, Ayer K G, Brock T A. Identification of the extracellular domains of Flt-1 that mediate ligand interactions. Biochem Biophys Res Commun. 1997 Feb. 24; 231(3):596-9.

Davis-Smyth T, Chen H, Park J, Presta L G, Ferrara N. The second immunoglobulin-like domain of the VEGF tyrosine kinase receptor Flt-1 determines ligand binding and may initiate a signal transduction cascade. EMBO J. 1996 Sep. 16; 15(18):4919-27.

DeAlmeida V I, Miao L, Ernst J A, Koeppen H, Polakis P, Rubinfeld B. The soluble wnt receptor Frizzled8CRD-hFc inhibits the growth of teratocarcinomas in vivo. Cancer Res. 2007 Jun. 1; 67(11):5371-9.

Glass D A 2nd, Bialek P, Ahn J D, Starbuck M, Patel M S, Clevers H, Taketo M M, Long F, McMahon A P, Lang R A, Karsenty G. Canonical Wnt signaling in differentiated osteoblasts controls osteoclast differentiation. Dev Cell. 2005 May; 8(5):751-64.

Guo Y, Xie J, Rubin E, Tang Y X, Lin F, Zi X, Hoang B H. Frzb, a secreted Wnt antagonist, decreases growth and invasiveness of fibrosarcoma cells associated with inhibition of Met signaling. Cancer Res. 2008 May 1; 68(9):3350-60.

Hsu H, Lacey D L, Dunstan C R, Solovyev I, Colombero A, Timms E, Tan H L, Elliott G, Kelley M J, Sarosi I, Wang L, Xia X Z, Elliott R, Chiu L, Black T, Scully S, Capparelli C, Morony S, Shimamoto G, Bass M B, Boyle W J. Tumor necrosis factor receptor family member RANK mediates osteoclast differentiation and activation induced by osteoprotegerin ligand. Proc Natl Acad Sci USA. 1999 Mar. 30; 96(7): 3540-5.

Itasaki, N., Jones, C. M., Mercurio, S., Rowe, A., Domingos, P. M., Smith, J. C., and Krumlauf, R. (2003) Development 130, 4295-4305

Jeon H, Meng W, Takagi J, Eck M J, Springer T A, Blacklow S C. Implications for familial hypercholesterolemia from the structure of the LDL receptor YWTD-EGF domain pair. Nat Struct Biol. 2001 June; 8(6):499-504.

Lintern, K. B., Guidato, S., Rowe, A., Saldanha, J. W., and Itasaki, N. (2009) J Biol Chem 284, 23159-23168.

Liu G, Bafico A, Harris V K, Aaronson S A. A novel mechanism for Wnt activation of canonical signaling through the LRP6 receptor. Mol Cell Biol.(2003) 16:5825-35.

Liu B Y, Soloviev I, Chang P, Lee J, Huang X, et al. (2010) Stromal cell-derived factor-1/CXCL12 contributes to MMTV-Wnt1 tumor growth involving Gr1+CD11b+ cells. PLoS One (2010) 5 (1):1-13; e8611.

McDonald, N. Q., and Hendrickson, W. A. (1993) Cell 73, 421-424.

Mi K, Dolan P J, Johnson G V. The low density lipoprotein receptor-related protein 6 interacts with glycogen synthase kinase 3 and attenuates activity. J Biol. Chem. 2006 Feb. 24; 281(8):4787-94. Epub 2005 Dec. 19.

Mohammad K S, Chirgwin J M, Guise T A. Assessing new bone formation in neonatal calvarial organ cultures. Methods Mol. Biol. 2008; 455:37-50.

Niida A, Hiroko T, Kasai M, Furukawa Y, Nakamura Y, Suzuki Y, Sugano S, Akiyama T. DKK1, a negative regulator of Wnt signaling, is a target of the beta-catenin/TCF pathway. Oncogene. 2004 Nov. 4; 23(52):8520-6.

Nguyen D X, Chiang A C, Zhang X H, Kim J Y, Kris M G, Ladanyi M, Gerald W L, Massague J. WNT/TCF signaling through LEF1 and HOXB9 mediates lung adenocarcinoma metastasis. Cell. 2009 Jul. 10; 138(1):51-62. Epub 2009 Jul. 2.

Piao S, Lee S H, Kim H, Yum S, Stamos J L, Xu Y, Lee S J, Lee J, Oh S, Han J K, Park B J, Weis W I, Ha N C. Direct inhibition of GSK3beta by the phosphorylated cytoplasmic domain of LRP6 in Wnt/beta-catenin signaling. PLoS One. 2008; 3(12):e4046. Epub 2008 Dec. 24.

Quarto N, Wan D C, Kwan M D, Panetta N J, Li S, Longaker M T. Origin Matters: Differences in Embryonic Tissue Origin and Wnt Signaling Determine the Osteogenic Potential and Healing Capacity of Frontal and Parietal Calvarial Bones. J Bone Miner Res. 2009 Nov. 23. [Epub ahead of print]

Rebay I, Fleming R J, Fehon R G, Cherbas L, Cherbas P, Artavanis-Tsakonas S. Specific EGF repeats of Notch mediate interactions with Delta and Serrate: implications for Notch as a multifunctional receptor. Cell. 1991 Nov. 15; 67(4):687-99.

Rudenko, G., Henry, L., Henderson, K., Ichtchenko, K., Brown, M. S., Goldstein, J. L., and Deisenhofer, J. (2002) Science 298, 2353-2358

Schwarz-Romond T, Metcalfe C, Bienz M. Dynamic recruitment of axin by Dishevelled protein assemblies. J Cell Sci. 2007 Jul. 15; 120(Pt 14):2402-12.

Semënov M V, Tamai K, Brott B K, Kahl M, Sokol S, He X. Head inducer Dickkopf-1 is a ligand for Wnt coreceptor LRP6. Curr Biol. 2001 Jun. 26; 11(12):951-61.

Semenov, M., Tamai, K., and He, X. (2005) J Biol Chem 280, 26770-26775.

Springer, T. A. (1998) J Mol Biol 283, 837-862.

Takagi, J., Yang, Y., Liu, J. H., Wang, J. H., and Springer, T. A. (2003) Nature 424, 969-974.

Tamai K, Semenov M, Kato Y, Spokony R, Liu C, Katsuyama Y, Hess F, Saint-Jeannet J P, He X. LDL-receptor-related proteins in Wnt signal transduction. Nature. 2000 Sep. 28; 407(6803):530-5.

Tamai K, Zeng X, Liu C, Zhang X, Harada Y, Chang Z, He X. A mechanism for Wnt coreceptor activation. Mol. Cell. 2004 Jan. 16; 13(1):149-56.

van Amerongen R, Nusse R. Towards an integrated view of Wnt signaling in development. Development. 2009 October; 136(19):3205-14. Veverka, V., Henry, A. J., Slocombe, P. M., Ventom, A., Mulloy, B., Muskett, F. W., Muzylak, M., Greenslade, K., Moore, A., Zhang, L., Gong, J., Qian, X., Paszty, C., Taylor, R. J., Robinson, M. K., and Carr, M. D. (2009) J Biol Chem 284, 10890-10900.

Veverka, V., Henry, A. J., Slocombe, P. M., Ventom, A., Mulloy, B., Muskett, F. W., Muzylak, M., Greenslade, K., Moore, A., Zhang, L., Gong, J., Qian, X., Paszty, C., Taylor, R. J., Robinson, M. K., and Carr, M. D. (2009) *J Biol Chem* 284, 10890-10900

Wu G, Huang H, Garcia Abreu J, He X Inhibition of GSK3 phosphorylation of beta-catenin via phosphorylated PPPSPXS motifs of Wnt coreceptor LRP6. PLoS One. 2009; 4(3):e4926. Epub 2009 Mar. 18.

Yasui N, Mihara E, Nampo M, Tamura-Kawakami K, Unno H, Matsumoto K, Takagi J. Detection of endogenous LRP6 expressed on human cells by monoclonal antibodies specific for the native conformation. J Immunol Methods. (2010) Jan 31; 352(1-2):153-60. Epub 2009 Nov. 26.

Ye, X., et al, The Norrin/Frz4 signaling pathway in retinal vascular development and disease. (2010) Trends Mol. Med. 16, 417-425.

Zhang Y, Appleton B A, Wiesmann C, Lau T, Costa M, Hannoush R N, Sidhu SS Inhibition of Wnt signaling by Dishevelled PDZ peptides. Nat Chem. Biol. 2009 April; 5(4): 217-9. Epub 2009 Mar. 1.

Zeng X, Huang H, Tamai K, Zhang X, Harada Y, Yokota C, Almeida K, Wang J, Doble B, Woodgett J, Wynshaw-Boris A, Hsieh J C, He X. Initiation of Wnt signaling: control of Wnt coreceptor Lrp6 phosphorylation/activation via frizzled, dishevelled and axin functions. Development. 2008 January; 135(2):367-75. Epub 2007 Dec. 12.

Zhou H, Mak W, Kalak R, Street J, Fong-Yee C, Zheng Y, Dunstan C R, Seibel M. Glucocorticoid-dependent Wnt signaling by mature osteoblasts is a key regulator of cranial skeletal development in mice. Development. 2009 February; 136(3):427-36.

Zoltewicz J S, Ashique AM, Choe Y, Lee G, Taylor S, Phamluong K, Solloway M, Peterson AS. Wnt signaling is regulated by endoplasmic reticulum retention. PLoS One. 2009 Jul. 10; 4(7):e6191.

---

What is claimed is:

1. An isolated bispecific antibody that binds to two different regions of low density lipoprotein receptor-related protein 6 (LRP6), wherein the antibody comprises
   a first VH comprising the amino acid sequence of SEQ ID NO: 13,
   a first VL comprising the amino acid sequence of SEQ ID NO: 14,
   a second VH comprising the amino acid sequence of SEQ ID NO: 15, and
   a second VL comprising the amino acid sequence of SEQ ID NO: 14.

2. An isolated bispecific antibody that binds to two different regions of low density lipoprotein receptor-related protein 6 (LRP6), wherein the antibody comprises a first VH domain comprising
   (a) HVR-H1 comprising the amino acid sequence of SEQ ID NO: 20;
   (b) HVR-H2 comprising the amino acid sequence of SEQ ID NO: 18; and
   (c) HVR-H3 comprising the amino acid sequence of SEQ ID NO: 19, a first VL domain comprising
   (g) HVR-L1 comprising the amino acid sequence of SEQ ID NO: 25;
   (h) HVR-L2 comprising the amino acid sequence of SEQ ID NO: 26; and
   (i) HVR-L3 comprising the amino acid sequence of SEQ ID NO:27, a second VH domain comprising
   (d) HVR-H1 comprising the amino acid sequence of SEQ ID NO: 22;
   (e) HVR-H2 comprising the amino acid sequence of SEQ ID NO: 23; and
   (f) HVR-H3 comprising the amino acid sequence of SEQ ID NO: 24, and a second VL domain comprising
   (g) HVR-L1 comprising the amino acid sequence of SEQ ID NO: 25;
   (h) HVR-L2 comprising the amino acid sequence of SEQ ID NO: 26; and
   (i) HVR-L3 comprising the amino acid sequence of SEQ ID NO: 27.

3. The bispecific antibody of claim 2, wherein the antibody inhibits signaling induced by a Wnt isoform selected from the group consisting of Wnt3 and Wnt3a and inhibits signaling induced by a Wnt isoform selected from the group consisting of Wnt 1, 2, 2b, 6, 8a, 9a, 9b, and 10b.

4. The bispecific antibody of claim 2, wherein the antibody inhibits autocrine Wnt signaling.

5. An isolated antibody that binds to the same two epitopes as the bispecific antibody of claim 1.

6. The antibody of claim 5, wherein one of the two epitopes comprises amino acid residues R28, E51, D52, V70, S71, E73, L95, S96, D98, E115, R141, and N185 of the low density lipoprotein receptor-related protein 6 (LRP6) set forth in SEQ ID NO: 29.

7. The antibody of claim 6, wherein the one of the two epitopes further comprises R29, W188, K202, P225, H226, S243, and F266 of the low density lipoprotein receptor-related protein 6 (LRP6) set forth in SEQ ID NO: 29.

8. The antibody of any of claims 5-7, wherein the antibody is a monoclonal antibody.

9. The antibody of any of claims 5-7, wherein the antibody is a chimeric, human or humanized antibody.

10. The antibody of claim 9, wherein the antibody is a chimeric antibody.

11. The antibody of claim 9, wherein the antibody is a human antibody.

12. The antibody of claim 9, wherein the antibody is a humanized antibody.

13. A pharmaceutical formulation comprising the bispecific antibody of claim 1 and a pharmaceutically acceptable carrier.

14. A pharmaceutical formulation comprising the bispecific antibody of claim 2 and a pharmaceutically acceptable carrier.

15. A method of treating an individual having cancer comprising administering to the individual an effective amount of the bispecific antibody of claim 1.

16. A method of treating an individual having cancer comprising administering to the individual an effective amount of the bispecific antibody of claim 2.

* * * * *

SEQUENCE LISTING

```
<160> NUMBER OF SEQ ID NOS: 58

<210> SEQ ID NO 1
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30
```

-continued

```
Tyr Ile Ser Trp Val Arg Gln Ala Pro Gly Lys Gly Leu Glu Trp Val
         35                  40                  45
Ala Glu Ile Ser Pro Tyr Ser Gly Ser Thr Tyr Tyr Ala Asp Ser Val
     50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Leu Arg Ala Arg Pro Pro Ile Arg Leu His Pro Arg Gly Ser Val
            100                 105                 110
Met Asp Tyr Trp Gly Gln Gly Thr Leu Val Thr Val Ser Ser Ala Ser
            115                 120                 125
Thr Lys Gly Pro Ser Val Phe Pro Leu Ala Pro Ser Ser Lys Ser Thr
        130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Glu Glu Met Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
```

```
Ser Leu Ser Leu Ser Pro Gly Lys
    450                 455

<210> SEQ ID NO 2
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Tyr Ile Ser Trp Val Arg Gln Ala Pro Gly Lys Gly Leu Glu Trp Val
        35                  40                  45

Ala Glu Ile Ser Pro Tyr Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80
```

Leu Gln Met Asn Ser Leu Arg Ala Glu Asp Thr Ala Val Tyr Tyr Cys
                85                  90                  95

Ala Leu Arg Ala Arg Pro Pro Ile Arg Leu Tyr Pro Arg Gly Ser Val
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 4
<211> LENGTH: 214
<212> TYPE: PRT
<213> ORGANISM: Artificial Sequence
<220> FEATURE:

<223> OTHER INFORMATION: Synthetic polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Leu Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Tyr
            20                  25                  30

Tyr Ile Ser Trp Val Arg Gln Ala Pro Gly Lys Gly Leu Glu Trp Val
        35                  40                  45

Ala Glu Ile Ser Pro Tyr Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Leu Arg Ala Arg Pro Pro Ile Arg Leu His Pro Arg Gly Ser Val
            100                 105                 110

Met Asp Tyr Trp Gly Gln Gly Thr Leu Val Thr Val Ser Ser Ala Ser
        115                 120                 125

```
Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 6
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 7
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 7

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Ser
             20                  25                  30

Tyr Ile His Trp Val Arg Gln Ala Pro Gly Lys Gly Leu Glu Trp Val
         35                  40                  45

Gly Trp Ile Thr Pro Tyr Gly Gly Tyr Thr Asn Tyr Ala Asp Ser Val
     50                  55                  60

Lys Gly Arg Phe Thr Ile Ser Ala Asp Thr Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Ser Gly His Val Asn Ala Val Lys Asn Tyr Gly Tyr Val
                100                 105                 110

Met Asp Tyr Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Leu Gly Thr Gln Thr Tyr Ile
                195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu Gln
                290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Glu Glu Met Thr
                355                 360                 365

Lys Asn Gln Val Ser Leu Thr Cys Leu Val Lys Gly Phe Tyr Pro Ser
                370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
                450                 455

<210> SEQ ID NO 8
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 9
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Tyr Ile Ser Trp Val Arg Gln Ala Pro Gly Lys Gly Leu Glu Trp Val
        35                  40                  45

Ala Glu Ile Ser Pro Tyr Ser Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Leu Arg Ala Arg Pro Pro Ile Arg Leu His Pro Arg Gly Ser Val
            100                 105                 110

Met Asp Tyr Trp Gly Gln
        115
```

<210> SEQ ID NO 10
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
```

```
                35                  40                  45
Tyr Ser Ala Ser Phe Leu Tyr Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Thr Thr Pro Pro
                 85                  90                  95
Thr Phe Gly Gln Gly Thr Lys Val Glu Ile Lys Arg
                100                 105
```

<210> SEQ ID NO 11
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 11

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Thr Ser Tyr
             20                  25                  30
Tyr Ile Ser Trp Val Arg Gln Ala Pro Gly Lys Gly Leu Glu Trp Val
         35                  40                  45
Ala Glu Ile Ser Pro Tyr Ser Gly Ser Thr Tyr Tyr Ala Asp Ser Val
     50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Leu Arg Ala Arg Pro Pro Ile Arg Leu Tyr Pro Arg Gly Ser Val
                100                 105                 110
Met Asp Tyr Trp Gly Gln
            115
```

<210> SEQ ID NO 12
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 12

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Asp Val Ser Thr Ala
             20                  25                  30
Val Ala Trp Tyr Gln Gln Lys Pro Gly Lys Ala Pro Lys Leu Leu Ile
         35                  40                  45
Tyr Ser Ala Ser Phe Leu Tyr Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Thr Leu Pro Thr
                 85                  90                  95
Thr Phe Gly Gln Gly Thr Lys Val Glu Ile Lys Arg
                100                 105
```

```
<210> SEQ ID NO 13
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Tyr
            20                  25                  30

Tyr Ile Ser Trp Val Arg Gln Ala Pro Gly Lys Gly Leu Glu Trp Val
        35                  40                  45

Ala Glu Ile Ser Pro Tyr Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Leu Arg Ala Arg Pro Pro Ile Arg Leu His Pro Arg Gly Ser Val
            100                 105                 110

Met Asp Tyr Trp Gly Gln
        115

<210> SEQ ID NO 14
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 15
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Ser
```

```
                20                  25                  30
Tyr Ile His Trp Val Arg Gln Ala Pro Gly Lys Gly Leu Glu Trp Val
                35                  40                  45
Gly Trp Ile Thr Pro Tyr Gly Gly Tyr Thr Asn Tyr Ala Asp Ser Val
                50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Gly Ser Gly His Val Asn Ala Val Lys Asn Tyr Gly Tyr Val
                100                 105                 110
Met Asp Tyr Trp Gly Gln
                115

<210> SEQ ID NO 16
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 16

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
                20                  25                  30
Val Ala Trp Tyr Gln Gln Lys Pro Gly Lys Ala Pro Lys Leu Leu Ile
                35                  40                  45
Tyr Ser Ala Ser Phe Leu Tyr Ser Gly Val Pro Ser Arg Phe Ser Gly
                50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Thr Thr Pro Pro
                85                  90                  95
Thr Phe Gly Gln Gly Thr Lys Val Glu Ile Lys Arg
                100                 105

<210> SEQ ID NO 17
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 17

Ser Tyr Tyr Ile Ser
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 18

Glu Ile Ser Pro Tyr Ser Gly Ser Thr Tyr Tyr Ala Asp Ser Val Lys
1               5                   10                  15
Gly
```

```
<210> SEQ ID NO 19
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 19

Arg Ala Arg Pro Pro Ile Arg Leu His Pro Arg Gly Ser Val
1               5                   10

<210> SEQ ID NO 20
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 20

Tyr Tyr Tyr Ile Ser
1               5

<210> SEQ ID NO 21
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 21

Arg Ala Arg Pro Pro Ile Arg Leu Tyr Pro Arg Gly Ser Val
1               5                   10

<210> SEQ ID NO 22
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 22

Asn Ser Tyr Ile His
1               5

<210> SEQ ID NO 23
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 23

Trp Ile Thr Pro Tyr Gly Gly Tyr Thr Asn Tyr Ala Asp Ser Val Lys
1               5                   10                  15

Gly

<210> SEQ ID NO 24
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 24

Gly Ser Gly His Val Asn Ala Val Lys Asn Tyr Gly Tyr Val
1               5                   10
```

```
<210> SEQ ID NO 25
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 25

Arg Ala Ser Gln Asp Val Ser Thr Ala Val Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 26

Ser Ala Ser Phe Leu Tyr Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 27

Gln Gln Ser Tyr Thr Thr Pro Pro Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 28

Gln Gln Ser Tyr Thr Leu Pro Thr Thr
1               5

<210> SEQ ID NO 29
<211> LENGTH: 1613
<212> TYPE: PRT
<213> ORGANISM: Homo sapiens

<400> SEQUENCE: 29

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
            35                  40                  45

Gly Leu Glu Asp Ala Ala Ala Val Asp Phe Val Phe Ser His Gly Leu
        50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95
```

```
Pro Asp Gly Leu Ala Cys Asp Trp Leu Gly Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
        435                 440                 445

Arg Ala Ile Val Leu Asp Pro Met Val Gly Tyr Met Tyr Trp Thr Asp
    450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
```

```
            515                 520                 525
Glu Asp Lys Ile Pro His Ile Phe Gly Phe Thr Leu Leu Gly Asp Tyr
    530                 535                 540
Val Tyr Trp Thr Asp Trp Gln Arg Arg Ser Ile Glu Arg Val His Lys
545                 550                 555                 560
Arg Ser Ala Glu Arg Glu Val Ile Ile Asp Gln Leu Pro Asp Leu Met
                565                 570                 575
Gly Leu Lys Ala Thr Asn Val His Arg Val Ile Gly Ser Asn Pro Cys
            580                 585                 590
Ala Glu Glu Asn Gly Gly Cys Ser His Leu Cys Leu Tyr Arg Pro Gln
        595                 600                 605
Gly Leu Arg Cys Ala Cys Pro Ile Gly Phe Glu Leu Ile Ser Asp Met
    610                 615                 620
Lys Thr Cys Ile Val Pro Glu Ala Phe Leu Leu Phe Ser Arg Arg Ala
625                 630                 635                 640
Asp Ile Arg Arg Ile Ser Leu Glu Thr Asn Asn Asn Asn Val Ala Ile
                645                 650                 655
Pro Leu Thr Gly Val Lys Glu Ala Ser Ala Leu Asp Phe Asp Val Thr
            660                 665                 670
Asp Asn Arg Ile Tyr Trp Thr Asp Ile Ser Leu Lys Thr Ile Ser Arg
        675                 680                 685
Ala Phe Met Asn Gly Ser Ala Leu Glu His Val Val Glu Phe Gly Leu
    690                 695                 700
Asp Tyr Pro Glu Gly Met Ala Val Asp Trp Leu Gly Lys Asn Leu Tyr
705                 710                 715                 720
Trp Ala Asp Thr Gly Thr Asn Arg Ile Glu Val Ser Lys Leu Asp Gly
                725                 730                 735
Gln His Arg Gln Val Leu Val Trp Lys Asp Leu Asp Ser Pro Arg Ala
            740                 745                 750
Leu Ala Leu Asp Pro Ala Glu Gly Phe Met Tyr Trp Thr Glu Trp Gly
        755                 760                 765
Gly Lys Pro Lys Ile Asp Arg Ala Ala Met Asp Gly Ser Glu Arg Thr
    770                 775                 780
Thr Leu Val Pro Asn Val Gly Arg Ala Asn Gly Leu Thr Ile Asp Tyr
785                 790                 795                 800
Ala Lys Arg Arg Leu Tyr Trp Thr Asp Leu Asp Thr Asn Leu Ile Glu
                805                 810                 815
Ser Ser Asn Met Leu Gly Leu Asn Arg Glu Val Ile Ala Asp Asp Leu
            820                 825                 830
Pro His Pro Phe Gly Leu Thr Gln Tyr Gln Asp Tyr Ile Tyr Trp Thr
        835                 840                 845
Asp Trp Ser Arg Arg Ser Ile Glu Arg Ala Asn Lys Thr Ser Gly Gln
    850                 855                 860
Asn Arg Thr Ile Ile Gln Gly His Leu Asp Tyr Val Met Asp Ile Leu
865                 870                 875                 880
Val Phe His Ser Ser Arg Gln Ser Gly Trp Asn Glu Cys Ala Ser Ser
                885                 890                 895
Asn Gly His Cys Ser His Leu Cys Leu Ala Val Pro Val Gly Gly Phe
            900                 905                 910
Val Cys Gly Cys Pro Ala His Tyr Ser Leu Asn Ala Asp Asn Arg Thr
        915                 920                 925
Cys Ser Ala Pro Thr Thr Phe Leu Leu Phe Ser Gln Lys Ser Ala Ile
    930                 935                 940
```

-continued

```
Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Ser Ser Val Pro
        995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Ile Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Glu Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
    1280                1285                1290

Gln Cys Ala Ser Gly Gln Cys Ile Asp Gly Ala Leu Arg Cys Asn
    1295                1300                1305

Gly Asp Ala Asn Cys Gln Asp Lys Ser Asp Glu Lys Asn Cys Glu
    1310                1315                1320

Val Leu Cys Leu Ile Asp Gln Phe Arg Cys Ala Asn Gly Gln Cys
    1325                1330                1335
```

Ile Gly Lys His Lys Lys Cys Asp His Asn Val Asp Cys Ser Asp
    1340                1345                1350

Lys Ser Asp Glu Leu Asp Cys Tyr Pro Thr Glu Glu Pro Ala Pro
    1355                1360                1365

Gln Ala Thr Asn Thr Val Gly Ser Val Ile Gly Val Ile Val Thr
    1370                1375                1380

Ile Phe Val Ser Gly Thr Val Tyr Phe Ile Cys Gln Arg Met Leu
    1385                1390                1395

Cys Pro Arg Met Lys Gly Asp Gly Glu Thr Met Thr Asn Asp Tyr
    1400                1405                1410

Val Val His Gly Pro Ala Ser Val Pro Leu Gly Tyr Val Pro His
    1415                1420                1425

Pro Ser Ser Leu Ser Gly Ser Leu Pro Gly Met Ser Arg Gly Lys
    1430                1435                1440

Ser Met Ile Ser Ser Leu Ser Ile Met Gly Gly Ser Ser Gly Pro
    1445                1450                1455

Pro Tyr Asp Arg Ala His Val Thr Gly Ala Ser Ser Ser Ser Ser
    1460                1465                1470

Ser Ser Thr Lys Gly Thr Tyr Phe Pro Ala Ile Leu Asn Pro Pro
    1475                1480                1485

Pro Ser Pro Ala Thr Glu Arg Ser His Tyr Thr Met Glu Phe Gly
    1490                1495                1500

Tyr Ser Ser Asn Ser Pro Ser Thr His Arg Ser Tyr Ser Tyr Arg
    1505                1510                1515

Pro Tyr Ser Tyr Arg His Phe Ala Pro Pro Thr Thr Pro Cys Ser
    1520                1525                1530

Thr Asp Val Cys Asp Ser Asp Tyr Ala Pro Ser Arg Arg Met Thr
    1535                1540                1545

Ser Val Ala Thr Ala Lys Gly Tyr Thr Ser Asp Leu Asn Tyr Asp
    1550                1555                1560

Ser Glu Pro Val Pro Pro Pro Thr Pro Arg Ser Gln Tyr Leu
    1565                1570                1575

Ser Ala Glu Glu Asn Tyr Glu Ser Cys Pro Pro Ser Pro Tyr Thr
    1580                1585                1590

Glu Arg Ser Tyr Ser His His Leu Tyr Pro Pro Pro Ser Pro
    1595                1600                1605

Cys Thr Asp Ser Ser
    1610

<210> SEQ ID NO 30
<211> LENGTH: 890
<212> TYPE: PRT
<213> ORGANISM: Artificial Sequence
<220> FEATURE:
<223> OTHER INFORMATION: Synthetic polypeptide

<400> SEQUENCE: 30

Met Gly Gly Thr Ala Ala Arg Leu Gly Ala Val Ile Leu Phe Val Val
1               5                   10                  15

Ile Val Gly Leu His Gly Val Arg Gly Lys Gly Ser Ala Ala Pro Leu
                20                  25                  30

Leu Leu Tyr Ala Asn Arg Arg Asp Leu Arg Leu Val Asp Ala Thr Asn
            35                  40                  45

Gly Lys Glu Asn Ala Thr Ile Val Val Gly Gly Leu Glu Asp Ala Ala
        50                  55                  60

```
Ala Val Asp Phe Val Phe Ser His Gly Leu Ile Tyr Trp Ser Asp Val
 65                  70                  75                  80

Ser Glu Glu Ala Ile Lys Arg Thr Glu Phe Asn Lys Thr Glu Ser Val
                 85                  90                  95

Gln Asn Val Val Val Ser Gly Leu Leu Ser Pro Asp Gly Leu Ala Cys
            100                 105                 110

Asp Trp Leu Gly Glu Lys Leu Tyr Trp Thr Asp Ser Glu Thr Asn Arg
        115                 120                 125

Ile Glu Val Ser Asn Leu Asp Gly Ser Leu Arg Lys Val Leu Phe Trp
    130                 135                 140

Gln Glu Leu Asp Gln Pro Arg Ala Ile Ala Leu Asp Pro Ser Ser Gly
145                 150                 155                 160

Phe Met Tyr Trp Thr Asp Trp Gly Glu Val Pro Lys Ile Glu Arg Ala
                165                 170                 175

Gly Met Asp Gly Ser Ser Arg Phe Ile Ile Ile Asn Ser Glu Ile Tyr
            180                 185                 190

Trp Pro Asn Gly Leu Thr Leu Asp Tyr Glu Glu Gln Lys Leu Tyr Trp
        195                 200                 205

Ala Asp Ala Lys Leu Asn Phe Ile His Lys Ser Asn Leu Asp Gly Thr
    210                 215                 220

Asn Arg Gln Ala Val Val Lys Gly Ser Leu Pro His Pro Phe Ala Leu
225                 230                 235                 240

Thr Leu Phe Glu Asp Ile Leu Tyr Trp Thr Asp Trp Ser Thr His Ser
                245                 250                 255

Ile Leu Ala Cys Asn Lys Tyr Thr Gly Glu Gly Leu Arg Glu Ile His
            260                 265                 270

Ser Asp Ile Phe Ser Pro Met Asp Ile His Ala Phe Ser Gln Gln Arg
        275                 280                 285

Gln Pro Asn Ala Thr Asn Pro Cys Gly Ile Asp Asn Gly Gly Cys Ser
    290                 295                 300

His Leu Cys Leu Met Ser Pro Val Lys Pro Phe Tyr Gln Cys Ala Cys
305                 310                 315                 320

Pro Thr Gly Val Lys Leu Leu Glu Asn Gly Lys Thr Cys Lys Asp Gly
                325                 330                 335

Ala Thr Glu Leu Leu Leu Leu Ala Arg Arg Thr Asp Leu Arg Arg Ile
            340                 345                 350

Ser Leu Asp Thr Pro Asp Phe Thr Asp Ile Val Leu Gln Leu Glu Asp
        355                 360                 365

Ile Arg His Ala Ile Ala Ile Asp Tyr Asp Pro Val Glu Gly Tyr Ile
    370                 375                 380

Tyr Trp Thr Asp Asp Glu Val Arg Ala Ile Arg Arg Ser Phe Ile Asp
385                 390                 395                 400

Gly Ser Gly Ser Gln Phe Val Val Thr Ala Gln Ile Ala His Pro Asp
                405                 410                 415

Gly Ile Ala Val Asp Trp Val Ala Arg Asn Leu Tyr Trp Thr Asp Thr
            420                 425                 430

Gly Thr Asp Arg Ile Glu Val Thr Arg Leu Asn Gly Thr Met Arg Lys
        435                 440                 445

Ile Leu Ile Ser Glu Asp Leu Glu Glu Pro Arg Ala Ile Val Leu Asp
    450                 455                 460

Pro Met Val Gly Tyr Met Tyr Trp Thr Asp Trp Gly Glu Ile Pro Lys
465                 470                 475                 480

Ile Glu Arg Ala Ala Leu Asp Gly Ser Asp Arg Val Val Leu Val Asn
```

```
                485                 490                 495
Thr Ser Leu Gly Trp Pro Asn Gly Leu Ala Leu Asp Tyr Asp Glu Gly
            500                 505                 510
Lys Ile Tyr Trp Gly Asp Ala Lys Thr Asp Lys Ile Glu Val Met Asn
            515                 520                 525
Thr Asp Gly Thr Gly Arg Arg Val Leu Val Glu Asp Lys Ile Pro His
            530                 535                 540
Ile Phe Gly Phe Thr Leu Leu Gly Asp Tyr Val Tyr Trp Thr Asp Trp
545                 550                 555                 560
Gln Arg Arg Ser Ile Glu Arg Val His Lys Arg Ser Ala Glu Arg Glu
                565                 570                 575
Val Ile Ile Asp Gln Leu Pro Asp Leu Met Gly Leu Lys Ala Thr Asn
            580                 585                 590
Val His Arg Val Ile Gly Ser Asn Pro Cys Ala Glu Glu Asn Gly Gly
            595                 600                 605
Cys Ser His Leu Cys Leu Tyr Arg Pro Gln Gly Leu Arg Cys Ala Cys
            610                 615                 620
Pro Ile Gly Phe Glu Leu Ile Ser Asp Met Lys Thr Cys Ile Val Pro
625                 630                 635                 640
Glu Ala Phe Leu Leu Phe Ser Arg Arg Ala Asp Ile Arg Arg Leu Glu
                645                 650                 655
Ser Gly Gly Gly Val Thr Asp Lys Thr His Thr Cys Pro Pro Cys
            660                 665                 670
Pro Ala Pro Glu Leu Leu Gly Gly Pro Ser Val Phe Leu Phe Pro Pro
            675                 680                 685
Lys Pro Lys Asp Thr Leu Met Ile Ser Arg Thr Pro Glu Val Thr Cys
            690                 695                 700
Val Val Val Asp Val Ser His Glu Asp Pro Glu Val Lys Phe Asn Trp
705                 710                 715                 720
Tyr Val Asp Gly Val Glu Val His Asn Ala Lys Thr Lys Pro Arg Glu
                725                 730                 735
Glu Gln Tyr Asn Ser Thr Tyr Arg Val Val Ser Val Leu Thr Val Leu
            740                 745                 750
His Gln Asp Trp Leu Asn Gly Lys Glu Tyr Lys Cys Lys Val Ser Asn
            755                 760                 765
Lys Ala Leu Pro Ala Pro Ile Glu Lys Thr Ile Ser Lys Ala Lys Gly
            770                 775                 780
Gln Pro Arg Glu Pro Gln Val Tyr Thr Leu Pro Pro Ser Arg Glu Glu
785                 790                 795                 800
Met Thr Lys Asn Gln Val Ser Leu Thr Cys Leu Val Lys Gly Phe Tyr
                805                 810                 815
Pro Ser Asp Ile Ala Val Glu Trp Glu Ser Asn Gly Gln Pro Glu Asn
            820                 825                 830
Asn Tyr Lys Thr Thr Pro Pro Val Leu Asp Ser Asp Gly Ser Phe Phe
            835                 840                 845
Leu Tyr Ser Lys Leu Thr Val Asp Lys Ser Arg Trp Gln Gln Gly Asn
            850                 855                 860
Val Phe Ser Cys Ser Val Met His Glu Ala Leu His Asn His Tyr Thr
865                 870                 875                 880
Gln Lys Ser Leu Ser Leu Ser Pro Gly Lys
                885                 890

<210> SEQ ID NO 31
```

<211> LENGTH: 882
<212> TYPE: PRT
<213> ORGANISM: Artificial Sequence
<220> FEATURE:
<223> OTHER INFORMATION: Synthetic polypeptide

<400> SEQUENCE: 31

```
Met Gly Gly Thr Ala Ala Arg Leu Gly Ala Val Ile Leu Phe Val Val
1               5                   10                  15

Ile Val Gly Leu His Gly Val Arg Gly Lys Gly Ser Val Pro Glu Ala
            20                  25                  30

Phe Leu Leu Phe Ser Arg Arg Ala Asp Ile Arg Arg Ile Ser Leu Glu
            35                  40                  45

Thr Asn Asn Asn Val Ala Ile Pro Leu Thr Gly Val Lys Glu Ala
        50                  55                  60

Ser Ala Leu Asp Phe Asp Val Thr Asp Asn Arg Ile Tyr Trp Thr Asp
65                  70                  75                  80

Ile Ser Leu Lys Thr Ile Ser Arg Ala Phe Met Asn Gly Ser Ala Leu
                85                  90                  95

Glu His Val Val Glu Phe Gly Leu Asp Tyr Pro Gly Met Ala Val
            100                 105                 110

Asp Trp Leu Gly Lys Asn Leu Tyr Trp Ala Asp Thr Gly Thr Asn Arg
            115                 120                 125

Ile Glu Val Ser Lys Leu Asp Gly Gln His Arg Gln Val Leu Val Trp
            130                 135                 140

Lys Asp Leu Asp Ser Pro Arg Ala Leu Ala Leu Asp Pro Ala Glu Gly
145                 150                 155                 160

Phe Met Tyr Trp Thr Glu Trp Gly Gly Lys Pro Lys Ile Asp Arg Ala
                165                 170                 175

Ala Met Asp Gly Ser Glu Arg Thr Thr Leu Val Pro Asn Val Gly Arg
            180                 185                 190

Ala Asn Gly Leu Thr Ile Asp Tyr Ala Lys Arg Arg Leu Tyr Trp Thr
            195                 200                 205

Asp Leu Asp Thr Asn Leu Ile Glu Ser Ser Asn Met Leu Gly Leu Asn
        210                 215                 220

Arg Glu Val Ile Ala Asp Asp Leu Pro His Pro Phe Gly Leu Thr Gln
225                 230                 235                 240

Tyr Gln Asp Tyr Ile Tyr Trp Thr Asp Trp Ser Arg Arg Ser Ile Glu
                245                 250                 255

Arg Ala Asn Lys Thr Ser Gly Gln Asn Arg Thr Ile Ile Gln Gly His
            260                 265                 270

Leu Asp Tyr Val Met Asp Ile Leu Val Phe His Ser Arg Gln Ser
            275                 280                 285

Gly Trp Asn Glu Cys Ala Ser Ser Asn Gly His Cys Ser His Leu Cys
            290                 295                 300

Leu Ala Val Pro Val Gly Gly Phe Val Cys Gly Cys Pro Ala His Tyr
305                 310                 315                 320

Ser Leu Asn Ala Asp Asn Arg Thr Cys Ser Ala Pro Thr Thr Phe Leu
                325                 330                 335

Leu Phe Ser Gln Lys Ser Ala Ile Asn Arg Met Val Ile Asp Glu Gln
            340                 345                 350

Gln Ser Pro Asp Ile Ile Leu Pro Ile His Ser Leu Arg Asn Val Arg
            355                 360                 365

Ala Ile Asp Tyr Asp Pro Leu Asp Lys Gln Leu Tyr Trp Ile Asp Ser
            370                 375                 380
```

```
-continued

Arg Gln Asn Met Ile Arg Lys Ala Gln Glu Asp Gly Ser Gln Gly Phe
385                 390                 395                 400

Thr Val Val Val Ser Val Pro Ser Gln Asn Leu Glu Ile Gln Pro
        405                 410                 415

Tyr Asp Leu Ser Ile Asp Ile Tyr Ser Arg Tyr Ile Tyr Trp Thr Cys
        420                 425                 430

Glu Ala Thr Asn Val Ile Asn Val Thr Arg Leu Asp Gly Arg Ser Val
            435                 440                 445

Gly Val Val Leu Lys Gly Gln Asp Arg Pro Arg Ala Ile Val Val
        450                 455                 460

Asn Pro Glu Lys Gly Tyr Met Tyr Phe Thr Asn Leu Gln Glu Arg Ser
465                 470                 475                 480

Pro Lys Ile Glu Arg Ala Ala Leu Asp Gly Thr Glu Arg Glu Val Leu
                485                 490                 495

Phe Phe Ser Gly Leu Ser Lys Pro Ile Ala Leu Ala Leu Asp Ser Arg
            500                 505                 510

Leu Gly Lys Leu Phe Trp Ala Asp Ser Asp Leu Arg Arg Ile Glu Ser
        515                 520                 525

Ser Asp Leu Ser Gly Ala Asn Arg Ile Val Leu Glu Asp Ser Asn Ile
530                 535                 540

Leu Gln Pro Val Gly Leu Thr Val Phe Glu Asn Trp Leu Tyr Trp Ile
545                 550                 555                 560

Asp Lys Gln Gln Gln Met Ile Glu Lys Ile Asp Met Thr Gly Arg Glu
                565                 570                 575

Gly Arg Thr Lys Val Gln Ala Arg Ile Ala Gln Leu Ser Asp Ile His
            580                 585                 590

Ala Val Lys Glu Leu Asn Leu Gln Glu Tyr Arg Gln His Pro Cys Ala
        595                 600                 605

Gln Asp Asn Gly Gly Cys Ser His Ile Cys Leu Val Lys Gly Asp Gly
        610                 615                 620

Thr Thr Arg Cys Ser Cys Pro Met His Leu Val Leu Leu Gln Asp Glu
625                 630                 635                 640

Leu Ser Cys Gly Thr Gly Leu Glu Ser Gly Gly Gly Val Thr Asp
            645                 650                 655

Lys Thr His Thr Cys Pro Pro Cys Pro Ala Pro Glu Leu Leu Gly Gly
                660                 665                 670

Pro Ser Val Phe Leu Phe Pro Pro Lys Pro Lys Asp Thr Leu Met Ile
        675                 680                 685

Ser Arg Thr Pro Glu Val Thr Cys Val Val Val Asp Val Ser His Glu
        690                 695                 700

Asp Pro Glu Val Lys Phe Asn Trp Tyr Val Asp Gly Val Glu Val His
705                 710                 715                 720

Asn Ala Lys Thr Lys Pro Arg Glu Glu Gln Tyr Asn Ser Thr Tyr Arg
                725                 730                 735

Val Val Ser Val Leu Thr Val Leu His Gln Asp Trp Leu Asn Gly Lys
            740                 745                 750

Glu Tyr Lys Cys Lys Val Ser Asn Lys Ala Leu Pro Ala Pro Ile Glu
        755                 760                 765

Lys Thr Ile Ser Lys Ala Lys Gly Gln Pro Arg Glu Pro Gln Val Tyr
        770                 775                 780

Thr Leu Pro Pro Ser Arg Glu Glu Met Thr Lys Asn Gln Val Ser Leu
785                 790                 795                 800
```

```
Thr Cys Leu Val Lys Gly Phe Tyr Pro Ser Asp Ile Ala Val Glu Trp
            805                 810                 815

Glu Ser Asn Gly Gln Pro Glu Asn Asn Tyr Lys Thr Thr Pro Pro Val
        820                 825                 830

Leu Asp Ser Asp Gly Ser Phe Phe Leu Tyr Ser Lys Leu Thr Val Asp
            835                 840                 845

Lys Ser Arg Trp Gln Gln Gly Asn Val Phe Ser Cys Ser Val Met His
    850                 855                 860

Glu Ala Leu His Asn His Tyr Thr Gln Lys Ser Leu Ser Leu Ser Pro
865                 870                 875                 880

Gly Lys

<210> SEQ ID NO 32
<211> LENGTH: 23
<212> TYPE: DNA
<213> ORGANISM: Artificial Sequence
<220> FEATURE:
<223> OTHER INFORMATION: Synthetic sequence

<400> SEQUENCE: 32
aatgctgctg aactgaatag aaa                                          23

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 33
aaccggtcct agcgaaaa                                                18

<210> SEQ ID NO 34
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 34
ccgagcactg tttcaaatct ccca                                         24

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
tgagagtgtg acattgttgg aa                                           22

<210> SEQ ID NO 36
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 36
gtaaaatctg tgtgcaatta tcatgt                                       26

<210> SEQ ID NO 37
```

```
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 37
aatcattgaa aatgactaac acaagaccct gtaaat                              36

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 38
tgaggacgca ggagtgaa                                                  18

<210> SEQ ID NO 39
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 39
cccagagagt ggccaaat                                                  18

<210> SEQ ID NO 40
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 40
cctgtttgct gccacccatg a                                              21

<210> SEQ ID NO 41
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is I or V

<400> SEQUENCE: 41

Asn Xaa Xaa Lys
1

<210> SEQ ID NO 42
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: X is any amino acid
<220> FEATURE:
```

```
<221> NAME/KEY: MISC_FEATURE
<222> LOCATION: (3)..(3)
<223> OTHER INFORMATION: X is I or V

<400> SEQUENCE: 42

Asn Xaa Xaa Lys Asn
1               5

<210> SEQ ID NO 43
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: X is any amino acid

<400> SEQUENCE: 43

Asn Xaa Val Lys
1

<210> SEQ ID NO 44
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: X is any amino acid

<400> SEQUENCE: 44

Asn Xaa Ile Lys
1

<210> SEQ ID NO 45
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: X is any amino acid

<400> SEQUENCE: 45

Asn Xaa Val Lys Asn
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: X is any amino acid

<400> SEQUENCE: 46

Asn Xaa Ile Lys Asn
1               5

<210> SEQ ID NO 47
```

```
<210> SEQ ID NO 47
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 47

Asn Ala Val Lys
1

<210> SEQ ID NO 48
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 48

Asn Ala Ile Lys
1

<210> SEQ ID NO 49
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 49

Asn Ala Val Lys Asn
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 50

Asn Ala Ile Lys Asn
1               5

<210> SEQ ID NO 51
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Trp Ile His Trp Val Arg Gln Ala Pro Gly Lys Gly Leu Glu Trp Val
        35                  40                  45

Gly Thr Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Asp Trp Arg Phe His His Ala Gly Glu Tyr Ala Met Asp
```

<210> SEQ ID NO 52
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Trp Ile His Trp Val Arg Gln Ala Pro Gly Lys Gly Leu Glu Trp Val
        35                  40                  45

Ala Gly Ile Ser Pro Asp Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ser Tyr Ile Ser Arg Tyr Phe Ser Ser Val Met Asp Tyr
            100                 105                 110

Trp Gly Gln
        115

<210> SEQ ID NO 53
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Asp Ile His Trp Val Arg Gln Ala Pro Gly Lys Gly Leu Glu Trp Val
        35                  40                  45

Ala Ser Ile Tyr Pro Ala Gly Gly Asp Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Pro Gly Trp Ala Leu Arg Gly Ala Met Asp Tyr Trp Gly
            100                 105                 110

Gln

<210> SEQ ID NO 54
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asn
            20                  25                  30

Asp Ile His Trp Val Arg Gln Ala Pro Gly Lys Gly Leu Glu Trp Val
        35                  40                  45

Gly Arg Ile Tyr Pro Tyr Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Glu Val Thr Tyr His Leu Phe Asp Tyr Trp Gly Gln
            100                 105                 110

<210> SEQ ID NO 55
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Ile Ser Trp Val Arg Gln Ala Pro Gly Lys Gly Leu Glu Trp Val
        35                  40                  45

Gly Val Ile Ser Pro Ser Ser Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Pro Ala Gly Ala Phe Leu Gly Tyr Tyr Gly Met Asp Tyr
            100                 105                 110

Trp Gly Gln
        115

<210> SEQ ID NO 56
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Phe Tyr
            20                  25                  30

Tyr Leu Ser Trp Val Arg Gln Ala Pro Gly Lys Gly Leu Glu Trp Val
        35                  40                  45

Ala Glu Ile Ser Pro Tyr Ser Gly Ser Thr Tyr Tyr Ala Asp Ser Val
    50                  55                  60

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Leu Arg Ala Arg Pro Pro Ile Arg Leu His Pro Arg Gly Ser Val
            100                 105                 110

Met Asp Tyr Trp Gly Gln
            115

<210> SEQ ID NO 57
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 57

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Gly Phe Tyr
             20                  25                  30

Tyr Ile Ser Trp Val Arg Gln Ala Pro Gly Lys Gly Leu Glu Trp Val
         35                  40                  45

Ala Glu Ile Ser Pro Tyr Ser Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Leu Arg Ala Arg Pro Pro Ile Arg Leu His Pro Arg Gly Ser Val
            100                 105                 110

Met Asp Tyr Trp Gly Gln
            115

<210> SEQ ID NO 58
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 58

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ala Ile Pro Thr
                 85                  90                  95

Thr Phe Gly Gln Gly Thr Lys Val Glu Ile Lys Arg
            100                 105
```